(12) United States Patent
Hood et al.

(10) Patent No.: US 8,998,884 B2
(45) Date of Patent: Apr. 7, 2015

(54) REMOTE CONTROLLED IN SITU REACTION METHOD

(75) Inventors: Leroy E. Hood, Seattle, WA (US); Muriel Y. Ishikawa, Livermore, CA (US); Edward K. Y. Jung, Bellevue, WA (US); Robert Langer, Newton, MA (US); Clarence T. Tegreene, Bellevue, WA (US); Lowell L. Wood, Jr., Livermore, CA (US); Victoria Y. H. Wood, Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 1243 days.

(21) Appl. No.: 11/270,799

(22) Filed: Nov. 9, 2005

(65) Prior Publication Data

US 2007/0106266 A1  May 10, 2007

(51) Int. Cl.
  *A61K 9/22* (2006.01)
  *A61K 9/00* (2006.01)
  *A61K 41/00* (2006.01)
  *A61M 5/142* (2006.01)
  *A61M 5/145* (2006.01)
  *A61M 5/172* (2006.01)

(52) U.S. Cl.
  CPC .............. *A61K 9/0009* (2013.01); *A61K 41/00* (2013.01); *A61M 5/14276* (2013.01); *A61M 5/145* (2013.01); *A61M 5/172* (2013.01); *A61M 5/1723* (2013.01); *A61M 2005/14513* (2013.01); *A61M 2205/0266* (2013.01); *A61M 2205/0288* (2013.01); *A61M 2205/3523* (2013.01); *A61M 2205/3569* (2013.01); *A61M 2205/36* (2013.01)

(58) Field of Classification Search
  CPC ........... A61M 2005/14513; A61M 2205/0266; A61M 2205/0288; A61M 5/14276; A61M 5/145; A61M 5/172
  USPC ....................................... 604/890.1, 289–291
  See application file for complete search history.

(56) References Cited

U.S. PATENT DOCUMENTS 3,760,806 A   9/1973  Leeper
3,923,426 A   12/1975 Theeuwes
(Continued)

FOREIGN PATENT DOCUMENTS

JP   60118289 (A)    6/1985
WO   WO 02/056790 A2 7/2002
(Continued)

OTHER PUBLICATIONS

Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.
(Continued)

*Primary Examiner* — Aarti B Berdichevsky

(57) ABSTRACT

Embodiments of a system including a remotely controlled reaction device and associated controller are described. Methods of use and control of the device are also disclosed. According to various embodiments, a reaction device is placed in an environment in order to perform a chemical reaction in an environment. Exemplary environments include a body of an organism, a body of water, or an enclosed volume of a fluid. In selected embodiments, a magnetic field, an electric field, or electromagnetic control signal may be used.

32 Claims, 29 Drawing Sheets

(56) References Cited

U.S. PATENT DOCUMENTS

| | | |
|---|---|---|
| 4,053,952 A | 10/1977 | Goldstein |
| 4,263,910 A | 4/1981 | Pardekooper et al. |
| 4,360,019 A | 11/1982 | Portner et al. |
| 4,373,527 A | 2/1983 | Fischell |
| 4,457,752 A | 7/1984 | Vadasz |
| 4,513,034 A | 4/1985 | Sparer et al. |
| 4,579,837 A | 4/1986 | Busch et al. |
| 4,642,230 A | 2/1987 | Whitehead et al. |
| 4,692,147 A | 9/1987 | Duggan |
| 4,714,462 A | 12/1987 | DiDomenico |
| 4,753,636 A | 6/1988 | Free |
| 4,779,806 A | 10/1988 | Langer et al. |
| 4,787,888 A | 11/1988 | Fox |
| 4,834,704 A | 5/1989 | Reinicke |
| 4,861,484 A | 8/1989 | Lichtin et al. |
| 4,883,666 A | 11/1989 | Sabel et al. |
| 4,929,233 A | 5/1990 | Roth et al. |
| 4,944,659 A | 7/1990 | Labbe et al. |
| 4,952,406 A | 8/1990 | Brown et al. |
| 5,019,372 A | 5/1991 | Folkman et al. |
| 5,045,082 A | 9/1991 | Ayer et al. |
| 5,049,141 A | 9/1991 | Olive |
| 5,059,175 A | 10/1991 | Hanover et al. |
| 5,167,625 A | 12/1992 | Jacobsen et al. |
| 5,170,801 A | 12/1992 | Casper et al. |
| 5,207,666 A | 5/1993 | Idriss et al. |
| 5,217,449 A | 6/1993 | Yuda et al. |
| 5,279,607 A | 1/1994 | Schentag et al. |
| 5,368,571 A | 11/1994 | Horres, Jr. |
| 5,370,611 A | 12/1994 | Niezink et al. |
| 5,370,672 A | 12/1994 | Fowler et al. |
| 5,391,164 A | 2/1995 | Giampapa |
| 5,395,366 A | 3/1995 | D'Andrea et al. |
| 5,484,403 A | 1/1996 | Yoakum et al. |
| 5,505,706 A | 4/1996 | Maus et al. |
| 5,523,746 A | 6/1996 | Gallagher |
| 5,643,246 A | 7/1997 | Leeb et al. |
| 5,644,177 A | 7/1997 | Guckel et al. |
| 5,651,979 A | 7/1997 | Ron et al. |
| 5,655,539 A | 8/1997 | Wang et al. |
| 5,666,977 A | 9/1997 | Higgins et al. |
| 5,667,504 A | 9/1997 | Baumann et al. |
| 5,698,220 A | 12/1997 | Cardinal et al. |
| 5,719,296 A | 2/1998 | Acton, III et al. |
| 5,733,313 A | 3/1998 | Barreras, Sr. et al. |
| 5,770,222 A | 6/1998 | Unger et al. |
| 5,797,898 A | 8/1998 | Santini, Jr. et al. |
| 5,800,420 A | 9/1998 | Gross et al. |
| 5,814,599 A | 9/1998 | Mitragotri et al. |
| 5,827,186 A | 10/1998 | Chen et al. |
| 5,830,207 A | 11/1998 | Leeb et al. |
| 5,869,078 A | 2/1999 | Baudino |
| 5,879,329 A | 3/1999 | Ginsburg |
| 5,928,195 A | 7/1999 | Malamud et al. |
| 5,935,593 A | 8/1999 | Ron et al. |
| 5,945,762 A | 8/1999 | Chen et al. |
| 5,993,414 A | 11/1999 | Haller |
| 6,048,328 A * | 4/2000 | Haller et al. ............. 604/288.03 |
| 6,048,734 A | 4/2000 | Burns et al. |
| 6,077,837 A | 6/2000 | Kozak |
| 6,086,582 A | 7/2000 | Altman et al. |
| 6,116,863 A | 9/2000 | Ahn et al. |
| 6,122,536 A | 9/2000 | Sun et al. |
| 6,146,103 A | 11/2000 | Lee et al. |
| 6,152,181 A | 11/2000 | Wapner et al. |
| 6,198,950 B1 | 3/2001 | Kraus |
| 6,198,963 B1 | 3/2001 | Haim et al. |
| 6,203,523 B1 | 3/2001 | Haller et al. |
| 6,206,914 B1 | 3/2001 | Soykan et al. |
| 6,246,241 B1 | 6/2001 | Newland |
| 6,261,584 B1 | 7/2001 | Peery et al. |
| 6,269,340 B1 | 7/2001 | Ford et al. |
| 6,270,680 B1 | 8/2001 | Silveri et al. |
| 6,272,370 B1 | 8/2001 | Gillies et al. |
| 6,312,393 B1 | 11/2001 | Abreu |
| 6,339,897 B1 | 1/2002 | Hayes et al. |
| 6,358,247 B1 | 3/2002 | Altman et al. |
| 6,395,292 B2 | 5/2002 | Peery et al. |
| 6,408,878 B2 | 6/2002 | Unger et al. |
| 6,416,495 B1 | 7/2002 | Kriesel et al. |
| 6,436,069 B1 | 8/2002 | Jellie |
| 6,454,759 B2 * | 9/2002 | Krulevitch et al. ........ 604/891.1 |
| 6,458,118 B1 | 10/2002 | Lent et al. |
| 6,464,687 B1 | 10/2002 | Ishikawa et al. |
| 6,475,750 B1 | 11/2002 | Han et al. |
| 6,491,061 B1 | 12/2002 | Lopez et al. |
| 6,491,684 B1 | 12/2002 | Joshi et al. |
| 6,500,165 B1 | 12/2002 | Frank |
| 6,500,168 B1 | 12/2002 | Jellie |
| 6,511,473 B2 | 1/2003 | Bartha et al. |
| 6,537,256 B2 | 3/2003 | Santini, Jr. et al. |
| 6,544,193 B2 | 4/2003 | Abreu |
| 6,554,822 B1 | 4/2003 | Holschneider et al. |
| 6,562,000 B2 | 5/2003 | Thompson et al. |
| 6,565,526 B2 | 5/2003 | Seward |
| 6,569,152 B2 | 5/2003 | Brines et al. |
| 6,571,125 B2 | 5/2003 | Thompson |
| 6,585,763 B1 | 7/2003 | Keilman et al. |
| 6,589,205 B1 | 7/2003 | Meadows |
| 6,590,267 B1 | 7/2003 | Goodwin-Johansson et al. |
| 6,607,553 B1 | 8/2003 | Healy et al. |
| 6,615,855 B2 | 9/2003 | Lopez et al. |
| 6,628,989 B1 | 9/2003 | Penner et al. |
| 6,632,216 B2 | 10/2003 | Houzego et al. |
| 6,635,837 B2 | 10/2003 | Subramanian et al. |
| 6,653,124 B1 | 11/2003 | Freeman |
| 6,663,821 B2 | 12/2003 | Seward |
| 6,669,683 B2 | 12/2003 | Santini, Jr. et al. |
| 6,682,521 B2 | 1/2004 | Petrakis |
| 6,719,449 B1 | 4/2004 | Laugharn, Jr. et al. |
| 6,720,402 B2 | 4/2004 | Langer et al. |
| 6,723,086 B2 | 4/2004 | Bassuk et al. |
| 6,755,621 B2 | 6/2004 | Lopez et al. |
| 6,761,420 B2 | 7/2004 | Maluf et al. |
| 6,768,425 B2 | 7/2004 | Flaherty et al. |
| 6,768,920 B2 | 7/2004 | Lange et al. |
| 6,773,429 B2 | 8/2004 | Sheppard, Jr. et al. |
| 6,793,753 B2 | 9/2004 | Unger et al. |
| 6,796,956 B2 | 9/2004 | Hartlaub et al. |
| 6,802,489 B2 | 10/2004 | Marr et al. |
| 6,802,811 B1 | 10/2004 | Slepian |
| 6,805,783 B2 | 10/2004 | Ohkawa |
| 6,808,522 B2 | 10/2004 | Richards et al. |
| 6,824,561 B2 | 11/2004 | Soykan et al. |
| 6,830,936 B2 | 12/2004 | Anderson et al. |
| 6,845,267 B2 | 1/2005 | Harrison et al. |
| 6,849,463 B2 | 2/2005 | Santini, Jr. et al. |
| 6,929,636 B1 | 8/2005 | von Alten |
| 6,935,165 B2 | 8/2005 | Bashir et al. |
| 6,948,843 B2 | 9/2005 | Laugharn, Jr. et al. |
| 6,970,741 B1 | 11/2005 | Whitehurst et al. |
| 7,048,730 B2 | 5/2006 | Petrakis |
| 7,083,593 B2 | 8/2006 | Stultz |
| 7,104,988 B2 | 9/2006 | Altman et al. |
| 7,118,531 B2 | 10/2006 | Krill |
| 7,214,190 B1 | 5/2007 | Wilson |
| 7,351,239 B2 | 4/2008 | Gill |
| 7,424,330 B2 * | 9/2008 | Duerr et al. ..................... 700/19 |
| 7,474,180 B2 | 1/2009 | Bintoro et al. |
| 7,641,619 B2 | 1/2010 | Penner |
| 7,699,834 B2 | 4/2010 | Hood et al. |
| 7,811,279 B2 | 10/2010 | John |
| 7,817,030 B2 | 10/2010 | Hood et al. |
| 7,819,858 B2 | 10/2010 | Goodall et al. |
| 7,896,867 B2 | 3/2011 | Gordon et al. |
| 7,896,868 B2 | 3/2011 | Hood et al. |
| 7,942,867 B2 | 5/2011 | Hood et al. |
| 8,083,710 B2 | 12/2011 | Hood et al. |
| 8,109,923 B2 | 2/2012 | Hood et al. |
| 8,114,065 B2 | 2/2012 | Hood et al. |
| 8,192,390 B2 | 6/2012 | Hood et al. |
| 8,273,075 B2 | 9/2012 | Hood et al. |
| 8,348,930 B2 | 1/2013 | Gordon et al. |
| 8,349,261 B2 | 1/2013 | Hood et al. |

(56) References Cited

U.S. PATENT DOCUMENTS

| | | | |
|---|---|---|---|
| 8,367,003 B2 | 2/2013 | Hood et al. | |
| 8,512,241 B2 | 8/2013 | Bandy et al. | |
| 8,529,551 B2 | 9/2013 | Hood et al. | |
| 2001/0033796 A1 | 10/2001 | Unger et al. | |
| 2001/0036672 A1 | 11/2001 | Anderson et al. | |
| 2001/0039414 A1 | 11/2001 | Brines et al. | |
| 2001/0044620 A1 | 11/2001 | Krulevitch et al. | |
| 2002/0009015 A1 | 1/2002 | Laugharn, Jr. et al. | |
| 2002/0065509 A1 | 5/2002 | Lebel et al. | |
| 2002/0070116 A1 | 6/2002 | Ohkawa | |
| 2002/0072784 A1* | 6/2002 | Sheppard et al. | 607/60 |
| 2002/0077673 A1 | 6/2002 | Penner et al. | |
| 2002/0090388 A1 | 7/2002 | Humes et al. | |
| 2002/0107472 A1 | 8/2002 | Thompson et al. | |
| 2002/0111601 A1 | 8/2002 | Thompson | |
| 2002/0127736 A1 | 9/2002 | Chou et al. | |
| 2002/0173772 A1 | 11/2002 | Olsen | |
| 2002/0173773 A1 | 11/2002 | Olsen | |
| 2002/0188323 A1 | 12/2002 | Penner et al. | |
| 2003/0015768 A1 | 1/2003 | Bosco et al. | |
| 2003/0036746 A1 | 2/2003 | Penner et al. | |
| 2003/0069560 A1 | 4/2003 | Adamis et al. | |
| 2003/0070677 A1 | 4/2003 | Handique et al. | |
| 2003/0104590 A1 | 6/2003 | Santini, Jr. et al. | |
| 2003/0142901 A1 | 7/2003 | Lahann et al. | |
| 2003/0147812 A1 | 8/2003 | Ueberle | |
| 2003/0163223 A1 | 8/2003 | Blomquist | |
| 2003/0171257 A1 | 9/2003 | Stirbl et al. | |
| 2003/0171738 A1 | 9/2003 | Konieczynski et al. | |
| 2003/0210997 A1 | 11/2003 | Lopez et al. | |
| 2003/0219470 A1 | 11/2003 | Zhang et al. | |
| 2003/0234220 A1 | 12/2003 | Lee et al. | |
| 2003/0235504 A1 | 12/2003 | Lemoff et al. | |
| 2004/0007051 A1 | 1/2004 | Bashir et al. | |
| 2004/0010219 A1 | 1/2004 | McCusker et al. | |
| 2004/0015154 A1 | 1/2004 | Harper et al. | |
| 2004/0032187 A1 | 2/2004 | Penner et al. | |
| 2004/0034332 A1 | 2/2004 | Uhland | |
| 2004/0036455 A1 | 2/2004 | Cho | |
| 2004/0049245 A1 | 3/2004 | Gass et al. | |
| 2004/0055648 A1 | 3/2004 | Erickson | |
| 2004/0058101 A1 | 3/2004 | Klemm | |
| 2004/0076559 A1 | 4/2004 | Brucker et al. | |
| 2004/0079424 A1 | 4/2004 | Takeda et al. | |
| 2004/0082908 A1 | 4/2004 | Whitehurst et al. | |
| 2004/0106914 A1 | 6/2004 | Coppeta et al. | |
| 2004/0115128 A1 | 6/2004 | Schnitzer | |
| 2004/0120827 A1 | 6/2004 | Kim et al. | |
| 2004/0121486 A1 | 6/2004 | Uhland et al. | |
| 2004/0127844 A1 | 7/2004 | Flaherty | |
| 2004/0133188 A1 | 7/2004 | Vardi et al. | |
| 2004/0137300 A1 | 7/2004 | Gemmen et al. | |
| 2004/0147906 A1* | 7/2004 | Voyiazis et al. | 604/891.1 |
| 2004/0166140 A1 | 8/2004 | Santini, Jr. et al. | |
| 2004/0186576 A1 | 9/2004 | Biscup et al. | |
| 2004/0193144 A1 | 9/2004 | Krumme | |
| 2004/0193166 A1 | 9/2004 | Biscup | |
| 2004/0204744 A1 | 10/2004 | Penner et al. | |
| 2004/0210184 A1 | 10/2004 | Kost et al. | |
| 2004/0219732 A1 | 11/2004 | Burns et al. | |
| 2004/0220553 A1 | 11/2004 | Olsen | |
| 2004/0223985 A1 | 11/2004 | Dunfield et al. | |
| 2004/0230182 A1 | 11/2004 | Heruth et al. | |
| 2004/0242976 A1 | 12/2004 | Abreu | |
| 2004/0256584 A1 | 12/2004 | Zimmerling et al. | |
| 2004/0264293 A1 | 12/2004 | Laugharn, Jr. et al. | |
| 2005/0016605 A1 | 1/2005 | Sherman et al. | |
| 2005/0037075 A1 | 2/2005 | Farokhzad et al. | |
| 2005/0055014 A1 | 3/2005 | Coppeta et al. | |
| 2005/0096587 A1 | 5/2005 | Santini, Jr. et al. | |
| 2005/0119733 A1 | 6/2005 | Wiliams et al. | |
| 2005/0123563 A1 | 6/2005 | Doranz et al. | |
| 2005/0143802 A1 | 6/2005 | Soykan et al. | |
| 2005/0181366 A1 | 8/2005 | Ostermeier | |
| 2005/0187515 A1 | 8/2005 | Varrichio et al. | |
| 2005/0187677 A1 | 8/2005 | Walker | |
| 2005/0191194 A1 | 9/2005 | Falk et al. | |
| 2005/0191708 A1* | 9/2005 | Saul et al. | 435/7.1 |
| 2005/0192637 A1 | 9/2005 | Girouard et al. | |
| 2005/0234431 A1 | 10/2005 | Williams et al. | |
| 2005/0267440 A1 | 12/2005 | Herman et al. | |
| 2006/0004417 A1 | 1/2006 | Rossing et al. | |
| 2006/0089751 A1 | 4/2006 | Herbst | |
| 2006/0116641 A1 | 6/2006 | Gordon et al. | |
| 2006/0149321 A1 | 7/2006 | Merry et al. | |
| 2006/0201432 A1 | 9/2006 | Pratt | |
| 2006/0224128 A1 | 10/2006 | Lurvey et al. | |
| 2006/0241747 A1 | 10/2006 | Shaoulian et al. | |
| 2006/0283465 A1 | 12/2006 | Nickel et al. | |
| 2007/0016171 A1 | 1/2007 | Podvin et al. | |
| 2007/0074722 A1 | 4/2007 | Giroux et al. | |
| 2007/0078445 A1 | 4/2007 | Malloy | |
| 2007/0104023 A1 | 5/2007 | Hood et al. | |
| 2007/0106269 A1 | 5/2007 | Hood et al. | |
| 2007/0106270 A1 | 5/2007 | Hood et al. | |
| 2007/0106271 A1 | 5/2007 | Hood et al. | |
| 2007/0106281 A1 | 5/2007 | Hood et al. | |
| 2007/0135797 A1 | 6/2007 | Hood et al. | |
| 2007/0135798 A1 | 6/2007 | Hood et al. | |
| 2007/0135799 A1 | 6/2007 | Hood et al. | |
| 2007/0135800 A1 | 6/2007 | Hood et al. | |
| 2007/0135801 A1 | 6/2007 | Hood et al. | |
| 2007/0147170 A1 | 6/2007 | Hood et al. | |
| 2007/0149954 A1 | 6/2007 | Hood et al. | |
| 2009/0018704 A1 | 1/2009 | Hood et al. | |
| 2009/0024114 A1 | 1/2009 | Hood et al. | |
| 2009/0227988 A1 | 9/2009 | Wood, Jr. et al. | |

FOREIGN PATENT DOCUMENTS

| | | |
|---|---|---|
| WO | WO 03/049592 A2 | 6/2003 |
| WO | WO 2005/084273 A3 | 9/2005 |

OTHER PUBLICATIONS

"Artificial Muscle Research Institute"; University of New Mexico; Bearing dates of May 29, 2000 and Oct. 14, 2005, printed on Oct. 21, 2005; pp. 1-7; located at: http://www.unm.edu/~amri/.

Bagnato, Joshua D.; Eilers, Alanna L.; Horton, Robert A.; Grissom, Charles B.; "Synthesis and Characterization of a Cobalamin-Colchicine Conjugate as a Novel Tumor-Targeted Cytotoxin"; The Journal of Organic Chemistry; Bearing dates of 2004 and Jun. 3, 2004, printed on Oct. 21, 2005; pp. 8987-8996 (pp. 1-1); vol. 69, No. 26; American Chemical Society; located at: http://pubs.acs.org/cgi-bin/abstract.cgi/joceah/2004/69/i26/abs/jo049953w.html.

Boniface, J. Jay; Lyons, Daniel S.; Wettstein, Daniel A.; Allbritton, Nancy L.; Davis, Mark M.; "Evidence for a Conformational Change in a Class II Major Histocompatibility Complex Molecule Occuring in the Same pH Range Where Antigen Binding Is Enhanced"; J. Exp. Med.; Bearing dates of Jan. 1996 and Jun. 26, 2005; pp. 119-126; vol. 183; The Rockefeller University Press; located at: http://www.jem.org.

Chen, Haitao; Rosengart, Axel J.; Kaminski, Michael D.; Caviness, Patricia L.; Mertz, Carol J.; Balasubramanian, Viji; Ebner, Armin D.; Ritter, James A.; "Achieving and Optimizing Separation of Magnetic Carriers from Pulsatile Blood Flow"; pp. 1-1; Collaborative Investigators for Applied Nanotechnology in Medicine; located at: http://www.cmt.anl.gov/nanomedicine/posters/carrier-separation.pdf.

Chen, Haitao; Kaminski, Michael D.; Rosengart, Axel J.; Ebner, Armin D.; Guy, Sandra G.; Mertz, Carol J.; Caviness, Patricia L.; Ritter, James A.; "Magnetizable Intravascular Stent and Functionalized Magnetic Carriers: A Novel Approach for Noninvasive Yet Targeted Drug Delivery"; pp. 1-1; Collaborative Investigators for Applied Nanotechnology in Medicine; located at: http://www.cmt.anl.gov/nanomedicine/posters/stent.pdf.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; pp. 1-1; Collaborative Investigators for Applied Nanotechnology in Medicine; located at: http://cmtpub.cmt.anl.gov/nanomedicine/posters/sequestration.pdf.

(56) References Cited

OTHER PUBLICATIONS

Davison, Brian H.; Adams, M.W.W.; "Characterization of Chemically Modified Enzymes for Bioremediation Reactions"; Final Report: U.S. Department of Energy; Bearing dates of Sep. 22, 2000, Oct. 1, 1996 to Aug. 31, 2000; pp. 1-14.

Edelman, E.R.; Kost, J.; Bobeck, H.; Langer, R.; "Regulation of drug release from polymer matrices by oscillating magnetic fields"; Journal of Biomedical Materials Research; Bearing a date of 1985; pp. 67-83; vol. 19; John Wiley and Sons, Inc.

Edwards, David A.; Ben-Jebria, Abdelaziz; Langer, Robert; "Invited Review: Recent advances in pulmonary drug delivery using large, porous inhaled particles"; Journal of Applied Physiology; Bearing a date of 1998, downloaded on Oct. 12, 2005; pp. 379-385; vol. 84 (sic 85), Issue 2; The American Physiological Society; located at: http://jap.physiology.org.

Erion, Mark D.; Van Poelje, Paul D.; Mackenna, Deidre A.; Colby, Timothy J.; Montag, Annika C.; Fujitaki, James M.; Linemeyer, David L.; Bullough, David A.; "Absorption, Distribution, Metabolism, and Excretion: Liver-Targeted Drug Delivery Using HepDirect Prodrugs"; Journal of Pharmacology and Experimental Therapeutics *Fast Forward*; Bearing dates of Aug. 31, 2004 and 2005, printed on Oct. 21, 2005; pp. 1-2; Metabasis Therapeutics, Inc. and American Society for Pharmacology and Experimental Therapeutics; San Diego; located at: http://jpet.aspetjournals.org/cgi/content/abstract/312/2/554.

"Ferrofluids"; Liquidsresearch.com; Bearing a date of 2000, printed on Oct. 21, 2005; pp. 1-1; Liquids Research Limited; located at: http://www.liquidsresearch.com/products/ferro.asp.

"Ferromagnetic SMA Actuator"; MIDÉ; Bearing a date of 2004, printed on Aug. 11, 2005; pp. 1-2; Mide Technology Corporation; located at: http://www.mide.com/pdf_html/FSMAA.htm.

Grayson, Amy C. Richards; Shawgo, Rebecca S.; Johnson, Audrey M.; Flynn, Nolan T.; Li, Yawen; Cima, Michael J.; Langer, Robert; "A BioMEMS Review: MEMS Technology for Physiologically Integrated Devices"; Proceedings of the IEEE; Bearing dates of 2004 and Jan. 2004; pp. 6-21; vol. 92, No. 1; IEEE.

Grayson, Amy C. R.; Voskerician, Gabriela; Lynn, Aaron; Anderson, James M.; Cima, Michael J.; Langer, Robert; "Differential degradation rates in vivo and in vitro of biocompatible poly(lactic acid) and poly(glycolic acid) homo-and co-polymers for a polymeric drug-delivery microchip"; Journal of Biomaterials Science, Polymer Edition; Bearing a date of 2004; pp. 1281-1304; vol. 15, No. 10; VSP; located at: http://www.vsppub.com.

Grayson, Amy C. Richards; Choi, Insung S.; Tyler, Betty M.; Wang, Paul P.; Brem, Henry; Cima, Michael J.; Langer, Robert; "Multi-pulse drug delivery from a resorbable polymeric microchip device"; Nature Materials; Bearing dates of 2003 and Nov. 2003; pp. 767-772; vol. 2; Nature Publishing Group; located at: http://www.nature.com/naturematerials.

Gu, H; Ho, PL; Tsang, KW; Wang, L; Xu, B; "Using biofunctional magnetic nanoparticles to capture vancomycin-resistant enterococci and other gram-positive bacteria at ultralow concentration"; Journal of the American Chemical Society; Bearing dates of Dec. 24, 2003 and Oct. 18, 2005, printed on Oct. 21, 2005; pp. 15702-15703 (pp. 1-1); vol. 125, No. 51; PubMed; located at: http://www.ncbi.nlm.nih.gov/entrez/query.fcgi?cmd=Retrieve&db=PubMed&list_uids=14677934&dopt=Abstract.

Jacque, David; "Science and Technology: Magnetic Nanoparticles Eyed as Biohazard Treatment"; Argonne News; Bearing a date of Nov. 10, 2003, printed on Oct. 21, 2005; pp. 1-3; located at: http://www.cmt.anl.gov/science-technology/processchem/magnetic-nanoparticles.shtml.

Johnson, Audrey M.; Sadoway, Donald R.; Cima, Michael J.; Langer, Robert; "Design and Testing of an Impedance-Based Sensor for Monitoring Drug Delivery"; Journal of the Electrochemical Society; Bearing a date of 2005; pp. H6-H11; vol. 152, Issue 1; The Electrochemical Society, Inc.

Jonnalagadda, Sriramakamal; Robinson, Dennis H.; "A Bioresorbable, Polylactide Reservoir for Diffusional and Osmotically Controlled Drug Delivery"; AAPS PharmSciTech; Bearing a date of 2000; pp. 1-9; vol. 1, No. 4, Article 29; located at: http://www.pharmscitech.com/.

Kaminski, Michael D.; Rosengart, Axel J.; "Biohazard Detoxification Using Magnetic Nanoparticles"; Argonne National Laboratory and the University of Chicago; located at: http://www.cmt.anl.gov/science-technology/processchem/BiohazardDetoxification.pdf.

Knapp, Louise; "Ironing Out Blood Impurities"; Wired News; Bearing dates of Dec. 8, 2003 and 2005, printed on Oct. 21, 2005; pp. 1-4; Lycos, Inc.; located at: http://www.wired.com/news/print/0,1294,61505,00.html and http://www.wired.com/news/medtech/0,1286,61505,00.html.

Kohane, Daniel S.; Plesnila, Nikolaus; Thomas, Sunu S.; Le, Dean; Langer, Robert; Moskowitz, Michael A.; "Lipid-sugar particles for intracranial drug delivery: safety and biocompatibility"; Brain Research; Bearing a date of 2002; pp. 206-213; vol. 946; Elsevier Science B.V.; located at: http://www.elsevier.com/locate/bres.

Kost, Joseph; Wolfrum, Jackie; Langer, Robert; "Magnetically enhanced insulin release in diabetic rats"; Journal of Biomedical Materials Research; Bearing a date of 1987; pp. 1367-1373; vol. 21; John Wiley and Sons, Inc.

Kozhevnikov, Ivan V.; "Catalysts for Fine Chemical Synthesis, vol. 2, Catalysis by Polyoxometalates"; Chipsbooks.com; Bearing dates of 2002 and 1998-2006, printed on Oct. 21, 2005; pp. 1-3 (201 pages); vol. 2; Culinary and Hospitality Industry Publications Services; located at: http://www.chipsbooks.com/catcem2.htm.

Krauß, Robert; Liu, Mario; Reimann, Bert; Richter, Reinhard; Rehberg, Ingo; "Fluid pumped by magnetic stress"; Bearing a date of Jul. 1, 2004; pp. 1-3.

Krauß, Robert; Liu, Mario; Reimann, Bert; Richter, Reinhard; Rehberg, Ingo; "Fluid pumped by magnetic stress"; Bearing dates of Oct. 11, 2005 and Apr. 4, 2005; pp. 1-3; located at: http://arxiv.org/PS_cache/physics/pdf/0405/0405025.pdf.

Langer, Robert; Peppas, Nicholas A.; "Bioengineering, Food, and Natural Products: Advances in Biomaterials, Drug Delivery, and Bionanotechnology"; AIChE Journal; Bearing a date of Dec. 2003; pp. 2990-3006; vol. 49, No. 12.

Langer, Robert; "Biomaterials in Drug Delivery and Tissue Engineering: One Laboratory's Experience"; Accounts of Chemical Research; Bearing a date of 2000; pp. 94-101; vol. 33, No. 2; American Chemical Society.

Langer, Robert; "Commentary: Transdermal drug delivery: past progress, current status, and future prospects"; Advanced Drug Delivery Reviews; Bearing a date of 2004; pp. 557-558; vol. 56; Elsevier B.V.; located at: http://www.sciencedirect.com and http://www.elsevier.com/locate/addr.

Langer, Robert; "Perspectives: Drug Delivery: Drugs on Target"; Science; Bearing a date of Jul. 6, 2001; pp. 58-59; vol. 293; located at: http://www.sciencemag.org.

Langer, Robert; "Reviews: Drug Delivery and Targeting"; Nature: Therapeutic Horizons; Bearing a date of Apr. 30, 1998; pp. 4-10; vol. 392 Supplement, No. 6679.

Lavan, David A.; Lynn, David M.; Langer, Robert; "Perspectives: Moving smaller in drug discovery and delivery"; Nature Reviews: Drug Discovery; Bearing dates of 2001 and Jan. 2002; pp. 77-84; vol. 1; Macmillan Magazines Ltd; located at: http://www.nature.com/reviews/drugdisc.

Lavan, David A.; McGuire, Terry; Langer, Robert; "Small-Scale Systems for in vivo drug delivery"; Nature Biotechnology: Review; Bearing dates of 2003 and Oct. 2003; pp. 1184-1191; vol. 21, No. 10; Nature Publishing Group; located at: http://www.nature.com/naturebiotechnology.

"Lecture 9. Biochemistry 3521—Fordham University—1999"; BIFC 3521: Lecture; Bearing dates of Feb. 10, 1999 and 1999, printed on Oct. 24, 2005; pp. 1-11; located at: http://dwb.unl.edu/Teacher/NSF/C10/C10Links/www.fordham.edu/Biochem_3521/lect9/lect9.html.

Li, Yawen; Shawgo, Rebecca S.; Tyler, Betty; Henderson, Paul T.; Vogel, John S.; Rosenberg, Aron; Storm, Phillip B.; Langer, Robert; Brem, Henry; Cima, Michael J.; "In vivo release from a drug delivery MEMS device"; Journal of Controlled Release; Bearing dates of

(56) References Cited

OTHER PUBLICATIONS 2004 and Sep. 28, 2004; pp. 211-219; vol. 100; Elsevier B.V.; located at: http://www.sciencedirect.com and http://www.elsevier.com/locate/jconrel.
Lurie, Karen; "Instant Armor"; ScienCentral News; Bearing dates of Dec. 4, 2003, Oct. 21, 2005 and 2000-2005, printed on Oct. 21, 2005; pp. 1-3; ScienCentral, Inc.; Located at: http://www.sciencentral.com/articles/view.php3?article_id=218392121&language=english.
"Magnetorheological Fluids"; Liquidsresearch.com; Bearing a date of 2000, printed on Oct. 21, 2005; pp. 1-2; Liquids Research Limited; located at: http://www.liquidsresearch.com/products/magnet.asp.
Moses, Marsha A.; Brem, Henry; Langer, Robert; "Review: Advancing the field of drug delivery: Taking aim at cancer"; Cancer Cell; Bearing dates of 2003 and Nov. 2003; pp. 337-341; vol. 4; Cell Press.
Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.
"Our Technology"; Dynal Invitrogen Corporation; printed on Oct. 21, 2005; pp. 1-3; Dynal Biotech; located at: http://www.dynalbiotech.com/kunder/dynal/dynalpub401.nsf/($All)/A24F11400EF33100C1256EA60054D9C1?OpenDocument.
Paschke, R; Paetz, C; Mueller, T; Schmoll, HJ; Mueller H; Sorkau, E; Sinn, E; "Biomolecules linked to transition metal complexes—new chances for chemotherapy"; Current Medicinal Chemistry; Bearing dates of Oct. 2003 and Oct. 18, 2005, printed on Oct. 24, 2005; pp. 2033-2044 (pp. 1-2); vol. 10, No. 19; PubMed; located at: http://www.ncbi.nlm.nih.gov/entrez/query.fcgi?cmd=Retrieve&db=PubMed&list_uids=12871101&dopt=Abstract.
"Polymer Gel Actuators and Sensors"; web.mit.edu; pp. 1-5; located at: http://web.mit.edu/cmse/www/Leeb97.pdf.
Prausnitz, Mark R.; Mitragotri, Samir; Langer, Robert; "Reviews: Current Status and Future Potential of Transdermal Drug Delivery"; Nature Reviews: Drug Discovery; Bearing a date of Feb. 2004; pp. 115-124; vol. 3; located at: http://www.nature.com/reviews/drugdisc.
Puccetti, L; Fasolis, G; Vullo, D; Chohan, ZH; Scozzafava, A; Supuran, CT; "Carbonic anhydrase inhibitors. Inhibition of cytosolic/tumor-associated carbonic anhydrase isozymes I, II, IX, and XII with Schiff's bases incorporating chromone and aromatic sulfonamide moieties, and their zinc complexes"; Bioorganic & Medicinal Chemistry Letters; Bearing dates of Jun. 15, 2005 and Oct. 18, 2005, printed on Oct. 24, 2005; pp. 3096-3101 (pp. 1-2); vol. 15, No. 12; PubMed; located at: http://www.ncbi.nlm.nih.gov/entrez/query.fcgi?cmd=Retrieve&db=pub . . . .
"Research/Team 02: Project 2.4: Chemically-switchable magnetic materials for actuators"; MIT Institute for Soldier Nanotechnologies; printed on Oct. 21, 2005; pp. 1-2; located at: http://web.mit.edu/isn/research/team02/project02_04.html.
Robinson, Mark A.; Charlton, Stuart T.; Garnier, Philippe; Wang, Xiang-Tao; Davis, Stanley S.; Perkins, Alan C.; Frier, Malcolm; Duncan, Ruth; Savage, Tony J.; Wyatt, David A.; Watson, Susan A.; Davis, Benjamin G.; "Pharmacology: LEAPT: Lectin-directed enzyme-activated prodrug therapy"; PNAS; Bearing dates of Sep. 24, 2004, Oct. 5, 2004, and 2004, printed on Oct. 21, 2005; pp. 14527-14532 (pp. 1-16); vol. 101, No. 40; National Academy of Sciences; located at: http://www.pnas.org/cgi/content/full/101/40/14527.
Ross, Jennifer L.; Santangelo, Christian D.; Makrides, Victoria; Fygenson, D. Kuchnir; "Tau induces cooperative Taxol binding to microtubules"; PNAS; Bearing dates of Aug. 31, 2004 and 2004; pp. 12910-12915; vol. 101, No. 35; The National Academy of Sciences of the USA; located at: http://gabriel.physics.ucsb.edu/~deborah/pub/RossPNASv101p12910y04.pdf.
Safarik, Ivo; Safarikova, Mirka; "Magnetic techniques for the isolation and purification of proteins and peptides"; BioMagnetic Research and Technology; Bearing dates of 2004, Nov. 26, 2004 and 1999-2005, printed on Oct. 21, 2005; pp. 1-21; vol. 2, No. 7; BioMed Central Ltd.; located at: http://www.biomagres.com/content/2/1/7.
Santini, Jr., John T.; Richards, Amy C.; Scheidt, Rebecca; Lima, Michael J.; Langer, Robert; "Reviews: Microchips as Controlled Drug-Delivery Devices"; Angewandte Chemie International Edition; Bearing a date of 2000; pp. 2396-2407; vol. 39; Wiley-VCH.
Shahinpoor, M.; Bar-Cohen, Y.; Simpson, J.O.; Smith, J.; "Artificial Muscle Research Institute: Paper: Ionic Polymer-Metal Composites (IPMC) as Biomimetic Sensors, Actuators and Artificial Muscles—A Review"; University of New Mexico; printed on Oct. 21, 2005; pp. 1-28; located at: http://www.unm.edu/~amri/paper.html.
Shahinpoor, Mohsen; Kim, Kwang J; "Ionic polymer-metal composites: I. Fundamentals"; Smart Materials and Structures; Bearing dates of Aug. 7, 2001 and 2001; pp. 819-833; vol. 10; IOP Publishing Ltd; UK.
Shawgo, Rebecca S.; Voskerician, Gabriela; Linh Ho Duc, Hong; Li, Yawen; Lynn, Aaron; Macewan, Matthew; Langer, Robert; Anderson, James M.; Cima, Michael J.; "Repeated in vivo electrochemical activation and the biological effects of microelectromechanical systems drug delivery device"; Journal of Biomedical Materials Research; Bearing dates of 2004 and Oct. 26, 2004; pp. 559-568; vol. 71A; Wiley Periodicals, Inc; located at: http://www.interscience.wiley.com.
Sridhar, J; Wei, ZL; Nowak, I; Lewin, NE; Ayres, JA; Pearce LV; Blumberg, PM; Kozikowski, AP; "New bivalent PKC ligands linked by a carbon spacer: enhancement in binding affinity"; J Med Chem.; Bearing dates of Sep. 11, 2003 and Oct. 18, 2005, printed on Oct. 24, 2005; pp. 4196-4204 (pp. 1-2); vol. 46, No. 19; PubMed; Located at: http://www.ncbi.nlm.nih.gov/entrez/query.fcgi?cmd=Retrieve&db=PubMed&list_uids=12954072&dopt=Abstract.
Su, Yu-Chuan; Lin, Liwei; "A Water-Powered Micro Drug Delivery System"; Journal of Microelectromechanical Systems; Bearing dates of 2004 and Feb. 2004; pp. 75-82; vol. 13, No. 1; IEEE.
Voskerician, Gabriela; Shive, Matthew S.; Shawgo, Rebecca S.; Von Recum, Horst; Anderson, James M.; Cima, Michael J.; Langer, Robert; "Biocompatibility and biofouling of MEMS drug delivery devices"; Biomaterials; Bearing a date of 2003; pp. 1959-1967; vol. 24; Elsevier Science Ltd.; located at: http://www.sciencedirect.com and http://www.elsevier.com/locate/biomaterials.
Voskerician, Gabriela; Shawgo, Rebecca S.; Hiltner, P. Anne; Anderson, James M.; Cima, Michael J.; Langer, Robert; "In Vivo Inflammatory and Wound Healing Effects of Gold Electrode Voltammetry for MEMS Micro-Reservoir Drug Delivery Device"; IEEE Transactions on Biomedical Engineering; Bearing dates of 2004 and Apr. 2004; pp. 627-635; vol. 51, No. 4; IEEE.
Zrinyi, M.; Barsi, L.; Büki, A.; "Direct Observation of Discrete and Reversible Shape Transition in Magnetic Field Sensitive Polymer Gels"; printed on Oct. 21, 2005; pp. 1-6; located at: http://www.kfki.hu/~cheminfo/hun/olvaso/zrinyi/polymgel.html.
U.S. Appl. No. 11/521,076, Hood et al.
U.S. Appl. No. 11/505,259, Hood et al.
U.S. Appl. No. 11/482,097, Hood et al.
U.S. Appl. No. 11/474,068, Hood et al.
U.S. Appl. No. 11/450,159, Hood et al.
U.S. Appl. No. 11/372,492, Hood et al.
U.S. Appl. No. 11/372,226, Hood et al.
U.S. Appl. No. 11/335,911, Hood et al.
U.S. Appl. No. 11/335,788, Hood et al.
U.S. Appl. No. 11/335,786, Hood et al.
U.S. Appl. No. 11/335,785, Hood et al.
U.S. Appl. No. 11/302,450, Hood et al.
U.S. Appl. No. 11/302,407, Hood et al.
U.S. Appl. No. 11/302,449, Hood et al.
U.S. Appl. No. 11/302,321, Hood et al.
Shoji et al.; "Microflow devices and systems"; J. Micromech. Microeng.; bearing a date of 1994; pp. 157-171; vol. 4; IOP Publishing Ltd.
Japanese Examination Report; App. No. 2008-540179; Oct. 6, 2011; pp. 1-3; no translation provided.
UK Intellectual Property Office Examination Report Under Section 18(3); App. No. GB0809510.1; bearing a date of Oct. 27, 2010; pp. 1-2.
UK Intellectual Property Office Examination Report Under Section 18(3); App. No. GB0809489.8; bearing a date of Oct. 27, 2010; pp. 1-3.

(56) References Cited

OTHER PUBLICATIONS

UK Intellectual Property Office Examination Report Under Section 18(3); App. No. GB0809491.4; bearing a date of Oct. 27, 2010; pp. 1-2.
UK Intellectual Property Office Examination Report Under Section 18(3); App. No. GB0809498.9; Jan. 7, 2011 (received by our agent Jan. 13, 2011); 3 pages.
European Patent Office; Extended European Search Report; App. No. EP 06 82 7655; Mar. 11, 2013 (received by our Agent on Mar. 18, 2013); pp. 1-10.
UK Intellectual Property Office Examination Report Under Section 18(3); App. No. GB0809500.2; bearing a date of Jul. 29, 2011 (received by our agent on Aug. 4, 2011); pp. 1.
UK Intellectual Property Office Examination Report Under Section 18(3); App. No. GB0809510.1; bearing a date of Jul. 29, 2011 (received by our agent on Aug. 4, 2011); pp. 1.
UK Intellectual Property Office Examination Report Under Section 18(3); App. No. GB0809491.4; bearing a date of Aug. 4, 2011 (received by our agent on Aug. 4, 2011); pp. 1-2.
UK Intellectual Property Office Examination Report Under Section 18(3); App. No. GB0809487.2; bearing a date of Oct. 1, 2010 (received by our agent on Oct. 4, 2010); pp. 1-2.
UK Intellectual Property Office Examination Report Under Section 18(3); App. No. GB0809489.8; bearing a date of Jul. 25, 2011; pp. 1-2.
UK Intellectual Property Office Examination Report Under Section 18(3); App. No. GB0921925.4; Jun. 9, 2011 (received by our Agent on Jun. 13, 2011); pp. 1-5.
Hackworth, Martin; "Sound Waves I"; Idaho State University Department of Physics; printed on Sep. 9, 2014; 13 pages; located at http://www2.cose.isu.edu/~hackmart/soundwaveslengphys.pdf.

* cited by examiner

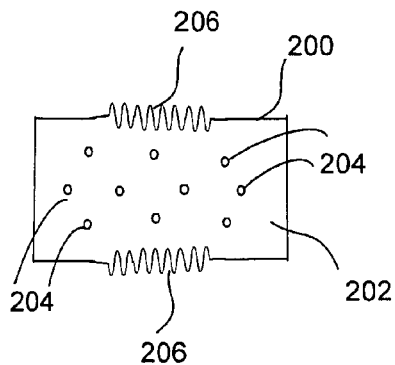
FIG. 9A
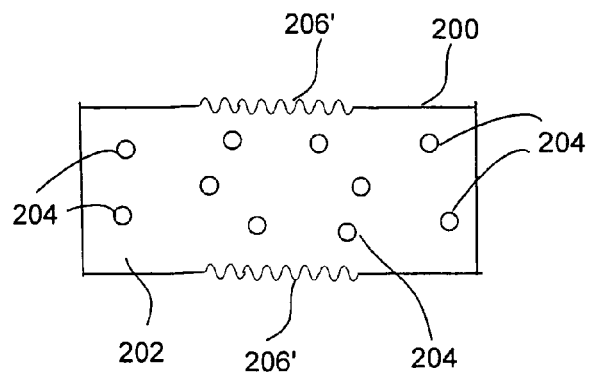
FIG. 9B
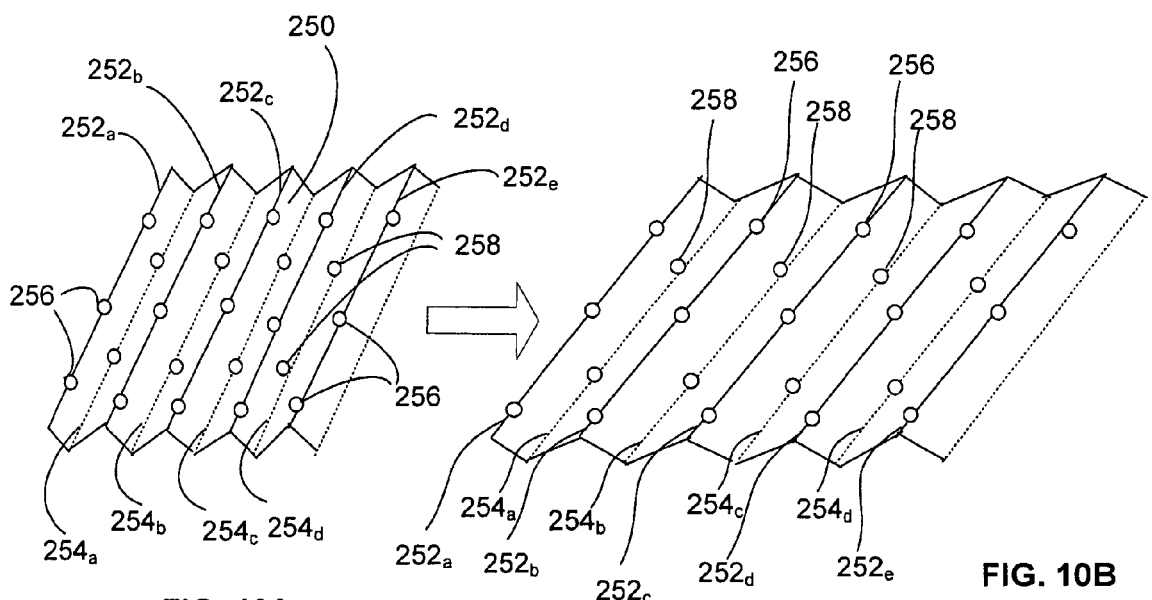
FIG. 10A
FIG. 10B
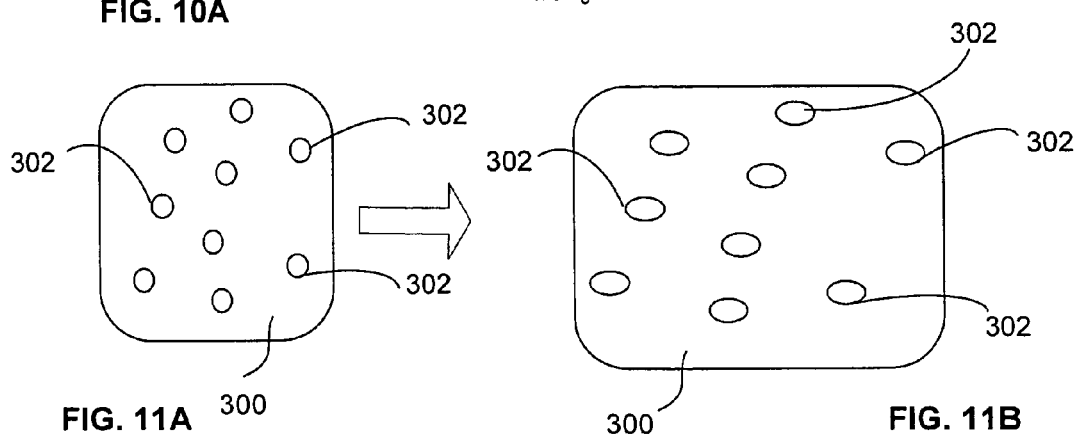
FIG. 11A
FIG. 11B

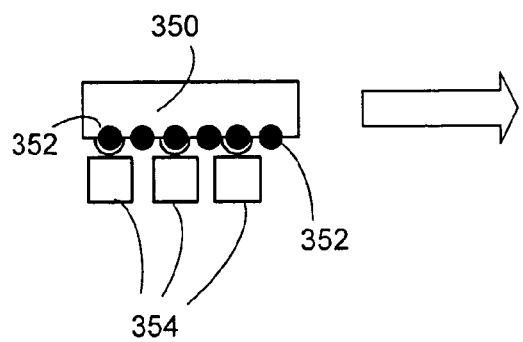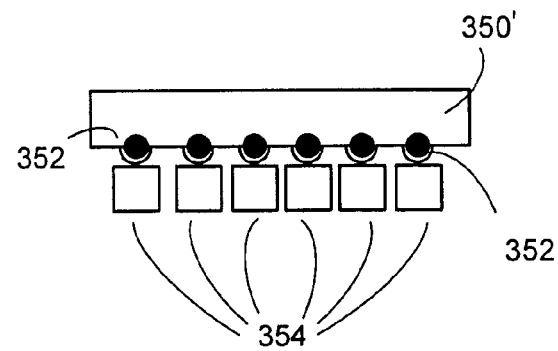
FIG. 12A  FIG. 12B
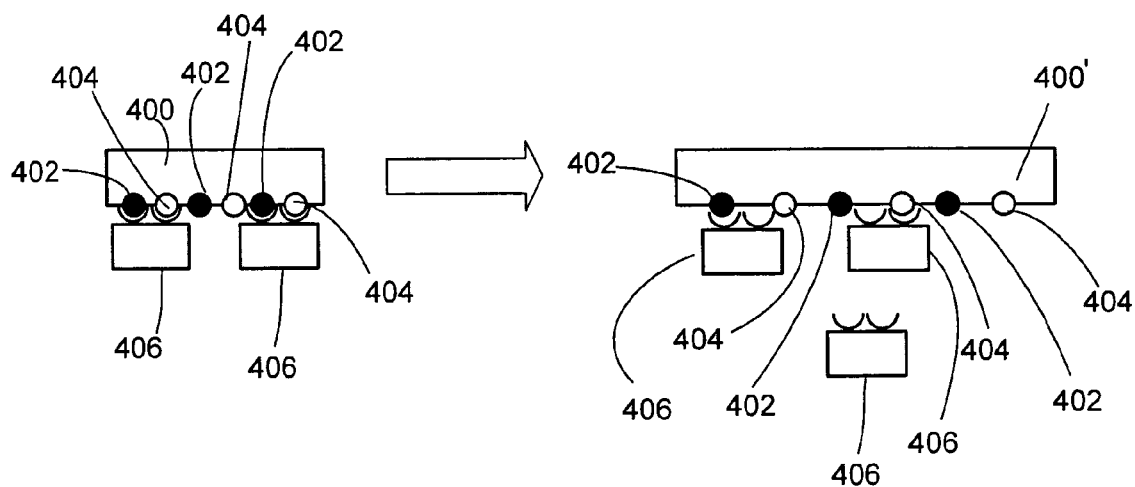
FIG. 13A  FIG. 13B

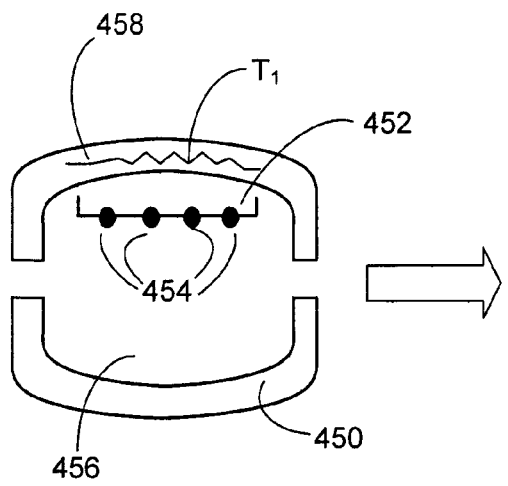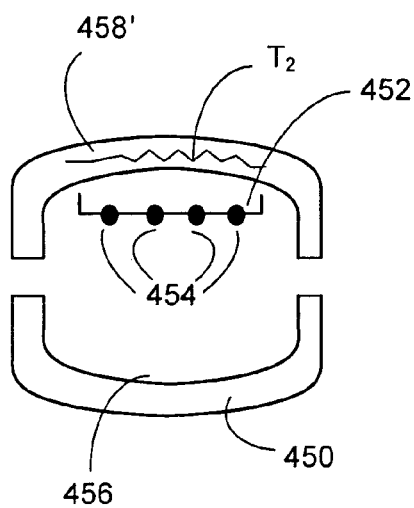
FIG. 14A  FIG. 14B
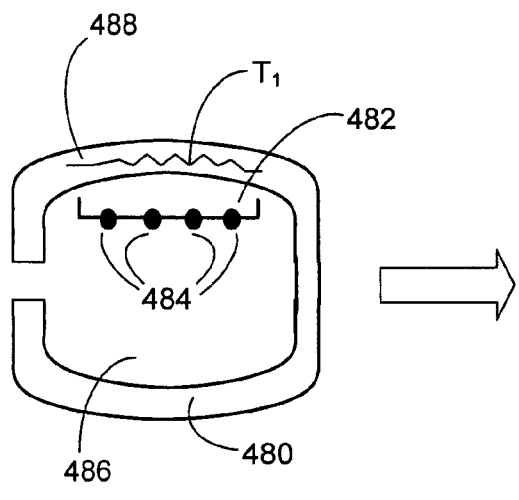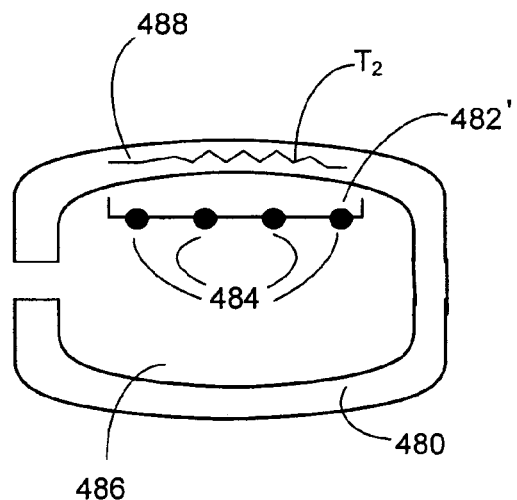
FIG. 15A  FIG. 15B

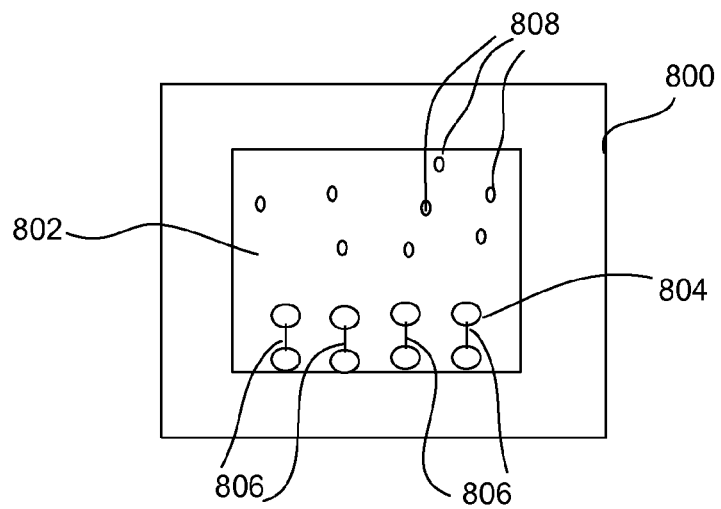
FIG. 23
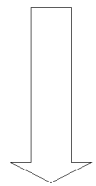
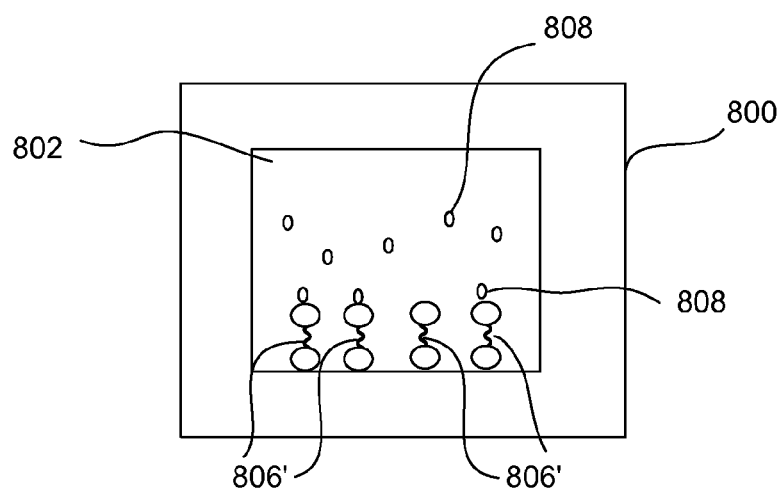
FIG. 24

Exposing functional group

REMOTE CONTROLLED IN SITU REACTION METHOD

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation-in-part of U.S. patent application Ser. No. 11/271,145, entitled REACTION DEVICE CONTROLLED BY MAGNETIC CONTROL SIGNAL, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/271,146, entitled REACTION DEVICE CONTROLLED BY RF CONTROL SIGNAL, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

3. For purposes of the USPTO extra-statutory requirements, the present application constitutes a continuation-in-part of U.S. patent application Ser. No. 11/272,524, entitled REMOTE CONTROLLED IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

4. For purposes of the USPTO extra-statutory requirements, the present application constitutes a continuation-in-part of U.S. patent application Ser. No. 11/272,455, entitled REMOTE CONTROLLER FOR IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

5. For purposes of the USPTO extra-statutory requirements, the present application constitutes a continuation-in-part of U.S. patent application Ser. No. 11/272,572, entitled REMOTE CONTROLLED IN VIVO REACTION METHOD, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

6. For purposes of the USPTO extra-statutory requirements, the present application constitutes a continuation-in-part of U.S. patent application Ser. No. 11/272,573, IN SITU REACTION DEVICE, naming Leroy E. Hood, Muriel Y. Ishikawa, Edward K. Y. Jung, Robert Langer, Clarence T. Tegreene, Lowell L. Wood, Jr. and Victoria Y. H. Wood as inventors, filed Nov. 9, 2005, which is currently co-pending, or is an application of which a currently co-pending application is entitled to the benefit of the filing date.

TECHNICAL FIELD

The present application relates, in general, to the field of devices, systems and/or methods for remotely affecting chemical or other reactions.

BACKGROUND

Implantable controlled release devices for drug delivery have been developed; certain devices rely upon the gradual release of a drug from a polymeric carrier over time, due to degradation of the carrier. Polymer-based drug release devices are being developed that include a drug in a ferropolymer that may be heated by an externally applied magnetic field, thus influencing the drug release. MEMS based drug release devices that include integrated electrical circuitry are also under development, as are MEMS based systems for performing chemical reactions. Wireless transmission of electromagnetic signals of various frequencies is well known in the areas of communications and data transmission, as well as in selected biomedical applications.

SUMMARY

The present application relates, in general, to the field of devices and systems for performing chemical reactions. In particular, the present application relates to remotely controlled reaction devices that make use of control signals carried between a remote controller and a reaction device in an environment by electrical, magnetic, or electromagnetic fields or radiation. Embodiments of a system including a remotely controlled reaction device and associated controller are described. Methods of use and control of the device are also disclosed. According to various embodiments, a reaction device is placed in an environment in order to perform a chemical reaction in an environment. Exemplary environments include a body of an organism, a body of water, or an enclosed volume of a fluid.

BRIEF DESCRIPTION OF THE FIGURES

FIGS. 9A and 9B depict expansion of a reaction volume;

FIGS. 10A and 10B depict unfolding of a pleated reaction region;

FIGS. 11A and 11B depict expansion of a porous element;

FIGS. 12A and 12B depict an example of the effect of stretching of a reaction region;

FIGS. 13A and 13B depict another example of an effect of stretching of a reaction region;

FIGS. 14A and 14B are cross-sectional views of an embodiment of a reaction device including a heating element;

FIGS. 15A and 15B are cross-sectional views of another embodiment of a reaction device including a heating element;

FIG. 23 illustrates an embodiment of a reaction device including remotely activatable molecules;

FIG. 24 illustrates the reaction device of FIG. 23 following excitation of the remotely activatable molecules;

DETAILED DESCRIPTION

Figure 1:
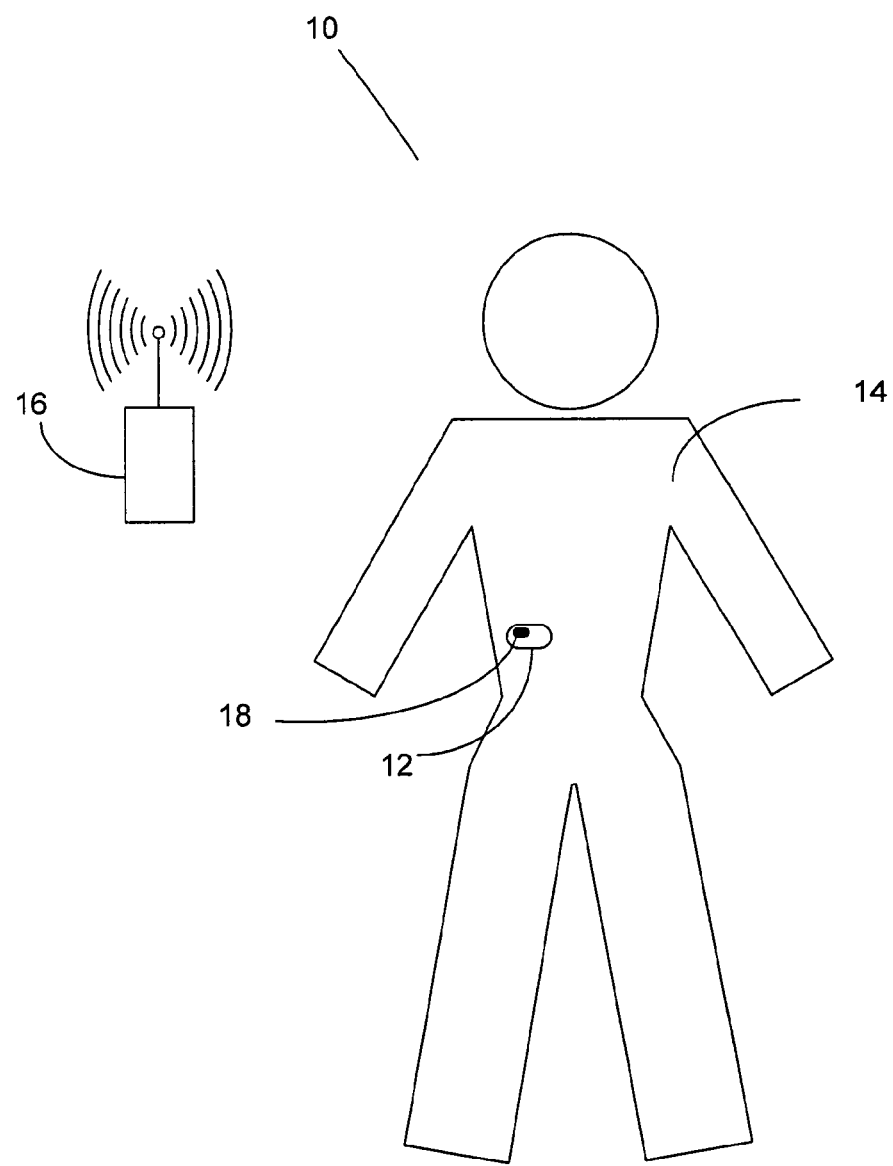
FIG. 1 illustrates an embodiment of a system including a remotely controlled reaction device.

FIG. 1 depicts a first exemplary embodiment of a reaction system 10. In the embodiment of FIG. 1, reaction system 10 includes reaction device 12 located in an environment 14, (which, in this particular example, is a human body) and remote controller 16. As used herein, the term "remote" refers to the transmission of information (e.g. data or control signals) or power signals or other interactions between the remote controller or the reaction system without a connecting element such as a wire or cable linking the remote controller and the reaction system, and does not imply a particular spatial relationship between the remote controller and the reaction device, which may, in various embodiments, be separated by relatively large distances (e.g. miles or kilometers) or a relatively small distances (e.g. inches or millimeters). Reaction device 12 includes a remotely activatable control element 18 that is responsive to an electromagnetic control signal generated by remote controller 16.

Figure 2:
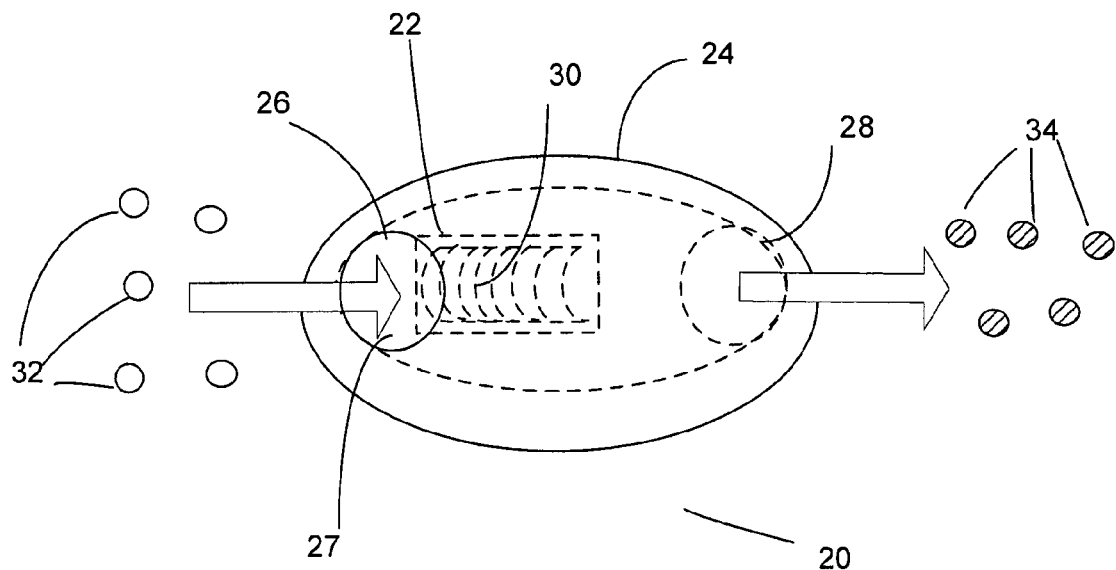
FIG. 2 depicts an embodiment of a reaction device including an internal reaction region.

An exemplary embodiment of a reaction device is depicted in FIG. 2. Reaction device 20 includes remotely activatable control element 22 in body structure 24. Body structure 24 includes inlet 26 which provides for the movement of materials (either by mass fluid flow or molecular diffusion) into an internal space 27, and outlet 28 which provides for movement of materials out of internal space 27. A reaction region 30 is located on an inner surface of reaction device 20. A reaction occurring at reaction region 30 may be modulated by the activity of remotely activatable control element 22. As an example, reactant molecules 32 may move into reaction device 20 and participate in a reaction at reaction region 30. Reaction product molecules 34 then exit reaction device 20 via outlet 28.

Figure 3:
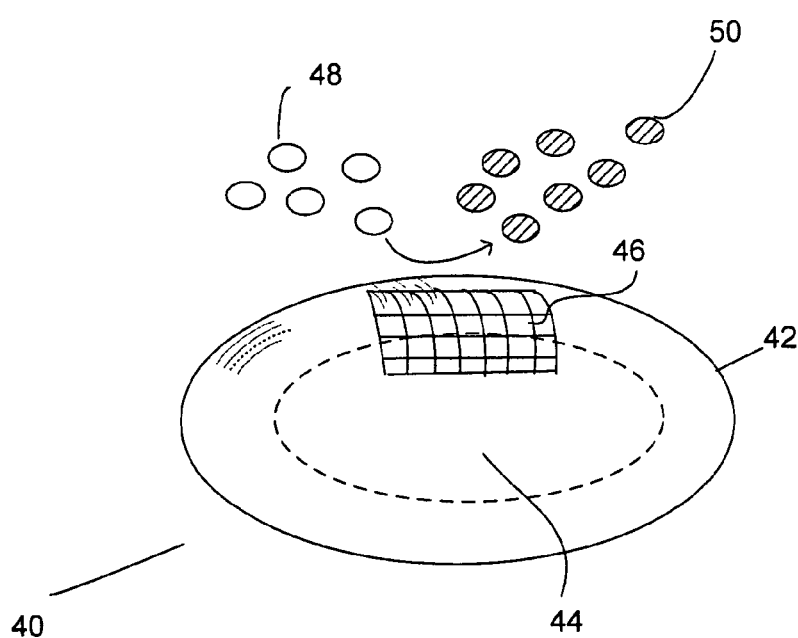
FIG. 3 depicts an embodiment of a reaction device including a reaction region on an exterior portion of a body structure.

While FIG. 2 depicts a reaction device 20 having a reaction region 30 within a body structure 24, FIG. 3 illustrates a reaction device 40 with a reaction region 46 located on an outer surface of a body structure 42. A remotely activatable control element 44 may be located within reaction device 40. Reactant molecules 48 undergo a reaction at reaction region 46, on the exterior of body structure 24, to form reaction product 50.

The body structure of the reaction device (e.g. body structure 24 in FIG. 2 or body structure 42 in FIG. 3) may be adapted for a specific environment. The size, shape, and materials of the body structure influence suitability for a particular environment. For example, a device intended for use in a body of a human or other organism should have suitable biocompatibility characteristics. For use in any environment, the body structure (and device as a whole) may be designed to withstand environmental conditions such as temperature, chemical exposure, and mechanical stresses. Moreover, the body structure may include features that allow it to be placed or positioned in a desired location in the environment, or targeted to a desired location in the environment. Such features may include size and shape features, tethers or gripping structures to prevent movement of the body structure in the environment (in the case that the device is placed in the desired location) or targeting features (surface chemistry, shape, etc.) that may direct the device toward or cause it to be localized in a desired location. Small devices (e.g. as may be used for placement in the body of an organism) may be constructed using methods known to those in skill of the art of microfabrication. In applications where size is not a constraint, a wide variety of fabrication methods may be employed.

Figure 4:
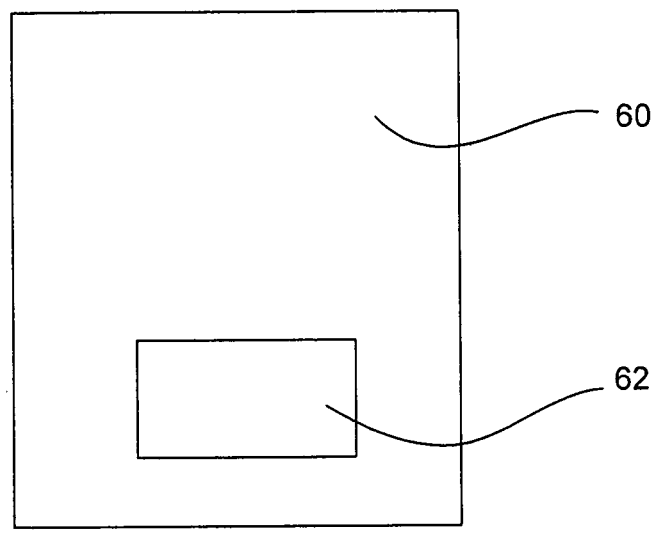
FIG. 4 depicts an embodiment of a remotely activatable control element.

In some embodiments, a remotely activatable control element may be formed entirely of a magnetically or an electrically responsive material or structure. In other embodiments, a remotely activatable control element may include multiple magnetically or electrically responsive components (e.g. ferrous particles). In some embodiments, as depicted in FIG. 4 in schematic form, a remotely activatable control element 60 may include a magnetically or electrically active component 62 which forms only a part of the magnetically or electrically responsive control element.

Reaction systems as depicted in FIG. 1 may include, for example, a reaction device as exemplified in FIG. 2, including a body structure 24 adapted for positioning in a body of an organism, a reaction region 30 located in or on the body structure, the reaction region including a first material capable of influencing a chemical reaction; and a remotely activatable control element 22 operably coupled to the body structure and responsive to an electromagnetic field control signal to modify one or more of the rate or kinetics of the chemical reaction. A reaction system may also include a remote control signal source (16 in FIG. 1) capable of generating an electromagnetic control signal sufficient to activate the remotely activatable control element to produce a desired rate or kinetics of the chemical reaction.

Figure 5:
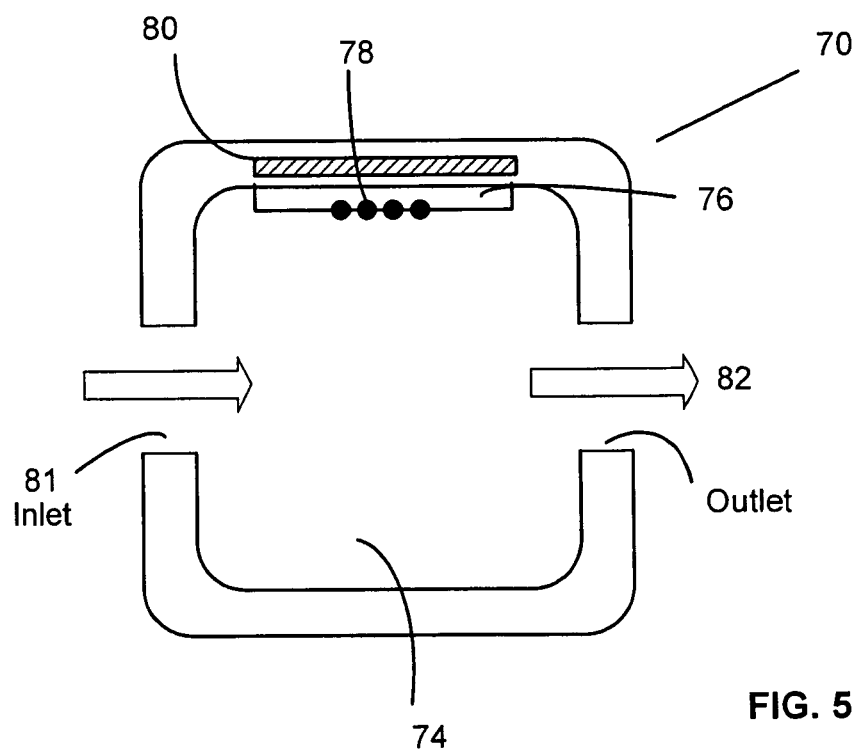
FIG. 5 is a cross-sectional view of a reaction device.

The reaction region of the reaction device may be located in an interior portion of the body structure and may be at least intermittently in fluid communication with the environment via at least one inlet or outlet, as depicted in FIG. 2. The operation of the reaction device will be described in greater detail in connection with FIG. 5. FIG. 5 is a cross sectional view of a reaction device 70 of the same general type as shown in FIG. 2, including a body structure 72 having an inlet 81 and outlet 82 and enclosing a reaction volume 74. A reaction region 76 includes a first material 78 that is capable of influencing a chemical reaction. Remotely activatable control element 80 is responsive to an electromagnetic control signal to modify the influence of first material 78 on a chemical reaction. Alternatively, in some embodiments, the reaction region may be located on an exterior portion of the body structure in fluid communication with the environment, as depicted in FIG. 3. As will be described in greater detail herein, reaction device 70 may further include a valve responsive to a change in at least one dimension of the remotely activatable control element. The valve may be configured to modify the flow of fluid into the reaction region responsive to the change in at least one dimension of the remotely activatable control element. Additional portions of the reaction region may be exposed responsive to the change in at least one dimension of the remotely activatable control element. A surface area of the reaction region may be modified responsive to the change in at least one dimension of the remotely activatable control element, or a volume of a reaction space containing the reaction region within the interior portion of the body structure may be modified responsive to the change in at least one dimension of the remotely activatable control element.

Figure 6:
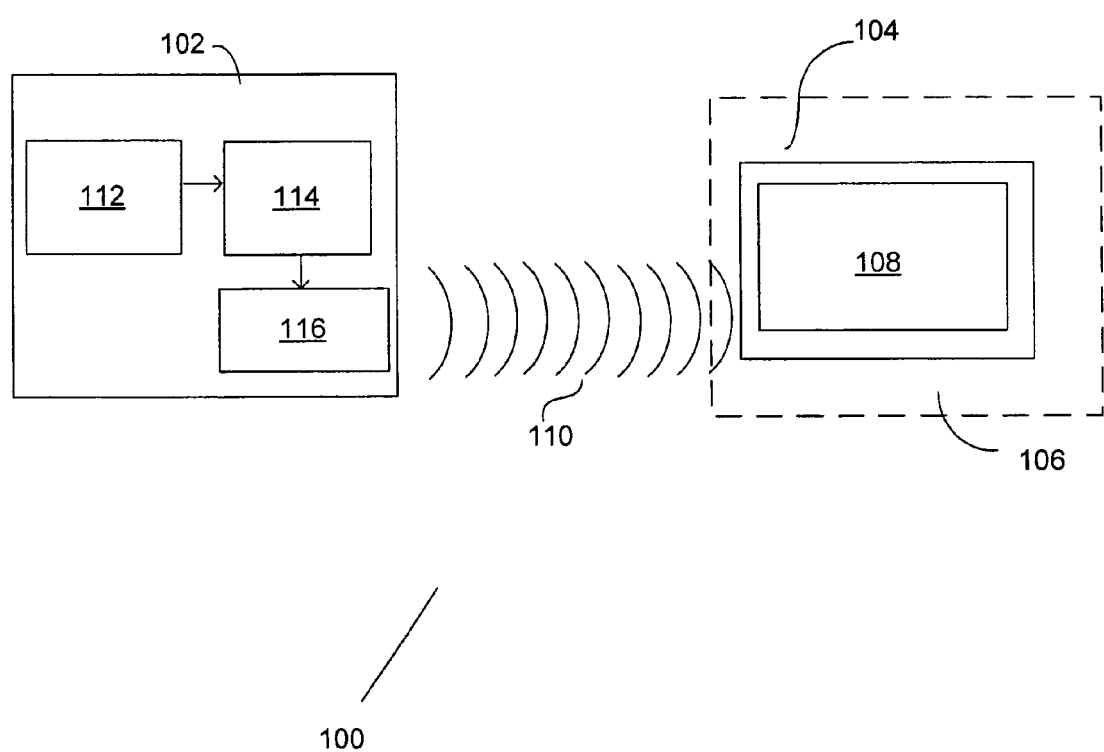
FIG. 6 depicts an embodiment of a system including a remote control device and a release device.

FIG. 6 depicts a reaction system 100 including an exemplary remote controller or remote control signal source 102 and a reaction device 104. Reaction device 104 is positioned in an environment 106, and includes remotely activatable control element 108. Remotely activatable control element 108 is responsive to an electromagnetic control signal 110 produced by remote control signal source 102. Remote control signal source 102 may include electrical circuitry 112, a signal generator 114, and a signal transmitter 116. Signal transmitter 116 may include a sending device which may be, for example, an antenna or waveguide suitable for use with an electromagnetic signal. Static and quasistatic electrical fields may be produced, for example, by charged metallic surfaces, while static and quasistatic magnetic fields may be produced, for example, by passing current through one or more wires or coils, or through the use of one or more permanent magnets, as known to those of skill in the art. As used herein, the terms transmit, transmitter, and transmission are not limited to only transmitting in the sense of radiowave transmission and reception of electromagnetic signals, but are also applied to wireless coupling and/or conveyance of magnetic signals from one or more initial locations to one or more remote locations.

The remote control signal source (as depicted generally in FIG. 6) may be configured to produce an electromagnetic control signal having various characteristics, depending upon the intended application of the system. Design specifics of circuitry 112, signal generator 114, and signal transmitter 116 will depend upon the type of electromagnetic control signal 110; the design of circuitry and related structures for generation and transmission of electromagnetic signals can be implemented using tools and techniques known to those of skill in the electronic arts. See, for example, Electrodynamics of Continuous Media, $2^{nd}$ Edition, by L. D. Landau, E. M. Lifshitz and L. P. Pitaevskii, Elsevier Butterworth-Heinemann, Oxford, pp. 1-13- and 199-222, which is incorporated herein by reference, for discussion of theory underlying the generation and propogation of electrical, magnetic, and electromagnetic signals.

In some embodiments, a specific remote control signal source may be configured to produce only a specific type of signal (e.g., of a specific frequency or frequency band) while in other embodiments, a specific remote control signal source may be adjustable to produce a signal having variable frequency content. The remote control signal source 102 of the reaction system 100 may be configured to generate a static or quasi-static electrical field control signal or static or quasi-static magnetic field control signal sufficient to activate a remotely activatable control element 108 to produce a desired rate or kinetics of the chemical reaction. In other embodiments, the remote control signal source 102 may be configured to generate an electromagnetic control signal at various different frequencies sufficient to activate the remotely activatable control element 108 to produce a desired rate or kinetics of the chemical reaction. Electromagnetic control signals may have radio-frequency, microwave, infrared, millimeter wave, optical, or ultraviolet frequencies, for example. Generation of radio frequency electromagnetic signals is described, for example, in the *The ARRL Handbook for Radio Communications* 2006, R. Dean Straw, Editor, published by ARRL, Newington, Conn., which is incorporated herein by reference.

The remote controller/remote control signal source (e.g., 102 in FIG. 6) may be modified as appropriate for its intended use. For example, it may be configured to be wearable on the body of a human (or other organism) in which a reaction device has been deployed, for example on a belt, bracelet or pendant, or taped or otherwise adhered to the body of the human. Alternatively, it may be configured to be placed in the surroundings of the organism, e.g. as a table-top device for use in a home or clinical setting.

Various types of electromagnetic field control signals may be used to activate the remotely activatable control element. The remotely activatable control element may be responsive to a static or quasi-static electrical field or a static or quasi-static magnetic field. It may be responsive to various types of non-ionizing electromagnetic radiation, or in some cases, ionizing electromagnetic radiation. Electromagnetic field control signals that may be used in various embodiments include radio-frequency electromagnetic radiation, microwave electromagnetic radiation, infrared electromagnetic radiation, millimeter wave electromagnetic radiation, optical electromagnetic radiation, or ultraviolet electromagnetic radiation.

In some embodiments, the remotely activatable control element may respond to the control signal by changing shape. In some embodiments, the remotely activatable control element may respond to the control signal by changing in at least one dimension. The response of the remotely activatable control element may include one or more of heating, cooling, vibrating, expanding, stretching, unfolding, contracting, deforming, softening, or folding globally or locally. The remotely activatable control element may include various materials, such as polymers, ceramics, plastics, dielectrics or metals, or combinations thereof. The remotely activatable control element may include a shape memory material such as a shape memory polymer or a shape memory metal, or a composite structure such as a bimetallic structure. The remotely activatable control element may include a magnetically or electrically active material. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics. In some embodiments, the remotely activatable control element may include a hydrogel or a ferrogel.

In some embodiments, the remotely activatable control element may include a polymer and an electrically active component (including highly polarizable dielectrics) or a magnetically active component (including ferropolymers and the like as well as remotely activatable control elements include one (or possibly more) large magnetically or electrically active components, as depicted in FIG. 4. In embodiments in which the remotely activatable control element includes one or more electrically or magnetically active components, the electrically or magnetically active component may respond to an electromagnetic control signal in a first manner (e.g., by heating) and the response of the remotely activatable control element may be produced in response to the electrically or magnetically active component (e.g. expansion or change in shape in response to heating of the electrically or magnetically active component).

Figure 7:
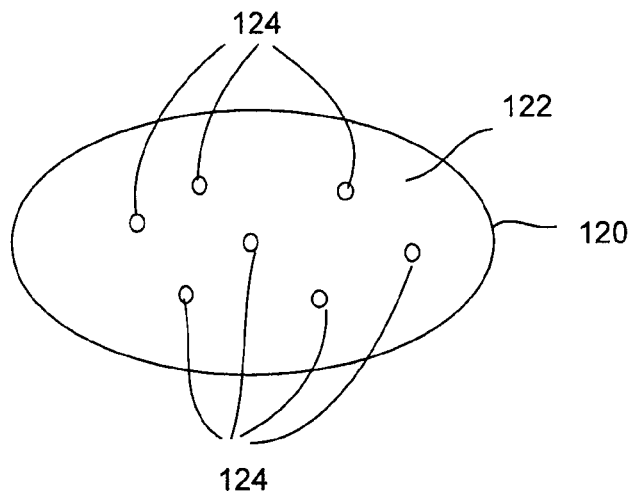
FIG. 7 depicts a remotely activatable element including a plurality of electromagnetically active elements.

An exemplary remotely activatable control element 120 including a composite structure formed from a polymer 122 and multiple electrically or magnetically active components in the form of multiple particles 124 distributed through the polymer 122 is depicted in FIG. 7. In some embodiments, the remotely activatable control element may be comprised entirely of a electrically or magnetically active structure. For example, the electrically or magnetically active component may be heatable by the incident electromagnetic control signal, and wherein heating of the electrically or magnetically active component causes the polymer to undergo a change in configuration that modifies the influence of the first material on the chemical reaction. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5 or U.S. Pat. No. 6,607,553, both of which are incorporated herein by reference.

In some embodiments, the remotely activatable control element may form a structural component of the reaction device that modifies the rate or kinetics of the reaction occurring at the reaction region by modifying a property of the reaction region or the space in which the reaction region is located. A structural component may include, for example, a portion of the wall of the reaction device or other portion (or possibly, the whole) of the structure of the device. Such effects may be produced through a change in at least one dimension by the remotely activatable control element in response to the control signal.

Figure 8A:
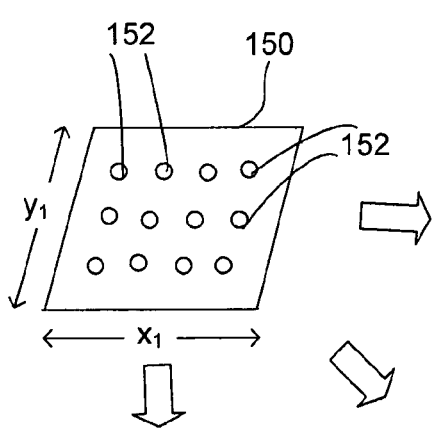
FIG. 8A depicts an exemplary reaction region.
Figure 8B:
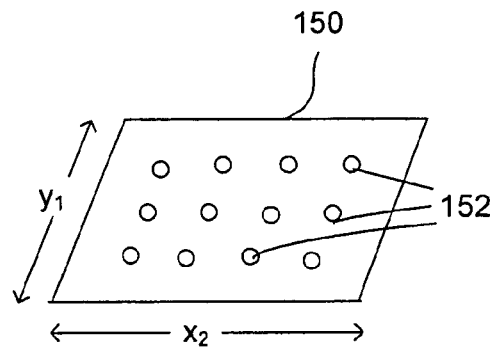
FIG. 8B depicts expansion of the reaction region of FIG. 8A in a first direction.
Figure 8C:
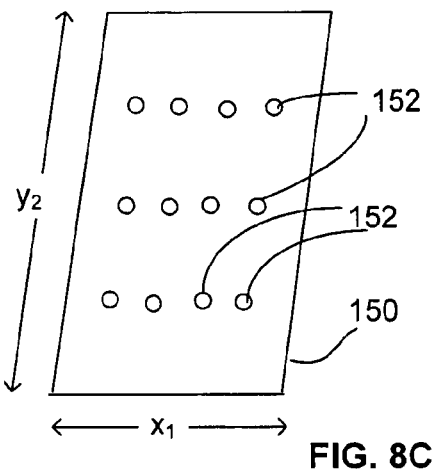
FIG. 8C depicts expansion of the reaction region of FIG. 8A in a second direction.
Figure 8D:
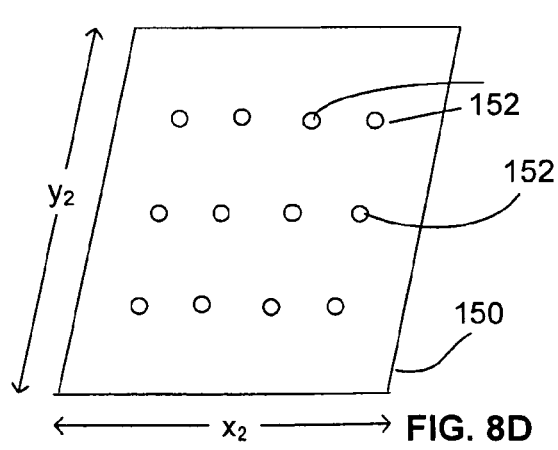
FIG. 8D depicts expansion of the reaction region of FIG. 8A in first and second directions.

FIGS. 8A-8D depict the effect of changes in one or two dimensions on a reaction region 150. For example, the reaction region may be formed on a remotely activatable control element that expands in response to a control signal, or it may expand in response to a response of a remotely activatable control element. A reaction region 150 including a plurality of reaction sites 152, and having initial length of $x_1$ in a first dimension and $y_1$ in a second dimension. FIG. 8B depicts reaction region 150 following a change in the first dimension, to a length $x_2$. FIG. 8C depicts reaction region 150 following a change in the second dimension, to a length $y_2$, and FIG. 8D depicts a change in both the first and second dimensions, to a size of $x_2$ by $y_2$. In each case, a change in dimension results in a change in distance between reaction sites 152. The dimension change depicted in FIGS. 8A-8D may be viewed as a 'stretching' or 'expansion' of the reaction region. Increasing the surface area of the reaction region may increase the rate of the reaction. Increasing the surface area of the reaction region (e.g., by stretching the surface) may increase the distance between reaction sites on the reaction region. An increased distance between reaction sites may lead to an increase in reaction rate (for example, in cases where smaller spacing between reaction sites leads to steric hindrance that blocks access of reactants to reaction sites).

Some examples of reactions that may be sped up by change in distance between reaction sites include those involving drugs designed with spacers, such as dual function molecules, biomolecules linked to transition metal complexes as described in Paschke et al, "Biomolecules linked to transition metal complexes—new chances for chemotherapy"; Current Medicinal Chemistry; bearing dates of October 2003 and Oct. 18, 2005, printed on Oct. 24, 2005; pp. 2033-44 (pp. 1-2); Volume 10, Number 19; PubMed, and Schiff bases as described in Puccetti et al., "Carbonic anhydrase inhibitors", Bioorg. Med. Chem. Lett. 2005 Jun. 15; 15(12): 3096-101 (Abstract only), both of which are incorporated herein by reference. Other reactions include reactions responding to conformational (allosteric) changes including regulation by allosteric modulators, and reactions involving substrate or ligand cooperativity in multiple-site proteins, where binding affects the affinity of subsequent binding, e.g., binding of a first $O_2$ molecule to Heme increases the binding affinity of the next, or influence of Tau on Taxol, as described in Ross et al., "Tau induces cooperative Taxol binding to microtubules"; PNAS; Bearing dates of Aug. 31, 2004 and 2004; pp. 12910-12915; Volume 101, Number 35; The National Academy of Sciences of the USA, which is incorporated herein by reference. Reactions that may be slowed down by increased reaction site spacing include reactions responsive to conformational (allosteric) changes, influence or pH, crosslinking. See for example Boniface et al., "Evidence for a Conformational Change in a Class II Major Histocompatibility Complex Molecule Occuring in the Same pH Range Where Antigen Binding Is Enhanced"; J. Exp. Med.; Bearing dates of January 1996 and Jun. 26, 2005; pp. 119-126; Volume 183; The Rockefeller University Press also incorporated herein by reference or Sridhar et al., "New bivalent PKC ligands linked by a carbon spacer: enhancement in binding affinity"; J Med Chem.; Bearing dates of Sep. 11, 2003 and Oct. 18, 2005, printed on Oct. 24, 2005; pp. 4196-204 (pp. 1-2); Volume 46, Number 19; PubMed (Abstract), also incorporated herein by reference.

In other embodiments, expansion of a remotely activatable control element may produce other modifications to a chemical reaction. For example, a volume of a reaction space containing the reaction region may be increased, as depicted in FIGS. 9A and 9B. A reaction device 200 includes a reaction space 202 containing reactant materials 204 and having a first volume in FIG. 9A. A remotely activatable control element 206 forms an expandable portion of the wall of reaction device 200. Upon expansion of remotely activatable control element to expanded form 206' shown in FIG. 9B the volume of reaction space 202 is increased. The concentration of reactant materials 204 within reaction space 202 is thus decreased, which may have a corresponding influence on the rate or kinetics of the reaction in which reactant material 204 participates. Similarly, while the increased volume may directly impact concentration of the reactant materials 204, where the space contains compressible fluids, driving a change in volume may produce corresponding changes in pressure or temperature according to conventional considerations of the relationships of pressure, volume, and temperature, which may in turn influence a chemical reaction. For example, for a compressible fluid such as an ideal gas, the relationship may be defined by the ideal gas law, $PV=nRT$.

In addition to increasing surface areas or reaction volumes, expansion of a remotely activatable control element may also have the effect of exposing additional portions of a reaction region or exposing additional functional group to influence a reaction condition. Increasing the surface area of the reaction region by unfolding or other forms of 'opening' of the reaction region structure of at least a portion of the reaction area may increase the number of reaction sites on the reaction region (e.g. by exposing additional reaction sites that were fully or partially hidden or obstructed when the reaction region was in a folded configuration). For example, the area of a reaction region may be increased by the unfolding of at least a portion of the reaction area to expose additional portions of the reaction area, as depicted in FIGS. 10A and 10B. In FIG. 10A, a reaction region 250, which includes or is made up of a remotely activatable control element can be expanded by unfolding to the form depicted in FIG. 10B. Reaction region 250 has a pleated structure that includes ridges 252a-252e and valleys 254a-254d. Reaction sites 256 may be located in or on ridges 252a-252e and valleys 254a-254d. In the folded form illustrated in FIG. 10A, reaction sites 256 located in valleys 254a-254d are 'hidden' in the sense that reactants may not fit into the narrow valleys to approach those reaction sites, while reaction sites on ridges 252a-252e remain exposed. When reaction region 250 is unfolded to the form shown in FIG. 10B, reaction sites 256 in valleys 254a-256d are exposed, because the open valleys permit access of reactants to the reaction sites in the valleys. Examples of materials that unfold in response to electromagnetic fields include ionic polymer-metal composites (IPMC) as described in Shahinpoor et al., "Artificial Muscle Research Institute: Paper: Ionic Polymer-Metal Composites (IPMC) As Biomimetic Sensors, Actuators and Artificial Muscles-A Review"; University of New Mexico; printed on Oct. 21, 2005; pp. 1-28, which is incorporated herein by reference.

A related modification of the reaction region, as depicted generally in FIGS. 11A-11B, may include an increase in porosity or decrease in density of a remotely activatable control element 300. Remotely activatable control element 300 is depicted in its unexpanded state in FIG. 11A, with multiple pores 302 of a first size; FIG. 11B illustrates the expanded form of remotely activatable control element 300, in which pores 302 have increased in size. Increase in porosity as depicted in FIGS. 11A and 11B may have a similar effect to the unfolding depicted in FIGS. 10A and 10B with respect to modifying the spacing or exposure of reaction sites, functional groups, etc. See, for example U.S. Pat. Nos. 5,643,246, 5,830,207, and 6,755,621, all of which are incorporated herein by reference.

The effects illustrated in FIGS. 8A-8D, 9A-9B, 10A-10B, and 11A-11B may be reversed by suitable adjustment to the control signal, leading to corresponding decrease in reaction region surface area, volume of the reaction space, or number of exposed reaction sites.

The influence of modifying the surface area of a reaction region is described further in connection with FIGS. 12A and 12B and 13A and 13B. FIGS. 12A and 12B illustrate how an increase of the surface area of a reaction region by stretching or expansion may increase the rate of the reaction occurring at the reaction region. Multiple reaction sites 352 are located in reaction region 350. As shown in FIG. 12A, prior to stretch or expansion, reaction sites 352 are close together, and reactant 354, which binds to the reaction sites 352 is sufficiently large that it is not possible for a reactant 354 to bind to each reaction site 352. When the reaction region has been stretched or expanded to expanded form 350' as depicted in FIG. 12B, so that the reaction sites 352 are further apart, it is possible for reactant 354 to bind to a larger percentage of the reaction sites, thus increasing the rate of reaction.

In other embodiments, an increase in the surface area of the reaction region by stretching or expansion may decrease the reaction rate (for example, in cases where a particular spacing is needed to permit binding or association of reactants with several reaction sites simultaneously). FIGS. 13A and 13B illustrate how an increase in the surface area of a reaction region 400 by stretching or expansion may decrease the rate of the reaction occurring at the reaction region. Again, multiple reaction sites 402 and 404 are located in the reaction region 400, as depicted in FIG. 13A. In the present example binding of a reactant to the reaction region 400 requires binding of a reactant 406 to two reaction sites 402 and 404. When reaction region is stretched or expanded to expanded form 400' as depicted in FIG. 13B, the spacing of the two reaction sites 402 and 404 is changed so that reactant 406 does not readily bind to reaction region 400', thus reducing the rate of reaction.

Accordingly, increasing the surface area of the reaction region may decrease the rate of the reaction in some circumstance and increase the rate of reaction in others. Exposure of additional portions of the reaction region may expose additional functional groups that are not reaction sites, but that may produce some local modification to a surface property of the reaction region that in turn modifies the rate or kinetics of the reaction. For example, exposed functional groups may produce at least a local change in pH, surface energy, or surface charge. See, for example, U.S. patent publication 2003/0142901 A1, which is incorporated herein by reference.

As noted herein, a remotely activatable control element may respond to the control signal by producing or by absorbing heat. In some embodiments, a change in temperature of the remotely activatable control element may modify the rate of a reaction directly. FIG. 14A depicts an embodiment of a reaction device 450 including a reaction region 452 in a reaction space 456. A first material 454 capable of influencing a reaction is located at reaction region 452. A remotely activatable control element 458 is located in the wall of reaction device in the vicinity of reaction region 452. Remotely activatable control element 458 has an initial temperature $T_1$. Following heating of remotely activatable control element 458 in response to an electromagnetic control signal, remotely activatable control element 458' has a subsequent temperature $T_2$, as shown in FIG. 14B. The change in temperature of remotely activatable control element 458' may modify the rate of reaction within reaction device 450 by modifying the temperature at one or both of reaction region 452 and reaction space 456.

Many materials expand when thermal energy is applied. By combining materials as in polymer gels one can use the differing properties of individual components to affect the whole. Thermally-responsive materials include thermally responsive gels (hydrogels) such as thermosensitive N-alkyl acrylamide polymers, Poly(N-isopropylacrylamide) (PNIPAAm), biopolymers, crosslinked elastin-based networks, materials that undergo thermally triggered hydrogelation, memory foam, resin composites, thermochromic materials, proteins, memory shape alloys, plastics, and thermoplastics. Materials that contract or fold in response to heating may include thermally-responsive gels (hydrogels) that undergo thermally triggered hydrogelation (e.g. Polaxamers, uncross-linked PNIPAAm derivatives, chitosan/glycerol formulations, elastin-based polymers), thermosetting resins (e.g. phenolic, melamine, urea and polyester resins), dental composites (e.g. monomethylacrylates), and thermoplastics.

A remotely activatable control element may respond to a control signal by producing cooling, either directly or indirectly, which may in turn modify the rate, kinetics, or other feature of a reaction. Cooling may be produced by a number of mechanisms and/or structures. For example, cooling may be produced by an endothermic reaction (such as the mixing of ammonium nitrate and water) initiated by opening of a valve or bursting of a container in response to an electromagnetic control signal. Other methods and/or mechanisms of producing cooling may include, but are not limited to, thermoelectric (Peltier Effect) and liquid-gas-vaporization (Joule-Thomson) devices.

In some embodiments, a change in temperature of a remotely activatable control element may modify the rate or other parameter of a reaction indirectly. FIG. 15A depicts an embodiment of a reaction device 480 including a reaction region 482 in a reaction space 486. A first material 484 capable of influencing a reaction is located at reaction region 482. A remotely activatable control element 488 is located in the wall of reaction device in the vicinity of reaction region 482. Remotely activatable control element 488 has an initial temperature $T_1$. Following heating of remotely activatable control element 488 in response to an electromagnetic control signal, remotely activatable control element 488 has a subsequent temperature $T_2$, as shown in FIG. 15B. Heating of remotely activatable control element 488 from $T_1$ to $T_2$ by a magnetic or electric or electromagnetic field or radiation, may in turn cause an expansion or other modification of reaction region 482. In the exemplary embodiment depicted in FIGS. 15A and 15B, heating of remotely activatable control element 488 produces expansion of the reaction region to expanded form 482', which increases the spacing of reaction sites 484. As shown in FIGS. 12A and 12B and FIGS. 13A and 13B, a change in the spacing of reaction sites may increase or decrease the rate of reaction, or modify another parameter of a reaction, in a manner that depends on the specific reaction and reactants. Heating or cooling of a reaction volume may also modify a chemical reaction by modifying the pressure or the pH or the osmolality or other reaction-pertinent chemical variables within the reaction space.

In various embodiments as described herein, the reaction region includes a first material capable of influencing a chemical reaction. The remotely activatable control element may modify one or more of the rate or reaction kinetcis of the chemical reaction by modifying the influence of the first material on the chemical reaction, or by modifying the rate of exposure of a reactant capable of participating in the chemical reaction to the first material, as described herein.

The first material capable of influencing a chemical reaction may influence the chemical reaction in a variety of ways. For example, the first material may be a reactant that is modified by participation in the chemical reaction or it may be non-reactant material that modifies at least one condition at which the reaction occurs. FIGS. 16A and 16B, 17A and 17B, and 18A and 18B illustrate several mechanisms by which a material such as a first material may influence a chemical reaction.

Figures 16A, 16B:
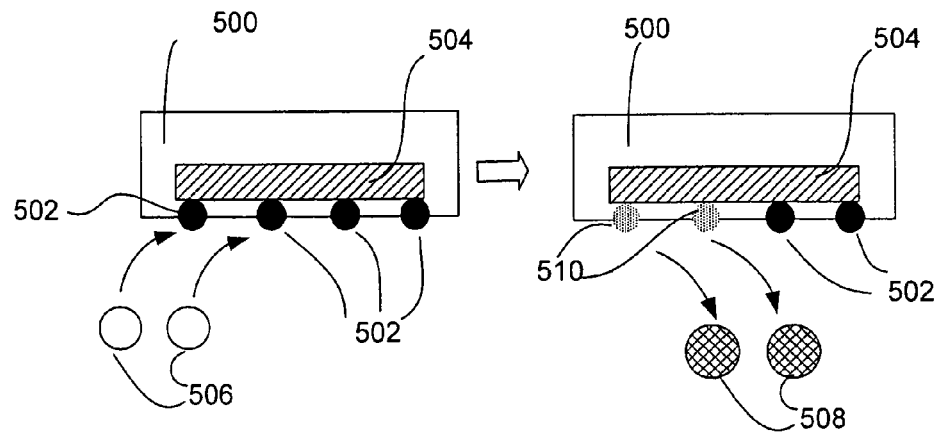
FIGS. 16A and 16B depict an exemplary embodiment of a reaction region.

FIGS. 16A and 16B depict a reaction 500 including a first material 502 that participates in the reaction as a reactant. Reaction device 500 also includes remotely activatable control element 504. A second reactant 506 approaches reaction region 500 in FIG. 16A and reacts with first material 502 to form reaction product 508, which is shown being released from reaction region 500 in FIG. 16B. A reaction by-product 510 may remain at reaction region 500, or may be released from reaction region 500. The quantity of first material 502 at reaction region 500 is thus depleted as the reaction occurs, and eventually the supply of first material 502 at reaction region 500 may be exhausted. The influence of the remotely activatable control element 504 is not illustrated in FIGS. 16A and 16B, but may be any of various influences, including but not limited to those described herein; e.g., modifying the temperature of the reaction region to modify the activity of first material 502, exposing reaction sites containing first material 502, modifying the spacing between reaction sites containing first material 502, or modifying the rate of delivery of second reactant 506 to reaction region 500. The reaction may produce a material that has a beneficial effect on the organism, including but not limited to a nutrient, hormone, growth factor, medication, therapeutic compound, enzyme, genetic materials, vaccines, vitamins, imaging agents, therapeutic compounds, a cell signaling material or neurotransmitter. Alternatively, the reaction may destroy, trap, or sequester a material from the body of the organism that is harmful to the organism. Such a material may include, for example lipids/cholesterol, plaque, infectious agents such as microbes and infectious/misfolded proteins such as prions, inflammatory agents such as cytokines/chemokines, growth factors, and autoreactive antibodies, oxidants, toxins, poisons, toxins, heavy metals, pollutants including organochlorine pollutants such as polychlorinated biphenyls (PCB) or dichlorodiphenyldichloroethylene (p,p'-DDE) and organophosphates, tobacco products, tar, or particulates. Reactions or processes by which a harmful material may be destroyed, trapped, or sequestered include degrading, chemically modifying, detoxifying, adsorbing, absorbing, enveloping, or killing the substance by chemical reactions such as enzymatic degradation and modification (e.g., alcohol dehydrogenase to remove alcohol), neutralization of free radicals by antioxidant scavenging, and adsorption with magnetic particles (e.g. labelled with binding moieties such as antibodies) for separation or sequestering, as a few examples.

In other embodiments, the first material may be a catalyst that facilitates a chemical reaction but is not modified by the chemical reaction, for example, metals such as platinum, acid-base catalysts, catalytic nucleic acids such as ribozymes or DNAzymes. The first material may be an enzyme, such as an oxidoreductase (e.g. glucose oxidase), transferase (including glycosyltransferase, kinase/phosphorylase), hydrolase, lyase, isomerase, ligase, and enzymatic complexes and/or cofactors. Various examples of catalysts are provided in Kozhevnikov, "Catalysts for Fine Chemical Synthesis, Volume 2, Catalysis by Polyoxometalates"; Chipsbooks.com; Bearing dates of 2002 and 1998-2006, printed on Oct. 21, 2005; pp 1-3 (201 pages); Volume 2; Culinary and Hospitality Industry Publications Services, which is incorporated herein by reference.

Figures 17A, 17B:
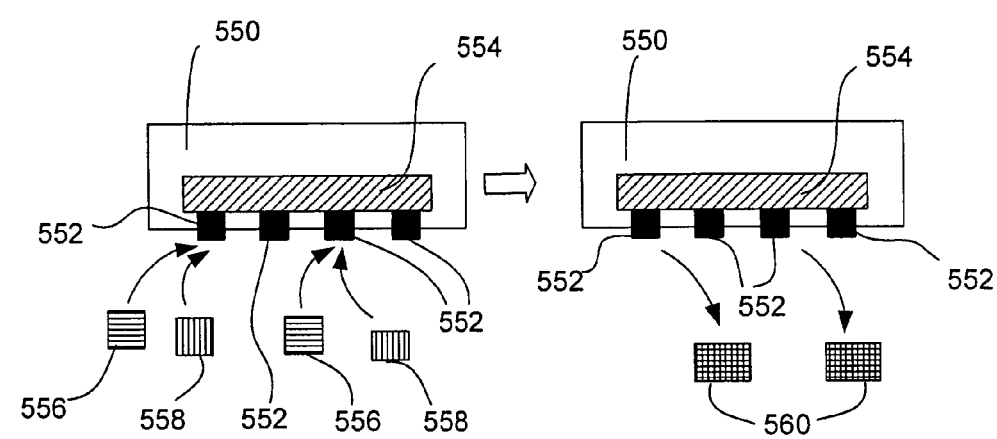
FIGS. 17A and 17B depict another exemplary embodiment of a reaction region.

FIGS. 17A and 17B depict an example in which a reaction region 550 includes a first material 552 that is a catalyst that facilitates the occurrence of the reaction at reaction region 550. Two or possibly more reactants (for example reactants 556 and 558 as shown in FIG. 17A) react at the reaction region 550 in the presence of first material 552. Reactants 556 and 558 are shown approaching first material 552 in reaction region 550 in FIG. 17A. In FIG. 17B, reaction product 560, formed from the reaction of reactants 556 and 558 with catalysis by first material 552, is shown being released from reaction region 550. Depending upon the particular reaction being carried out, one or more reaction by-products may be produces in addition to reaction product 560; however, such by-products are not depicted in FIG. 17B. A remotely activatable control element 554 may modify the effect of first material 552 on the reaction, by various mechanisms as described elsewhere herein. The supply of first material 556 at reaction region 550 is not depleted as the reaction occurs.

Figures 18A, 18B:
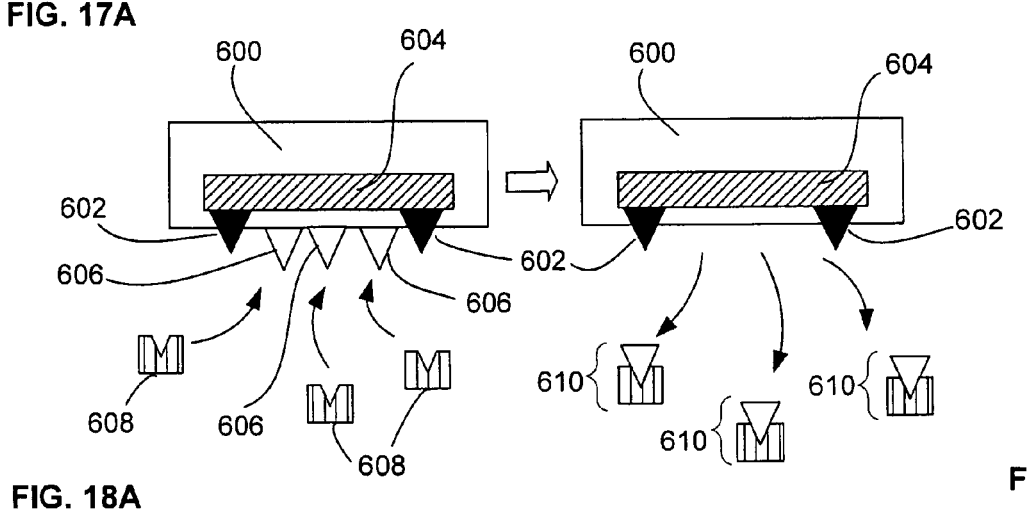
FIGS. 18A and 18B depict another exemplary embodiment of a reaction region.

FIGS. 18A and 18B depict an embodiment of a reaction region 600 in which the first material 602 modifies a reaction condition. The first material 602 may be a material that modifies the polarity of at least a portion of the reaction region, such as e.g. hydrophobic or hydrophilic groups; a material that modifies the pH of at least a portion of the reaction region, such as acids or acidifiers (e.g., ammonium chloride), bases or alkalizers (sodium bicarbonate, sodium acetate) or buffering agents; or a material that modifies the charge of at least a portion of the reaction region, such as including various enzyme, neuraminidase, transferase, antioxidants, and charge donors. A first reactant 606 is shown at reaction region 600. First reactant 606 reacts with a second reactant 608 to form a reaction product 610, shown in FIG. 18B, with the rate, kinetics, or other parameter of the reaction influenced by first material 602. A remotely activatable control element 604 may modify the effect of first material 602 by various mechanisms as described elsewhere herein. FIG. 18A depicts second reactant 608 approaching reaction region 600, and FIG. 18B shows reaction product 610 being released from reaction region 600.

As illustrated and described herein, in certain embodiments, the reaction device may include a body structure adapted for positioning in a body of an organism, having a reaction region located in or on the body structure, where the reaction region includes a first material capable of influencing a chemical reaction, and a remotely activatable control element operably coupled to the body structure and responsive to an electromagnetic field control signal to modify one or more of the rate or kinetics of the chemical reaction. The organism may be an animal or a human, or it may be plant. In some embodiments, the remotely activatable control element may modify one or more of the rate or reaction kinetics of the chemical reaction by modifying the influence of the first material on the chemical reaction, while in other cases the remotely activatable control element may modify one or more of the rate or reaction kinetics of the chemical reaction by modifying the rate of exposure of a reactant capable of participating in the chemical reaction to the first material.

Although various embodiments have described in connection with selected biomedical applications (e.g., with reaction devices adapted for placement in the body of a human or other animal), it is contemplated that reaction systems as described herein may be used in a variety of environments, not limited to the bodies of humans or other animals. Reaction devices may be placed in other types of living organisms (e.g., plants). Reaction devices may also be placed in bodies of water, or in various enclosed fluid volumes, in industrial, agricultural, and various other types of applications. The environments for use of embodiments described herein are merely exemplary, and the reaction systems as disclosed herein are not limited to use in the exemplary applications.

Beneficial materials in environment may include fertilizers, nutrients, remediation agents, antibiotics/microbicides, herbicides, fungicides, disinfectants. Harmful materials in an environment may include various toxins and pollutants, including hydrocarbon compounds, heavy metals, ore tailings, complex polysaccharide waste products, pathogens, microorganisms, toxins, bioweapons, chemical weapons, phosphates, explosives, and radionuclides. Reactions to get rid of harmful materials from an environment may include degrading, chemically modifying, detoxifying, adsorbing, absorbing, enveloping, or killing the substance. Materials may be adsorbed with electric or magnetic beads or particles for separation or sequestering, or enzymatic degradation or modification may be performed (see "Characterization of Chemically Modified Enzymes for Bioremediation Reactions", Davison et al., Final Report, U.S. Department of Energy, Oak Ridge National Laboratory, Project Number 55033, Sep. 22, 2000, which is incorporated herein by reference.)

According to various general embodiments, a reaction device may include a body structure adapted for positioning in an environment, a reaction region located in or on the body structure, the reaction region including a first material capable of influencing a chemical reaction, and a remotely activatable control element operably coupled to the body structure and responsive to input of energy from electromagnetic field control signal to modify one or more of the rate or kinetics of the chemical reaction through at least one of a mechanical, thermal, or chemical mechanism, which may be a direct mechanical, thermal, or chemical mechanism not mediated by electrical circuitry within or connected to the remotely activatable control element.

Further features that may be employed in reaction devices and systems are described in connection with certain exemplary embodiments, but may also be employed in other embodiments as described herein. As described herein, a remotely activatable control element may modify one or more of the rate or reaction kinetics of a chemical reaction by modifying the influence of a first material on the chemical reaction. In other embodiments, a remotely activatable control element may modify the rate or reaction kinetics of a chemical reaction by modifying the exposure of a reactant capable of participating in the chemical reaction to the first material. The exposure of a reactant to a first material may be modified by modifying the flow of a reactant through a reaction device, for example. In embodiments in which the reaction region is located in an interior portion of the body structure, the reaction device may include a valve responsive to a change in at least one dimension of the remotely activatable control element. The valve may be formed in its entirety by the remotely activatable control element, or the remotely activatable control element may form a part of the valve or the valve actuation mechanism. If the remotely activatable control element forms all or a part of a valve structure or system, it may modify the rate or kinetics of the reaction occurring in the reaction device by modifying the flow of fluid into or through the reaction device. The remotely activatable control element may respond to the control signal by changing in at least one dimension, and may include various materials, for example polymer, ceramic, dielectric or metal. For example, the remotely activatable control element may include a shape memory material such as a shape memory polymer, a memory foam, or a shape memory alloy such as nitinol (an alloy of titanium and nickel) or ferromagnetic shape memory materials ($Ni_2MnGa$ alloy). The remotely activatable control element may include a bimetallic structure.

Figure 19:
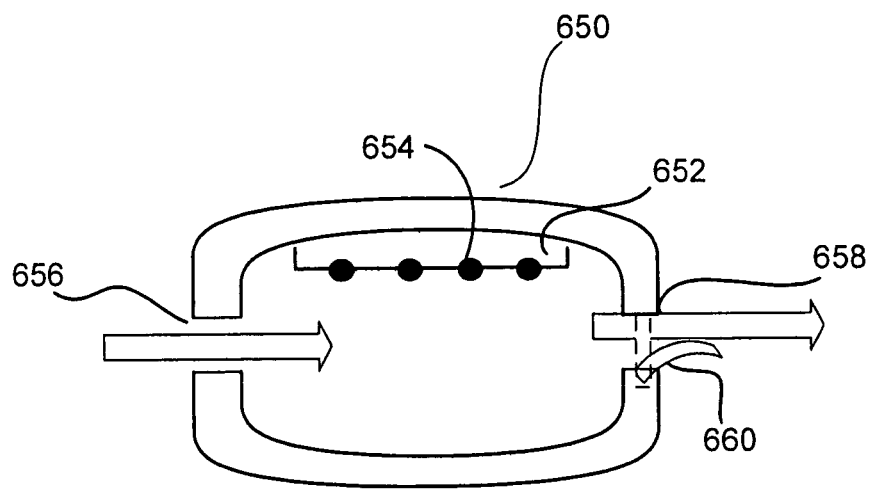
FIG. 19 is a cross-sectional view of a reaction device having a valve at an outlet.
Figure 20:
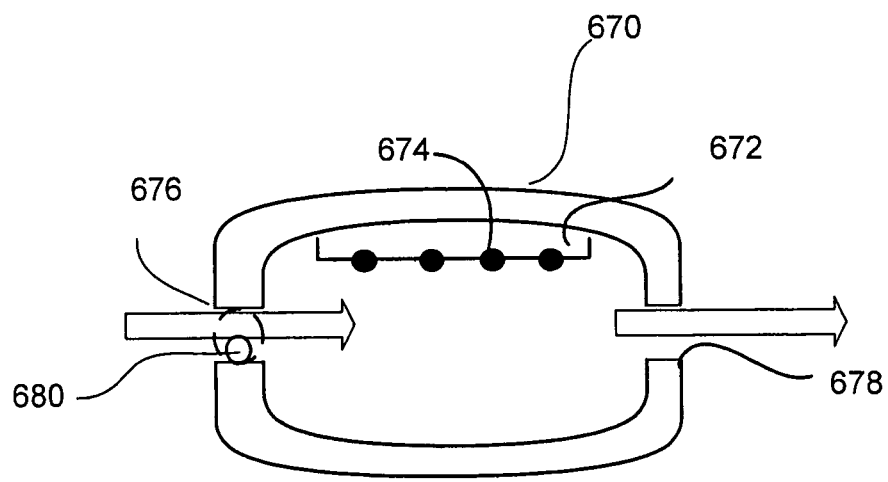
FIG. 20 is a cross-sectional view of a reaction device having a valve at an inlet.

FIGS. 19 and 20 depict embodiments in which the flow of reactant through a reaction device may be modified by the inclusion of a valve at an inlet or outlet of the reaction device. In FIG. 19, a reaction device 650 includes a reaction region 652 including first material 654. Reaction device 650 includes inlet 656 and outlet 658. In this example, remotely activatable control element 660 is a valve structure formed from a shape memory material. The rate of reaction may be modified by adjusting the valve to control the flow of fluid through the reaction device. The open position of the valve formed by remotely activatable control element 660 is indicated by a solid line, while the closed position is indicated by a dashed line. Other potential materials and structures for valves may be as described in U.S. Pat. Nos. 6,682,521, 6,755,621, 6,720,402, 6,607,553, which are incorporated herein by reference.

In the embodiment of FIG. 20, the remotely activatable control element may include an expandable gel structure, such as hydrogel or a ferrogel. FIG. 20 depicts a reaction device 670 having a reaction region 672 including first material 674 and an inlet 676 and outlet 678 providing for the flow of fluid through the reaction device from the environment. Remotely activatable control element 680 forms a valve for controlling the flow of fluid into the reaction device, shown in its open (contracted) form by a solid line and shown in its closed (expanded) form by a dashed line. The rate of reaction may be modified by adjusting the valve to control the flow of fluid through the reaction device. An example of a magnetically controlled hydrogel valve is described in "A temperature controlled micro valve for biomedical applications using a temperature sensitive hydrogel" Micro Total Analysis Systems Symposium, November 3-7, Nara, Japan, 1:142-144 H. J. van der Linden, D. J. Beebe, and P. Bergveld (2002), incorporated herein by reference.

In addition to the embodiments shown in FIGS. 19 and 20, in other embodiments a reaction device may include valves controlling fluid flow through both an inlet and an outlet. Various other remotely activatable valve structures may be used in other embodiments, and are not limited to the examples provided here.

Remotely activatable control elements used in various general embodiments of reaction devices and systems may include a magnetically active material, such as at least one of a permanently magnetizable material, a ferromagnetic material, a ferrimagnetic material, a ferrous material, a ferric material, a diamagnetic material, a paramagnetic material, and an antiferromagnetic material, or may include an electrically active material, such as at least one of a permanently 'poled' dielectric, a ferroelectric, a dielectric or a piezoelectric material. In some embodiments the remotely activatable control element may include a polymer and a magnetically active or an electrically active component. The electrically or magnetically active component may be heatable by the incident electromagnetic control signal, wherein heating of the electrically or magnetically active component causes the polymer to undergo a change in configuration that modifies the influence of the first material on the chemical reaction. In some embodiments, the temperature may be modified within some or all of a reaction volume within a reaction device, while in other embodiments the temperature change may be limited to a reaction region and the temperature within the reaction volume may remain substantially unchanged. In some embodiments, the rate of reaction may be directly dependent upon the temperature of the reaction region or reaction volume. In some embodiments, a characteristic of the reaction other than the rate of reaction may be modified by a change in temperature. For example, a change in temperature may cause a particular reaction product to be favored over another reaction product, so that changing the temperature may modify the proportions of certain reaction products.

A remotely activatable control element may be responsive to various electromagnetic fields, including a static or quasistatic electrical field or static or quasi-static magnetic field, or radio-frequency, microwave, infrared, millimeter wave, optical, or ultraviolet electromagnetic radiation. In some embodiments, the remotely activatable control element may be responsive to non-ionizing electromagnetic radiation. The response of the remotely activatable control element to an electromagnetic field may be due to absorption of energy from the electromagnetic signal or due to torque or traction on all or a portion of the remotely activatable control element due to the electromagnetic field. The response will depend upon the intensity, the relative orientation and the frequency of the electromagnetic field and upon the geometry, composition and preparation of the material of the remotely activatable control element. A response may occur on the macro level, on a microscopic level, or at a nanoscopic or molecular level.

Figure 21:
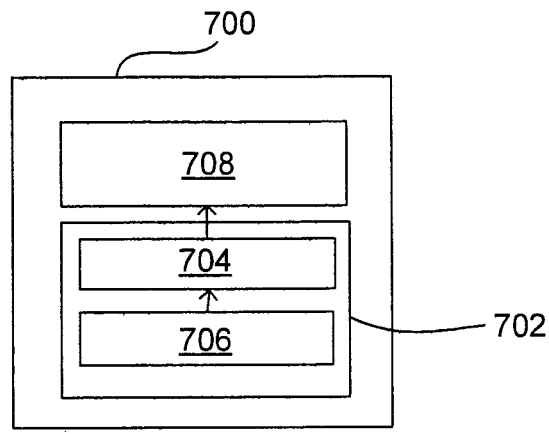
FIG. 21 illustrates an embodiment of a reaction device including an antenna.

In some embodiments, a remotely activatable control element may include a receiving element such as an antenna or other geometric gain structure to enhance the receiving of an electromagnetic control signal transmitted from a remote control signal generator. FIG. 21 depicts in schematic form an embodiment of a reaction device 700 including a remotely activatable control element 702 that includes an active portion 704 and an receiving element 706, and a reaction region 708. Reaction region 708 may be generally as described in connection with various exemplary embodiments, for example as shown in FIGS. 2, 3 and 5, but it not depicted in any detail in FIG. 21 for the sake of simplicity. Receiving element 706 may be any structure that has a size, shape, and material that is suitable for receiving and transducing electromagnetic energy of a particular frequency or frequency band. In some embodiments, receiving element 706 may be highly frequency-selective, while in other embodiments it may react usefully over a wide frequency band, or over multiple frequency bands. Receiving element 706 may be formed of various metallic or electrically or magnetically active materials. Active portion 704 may include various materials that respond mechanically, thermally or chemically to electromagnetic energy received and transduced by receiving element 706 to influence a reaction that occurs in reaction region 708.

Figure 22:
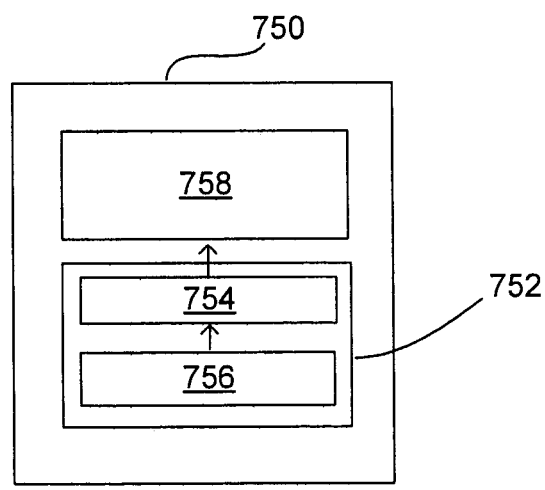
FIG. 22 illustrates an embodiment of a reaction device including a resonant element.

FIG. 22 depicts an embodiment of a reaction device 750 including a remotely activatable control element 752 that includes an active portion 754 and a resonant element 756, and a reaction region 758. As in the embodiment of FIG. 21, reaction region 758 may be generally as described in connection with various exemplary embodiments. Resonant element 756 may be configured to be activated or energized at a resonant frequency in response to the electromagnetic control signal. Active portion 754 may include various materials that respond mechanically, thermally or chemically in response to transfer of energy from resonant element 756 upon activation thereof to influence a reaction that occurs in reaction region 758.

FIG. 23 depicts a reaction device 800 including a reaction space 802. In this embodiment, a plurality of molecules 804 function as both the remotely activatable control element and as the first material (that modifies the chemical reaction). A reactant material 808 is also present within reaction space 802. Each molecule 804 includes an excitable chemical bond 806. Prior to excitation of excitable chemical bond 806, no or limited reaction occurs, as shown in FIG. 23. After excitation of excitable chemical bond 806 to excited condition 806', as shown in FIG. 24, reactant material 808 may bind or associate with molecule 804 to undergo a chemical reaction. Selective excitation of multiple chemical bonds may be performed in some embodiments, as described in Ishikawa et al., "Selective Resonance of Chemical Structures," U.S. patent application Ser. No. 11/186,635, filed 21 Jul. 2005, which is incorporated herein by reference, and commonly assigned with the present application.

Figure 25:
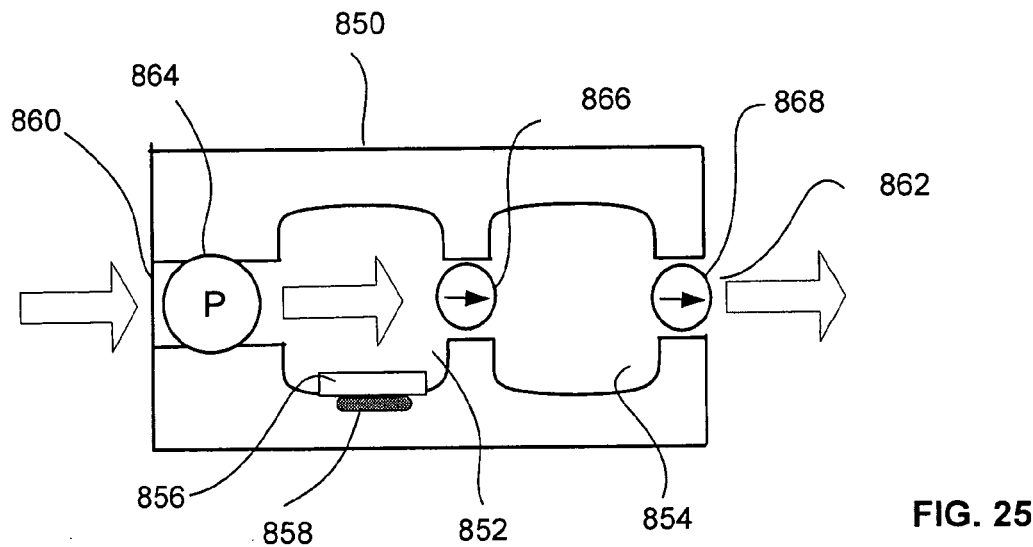
FIG. 25 is a cross-sectional view of an embodiment of a reaction device.

FIG. 25 depicts a further embodiment of a reaction device 850, illustrating other potential reaction device features. Reaction device 850 includes a first chamber 852, second chamber 854, reaction region 856, and remotely activatable control element 858. Reaction device 850 also includes inlet 860, outlet 862, pump 864, valve 866 between chamber 852 and chamber 854 and valve 868 at outlet 862. First chamber 852 may function as a reaction chamber. Pump 860 may move fluid through reaction device 850. Any or all of features illustrated in FIG. 25 may be included in various embodiments of reaction devices. Reaction devices may include multiple spaces or chambers, one or more of which may function as reaction chambers. Reaction devices may include additional fluid handling elements (e.g., inlets, outlets, pumps, valves, mixers, separators, chambers, channels, reservoirs, and so forth, as are known to those of skill in the arts of fluid handling). Active elements (which may include, for example, pumps, valves, and mixers) may be controlled by electrical, magnetic, or electromagnetic control signals. A reaction device may include one or both of an outlet through which a product of the chemical reaction is released into the environment or an inlet through which a second material capable of participating in the chemical reaction enters the reaction region. Some embodiments may include only a single inlet and a single outlet. In some embodiments a single opening may function as both inlet and outlet. In some embodiments there may be multiple inlets or multiple outlets, or both. The invention is not limited to specific numbers or combinations of inlets, outlets, or openings that function as both inlet and outlet. Although in the exemplary embodiment of FIG. 25 the reaction region is shown in an interior portion of a reaction device, in other embodiments the reaction region may be located on an exterior portion of the body structure in fluid communication with the environment. If the reaction region is in fluid communication with the environment via an inlet or outlet, the reaction device may include a valve responsive to a change in at least one dimension of the remotely activatable control element. A valve may be configured to modify the flow of fluid into the reaction region responsive to the change in at least one dimension of a remotely activatable control element, or to modify the flow of fluid out of the reaction region responsive to the change in at least one dimension of the remotely activatable control element. Examples of fluid handling structures suitable for use in selected embodiments are described in U.S. Pat. Nos. 6,146,103 and 6,802, 489, and in Krauβ et al., "Fluid pumped by magnetic stress"; Bearing a date of Jul. 1, 2004; pp. 1-3, all of which are incorporated herein by reference.

Reaction devices as described herein may include one or multiple remotely activatable control elements. In devices that include multiple remotely activatable control elements, the multiple remotely activatable control elements may all be of the same type, or may be of different types. Multiple remotely activatable control elements may be activated or controlled in parallel or in series. Selective activation or control of remotely activatable control elements may be achieved by configuring remotely activatable control elements to be activated by electromagnetic control signals having particular signal characteristics, which may include, for example, particular frequency, phase, amplitude, temporal profile, polarization, and/or directional characteristics, and spatial variations thereof. For example, different control elements may be responsive to different frequency components of a control signal, thereby allowing selective activation of the different control elements. A reaction device may include multiple selectively activatable control elements, each associated with a particular fluid handling element, which may thus be controlled to perform multiple fluid-handling or reaction steps in a particular sequence. It is also contemplated that a reaction system may include multiple reaction devices which may be of the same or different types. For example, multiple identical reaction devices may be distributed throughout an environment in order to perform a particular chemical reaction or process at multiple locations within the environment. Alternatively, a reaction system may include multiple different reaction devices at different locations within and environment, each performing or controlling a reaction suited for the particular location. The invention as described herein is not limited to devices or systems including any specific number or configuration of remotely activatable control elements within a reaction device, or specific number or configuration of reaction devices or remote controllers within a reaction system. Depending upon the particular application of a system, remotely activatable control elements and/or reaction devices may be controlled in a particular pattern to accomplish one or more desired chemical reactions or reaction steps. Control of such systems may be performed with the use of suitable hardware, firmware, software, through one or multiple remote controllers.

Figure 26A:
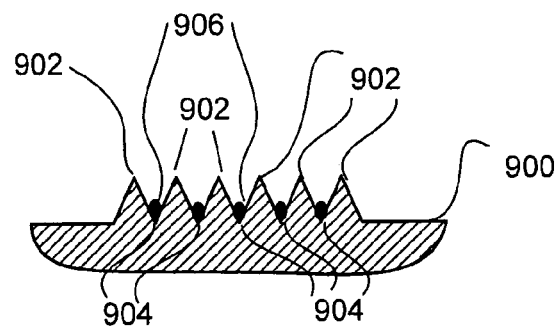
FIGS. 26A and 26B depict an example of the effect of unfolding a reaction region.
Figure 26B:
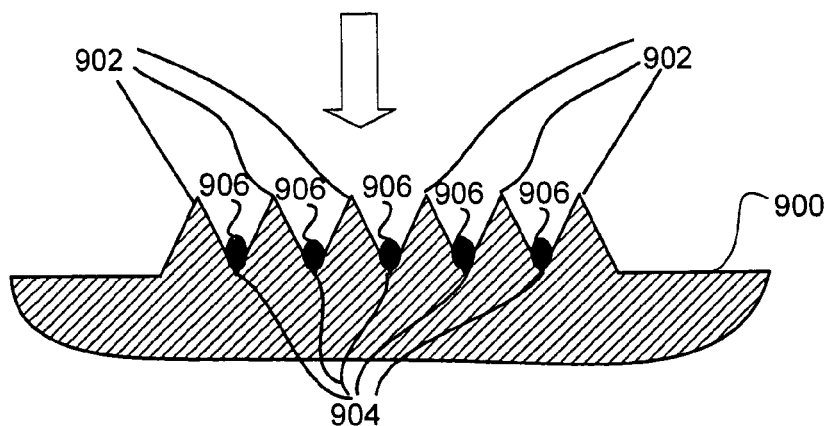

A change in dimension of the remotely activatable control element may serve to cause opening or closing of a valve or produce another modification of a portion of a reaction device. For example, additional portions of the reaction region may be exposed responsive to the change in at least one dimension of the remotely activatable control element. The surface area of the reaction region may be increased responsive to a change in at least one dimension of the remotely activatable control element. The volume containing the reaction region within the interior portion of the body structure may be modified responsive to the change in at least one dimension of the remotely activatable control element. The surface area of the reaction area may be increased by stretching of at least a portion of the reaction area. In some embodiments, the surface area of the reaction area may be increased by the unfolding of at least a portion of the reaction area to expose additional portions of the reaction area, as depicted in FIGS. 10A and 10B, or in FIGS. 26A and 26B. FIG. 26A illustrates in cross section the increase in the number of accessible functional groups on a reaction region by unfolding of a reaction region 900. The reaction region is pleated, including ridges 902 and recessed valleys 904. Functional groups 906 are located within valleys 904 of the pleats. Stretching of the reaction region 900 to flatten and widen valleys 904 causes the functional groups 906 to become accessible to reactant, thus increasing influence of the functional groups as shown in FIG. 26B. The functional groups may have various influences, for example, functioning as reaction sites, or modifying the surface charge, surface energy, or local ionic strength or pH. It should be appreciated that the pleated surface depicted in FIGS. 26A and 26B are exemplary, and other forms of folding, deformation, or compression of the reaction region may provide a similar effect.

As described previously in connection with FIGS. 12A-13B, increasing the surface area of the reaction region may increase or decrease the rate of the reaction. Increasing the surface area of the reaction region may increase the number of (available) reaction sites on the reaction region, as illustrated in FIGS. 26A and 26B.

Figure 27:
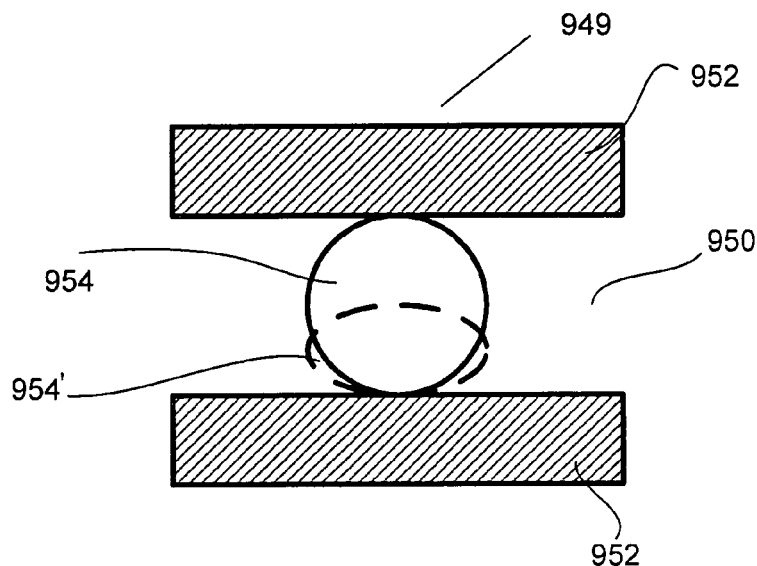
FIG. 27 is a cross-sectional view of an embodiment of a valve including a remotely activatable valve element.

In some embodiments, a remotely activatable control element may respond to a control signal by liberating or absorbing heat. The remotely activatable control element may respond to the control signal by changing shape. Such a remotely activatable control element may include, for example, a valve element or a structural element. FIG. 27 is a cross-sectional view of an embodiment of a valve 949 in channel 950 defined by walls 952 and including a remotely activatable valve element 954 positioned in a channel 950. Valve element 954 may be a magnetically or electrically responsive element formed from, for example, a ferropolymer or other material responsive to applied magnetic or electric or electromagnetic fields or radiation. Valve element may have a first form 954, indicated by the solid outline, when exposed to a first magnetic or electric field strength, and a second form 954', indicated by the dashed outline, when exposed to a second magnetic or electric field strength. Valves of this type are disclosed, for example, in "A temperature controlled micro valve for biomedical applications using a temperature sensitive hydrogel" Micro Total Analysis Systems Symposium, November 3-7, Nara, Japan, 1:142-144, H. J. van der Linden, D. J. Beebe, and P. Bergveld (2002), incorporated herein by reference. See also U.S. Pat. Nos. 5,643,246, 5,830,207, and 6,755,621, which are also incorporated herein by reference. In first form 954, valve element 954 obstructs channel 950, blocking the flow of fluid through valve 949. In its second form 954', valve element 954 does not obstruct channel 950, and fluid flow through valve 949 is unimpeded.

Figure 28:
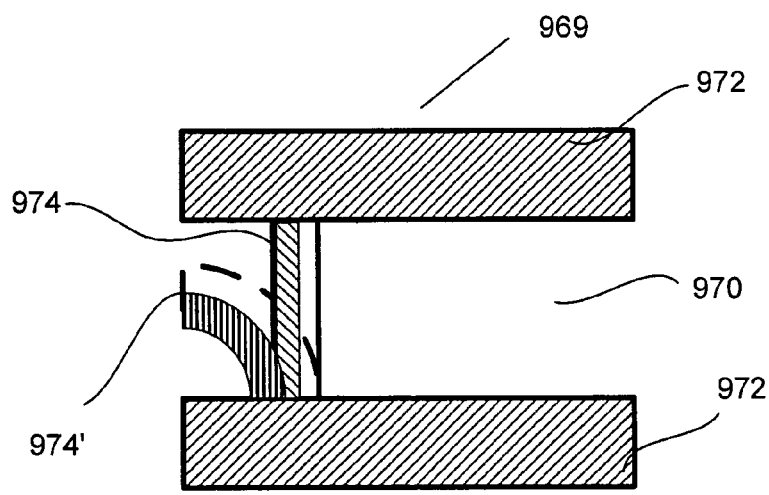
FIG. 28 is a cross-sectional view of an embodiment of a valve including a remotely activatable valve element.

FIG. 28 is a cross-sectional view of an embodiment of another type of valve 969, in which fluid channel 970 defined by walls 972 includes a remotely activatable valve element 974. Remotely activatable valve element 974 is formed, for example from a bimetallic strip that changes from a first configuration to a second configuration during heating produced by exposure to a magnetic or electric or electromagnetic field or radation control signal.

In these and other valve structures (e.g., as depicted in FIG. 19), opening or closing of the valve may be produced by a transient application of a magnetic or electric or electromagnetic control signal, the control signal serving to cause switching of the valve element from a first configuration to a second configuration, or continuous application of a control signal may be required to maintain the valve element in one of the two configurations, with the valve element returning to the other configuration upon removal of the control signal. Such a valve element may be formed from a shape memory metal, a shape memory polymer, or a bimetallic strip formed from laminated layer of metals having different coefficients of thermal expansion, for example. The construction of such valve elements is known to those of skill in the relevant arts, for example.

The reaction device may include an outlet through which a product of the chemical reaction is released into the environment or an inlet through which a second material capable of participating in the chemical reaction enters the reaction region. The first material included in the reaction region may influence the reaction in various ways. The first material may be a reactant that is modified by participation in the chemical reaction, or it may be a non-reactant material that modifies at least one condition at which the reaction occurs. Reaction conditions may include, for example, temperature, osmolality, pH, surface energy, or surface charge at the reaction reaction. The first material may be a catalyst that facilitates the chemical reaction but is not modified by the chemical reaction. The reaction may produce a material that has a beneficial effect in the environment, or it may destroy, trap, or sequester a harmful material from the environment.

In different embodiments, the reaction device may include a body structure adapted for positioning in different types of environments, including, for example, the body of an organism, a body of water, or a contained fluid volume. Contained fluid volumes may be of various types and of various volumes; some examples include industrial fluid volumes, agricultural fluid volumes, swimming pools, aquariums, drinking water supplies, and HVAC system cooling water supplies.

Figure 29:
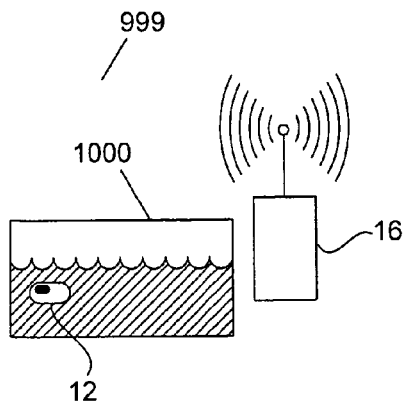
FIG. 29 illustrates an embodiment of a system including a remotely controlled reaction device.

FIG. 29 illustrates an exemplary embodiment of a reaction system 999 in which a reaction device 12 is located in a small enclosed fluid volume 1000 (e.g., an aquarium). A remote controller or remote control signal generator 16 is located outside enclosed fluid volume 1000.

Figure 30:
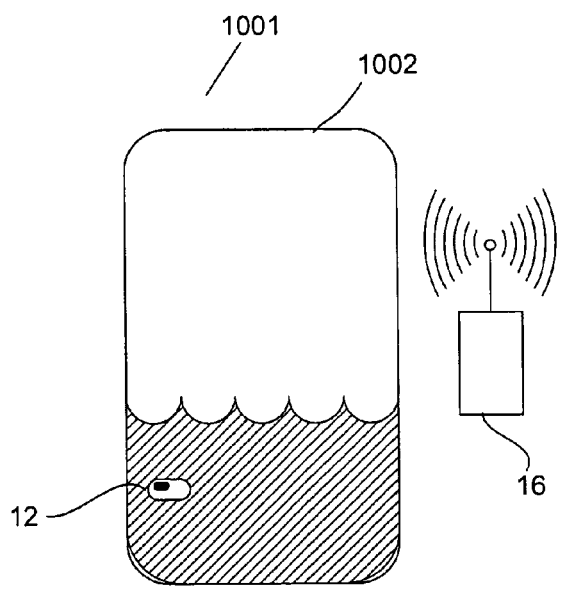
FIG. 30 illustrates an embodiment of a system including a remotely controlled reaction device.

FIG. 30 illustrates a further exemplary embodiment of a reaction system 1001 in which a reaction device 12 is located in a larger enclosed fluid volume 1002 (which may be, for example, a water storage tank, an HVAC system cooling water tank, a tank containing an industrial fluid or an agricultural fluid). A remote controller or remote control signal generator 16 is located outside enclosed fluid volume 1001.

Figure 31:
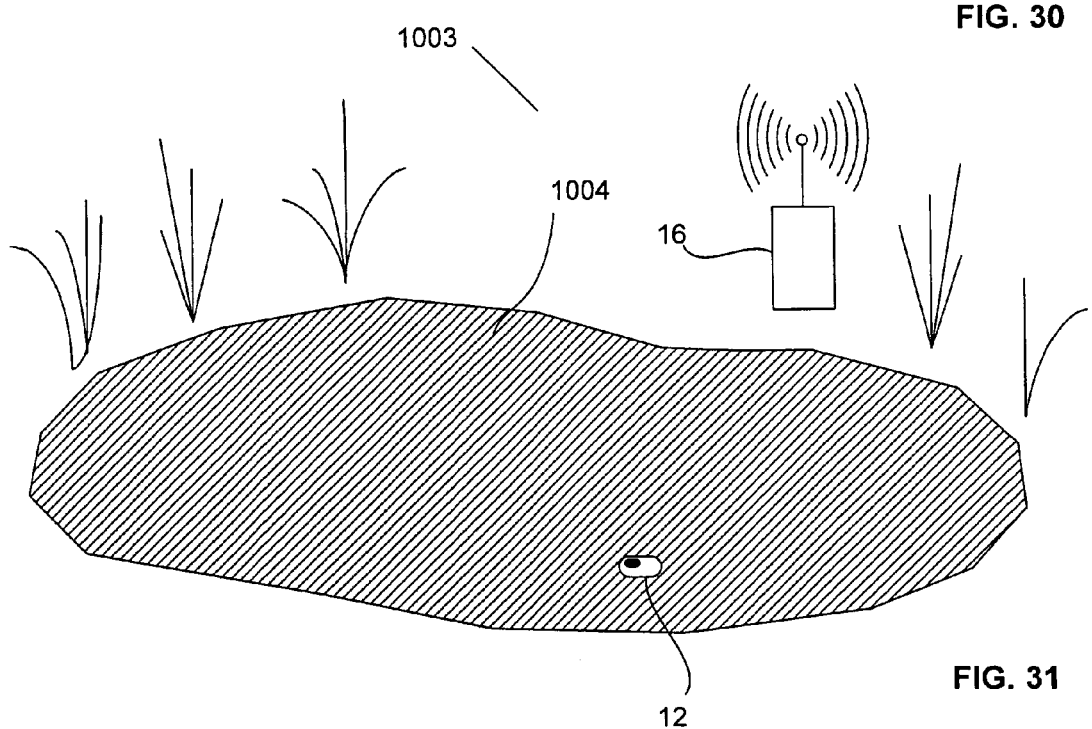
FIG. 31 illustrates an embodiment of a system including a remotely controlled reaction device.

FIG. 31 illustrates a further exemplary embodiment of a reaction system 1003 in which a reaction device 12 is located in a body of water 1004 (a lake or pond is depicted here; though such reaction systems may also be designed for use in rivers, streams, or oceans). The remote controller or remote control signal generator 16 is shown located outside of body of water 1004, though in some embodiments it may be advantageous to place remote controller 16 at a location within body of water 1004.

Referring back to FIG. 6, remote controller 102 for a reaction system 100 may include an electromagnetic signal generator 114 capable of producing an electromagnetic signal configured to be received by a remotely activatable control element 108 of a reaction device 104 located in an environment 106 and to activate the remotely activatable control element mechanically, thermally or chemically to produce a desired rate of a chemical reaction in the reaction device 104, and an electromagnetic signal transmitter 116 capable of transmitting the electromagnetic signal to the remotely activatable control element. The electromagnetic signal generator may include electrical circuitry 112 and/or a microprocessor. In some embodiments, the electromagnetic signal may be produced at least in part according to a pre-programmed pattern. The electromagnetic signal may have a strength and frequency composition sufficient to produce a change in dimension in the remotely activatable control element, e.g. a contraction or expansion in at least one dimension. In some embodiments, the electromagnetic signal may have strength and frequency composition sufficient to produce a change in temperature or change in shape or position or orientation in the remotely activatable control element. For example, the electromagnetic signal may have strength and frequency composition sufficient to produce a change in shape in a remotely activatable control element comprising a shape memory material such as a shape memory metal or shape memory polymer, a bimetallic structure, or a polymeric material. The change in shape in a remotely activatable control element may causes opening or closing of a valve. In other embodiments, the change in shape in a remotely activatable control element may cause expansion of a reaction region or an increase or decrease in volume of a reaction space.

Figure 32:
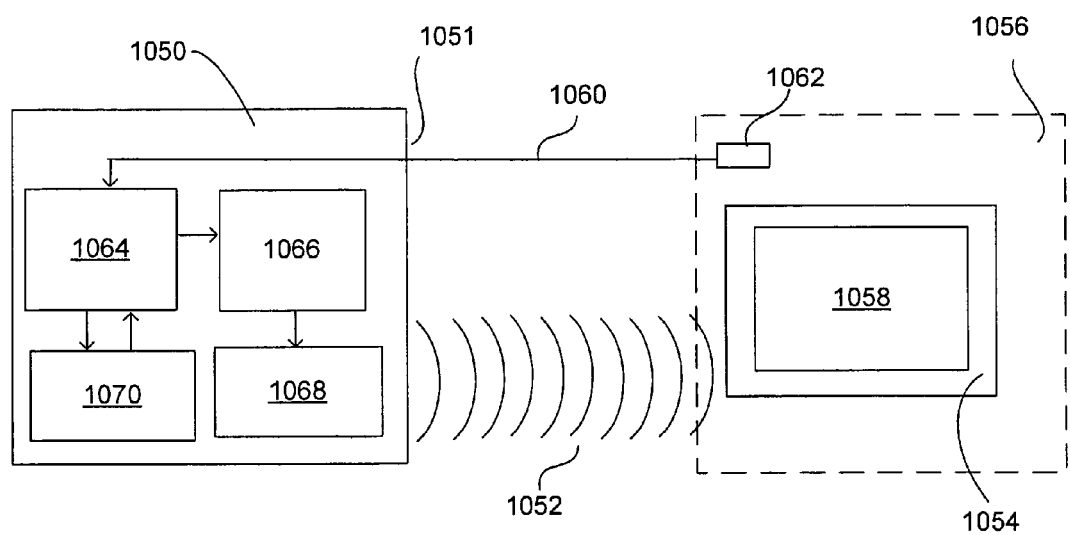
FIG. 32 depicts an embodiment of a system including a remote control device and a reaction device including a sensor.
Figure 33:
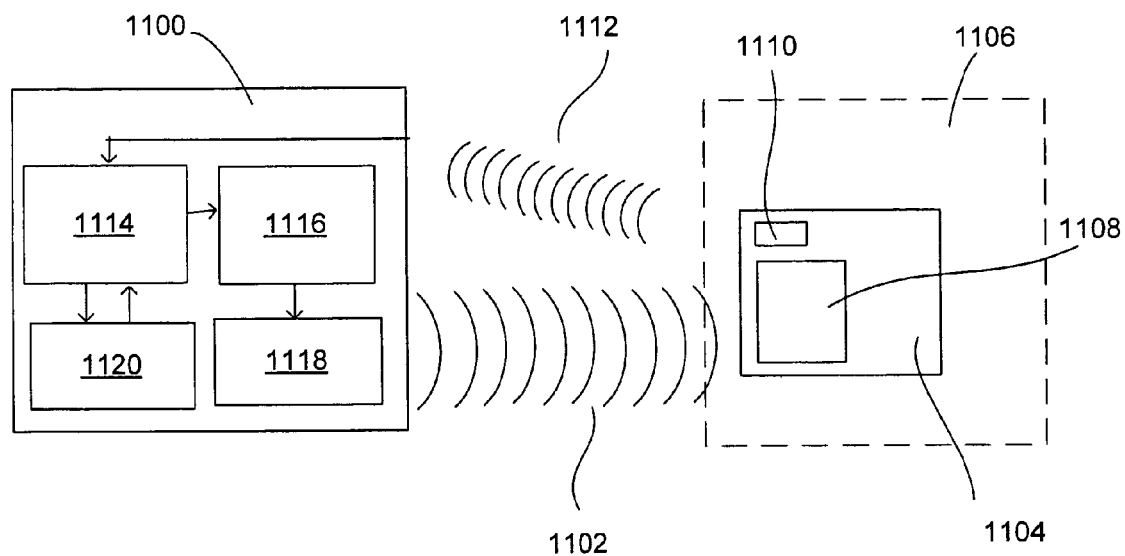
FIG. 33 depicts an embodiment of a system including a remote control device and a reaction device including a sensor.
Figure 34:
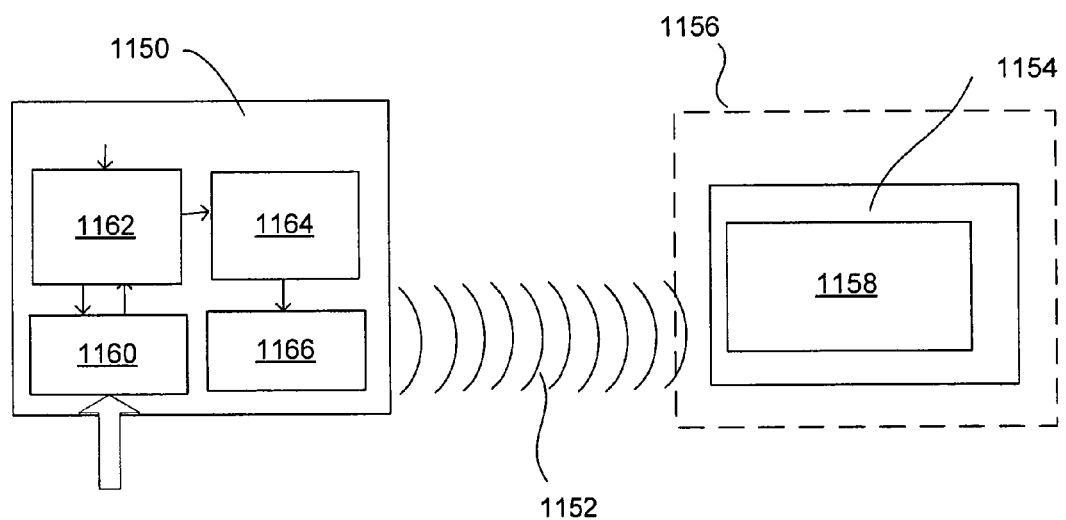
FIG. 34 depicts an embodiment of a system including a remote control device and a reaction device including a sensor.

Various embodiments of remote controller or remote control signal generators are illustrated in schematic form in FIGS. 32-34. FIG. 32 depicts a reaction system including a remote controller 1050, which transmits an electromagnetic control signal 1052 to reaction device 1054 positioned in environment 1056. Reaction device 1054 may include a remotely activatable control element 1058, as described previously. Remote controller 1050 may include a signal input 1051 adapted for receiving a feedback signal 1060 from sensor 1062 in environment 1056, and electromagnetic control signal 1052 may be determined based at least in part upon feedback signal 1060. Feedback signal 1060 may correspond, for example, to the concentration or activity of a chemical in the environment, the osmolality or pH of the environment, or the pressure or temperature of the environment. Remote controller 1050 may include electrical circuitry 1064, signal generator 1066, signal transmitter 1068, and memory 1070, for example. Feedback from sensor 1062 may be transmitted wirelessly from reaction device 1054, or in some embodiments sent via a wire connection.

In some embodiments, the remote controller may include a signal input adapted for receiving a feedback signal from the reaction device, and the electromagnetic signal may be determined based at least in part upon the feedback signal. The feedback signal may be obtained from a sensor within the reaction device 1104. Examples of sensors are described in, U.S. Pat. No. 6,935,165, and U.S. Patent Publication 2004/0007051, both of which are incorporated herein by reference. FIG. 33 depicts a reaction system including remote controller 1100, which transmits electromagnetic control signal 1102 to reaction device 1104, which is positioned in environment 1106. Reaction device 1104 includes remotely activatable control element 1108 and sensor 1110, which produces a feedback signal 1112 that may be transmitted wirelessly back to remote controller 1100. Remote controller 1100 may include processor 1114, signal generator 1116, signal transmitter 1118, and memory 1120.

FIG. 34 illustrates a further embodiment of a reaction system in which remote controller 1150 includes input 1160 for receiving input of information or instructions from a user such as, for example, commands, variables, durations, amplitudes, frequencies, waveforms, data storage or retrieval instructions, patient data, etc. As in the other embodiments, remote controller 1150 transmits electromagnetic control signal 1152 to reaction device 1154 in environment 1156, where it activates remotely activatable control element 1158. Input 1160 may include one or more input devices such as a keyboard, keypad, microphone, mouse, etc. for direct input of information from a user, or input 1160 may be any of various types of analog or digital data inputs or ports, including data read devices such as disk drives, memory device readers, and so forth in order to receive information or data in digital or electronic form. Data or instructions entered via input 1160 may be used by electrical circuitry 1162 to modify the operation of remote controller 1150 to modulate generation of an electromagnetic control signal 1152 by signal generator 1164 and transmission of the control signal 1152 by transmitter 1166.

Figure 35:
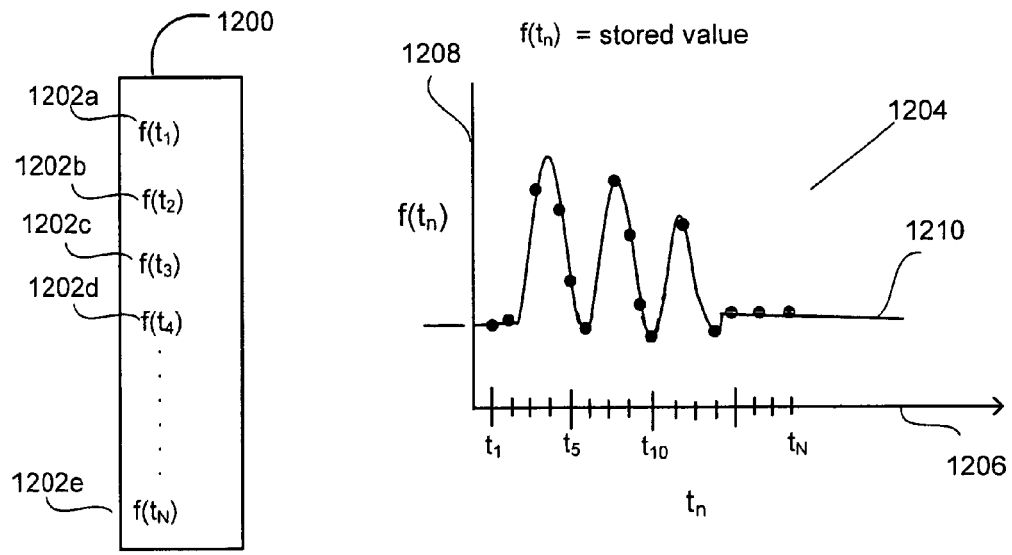
FIG. 35 illustrates a control signal generated from stored pattern data.

The electromagnetic control signal may be produced based at least in part upon a predetermined activation pattern. As shown in FIG. 35, a predetermined activation pattern may include a set of stored data 1202a, 1202b, 1202c, 1202d, . . . 1202e, having values $f(t_1)$, $f(t_2)$, $f(t_3)$, $f(t_4)$, . . . $f(t_N)$, stored in a memory location 1200. The activation pattern upon which the electromagnetic signal is based is depicted in plot 1204 in FIG. 35. In plot 1204, time $t_n$ is indicated on axis 1206 and signal amplitude $f(t_n)$, which is a function of $t_n$, is indicated on axis 1208. The value of the electromagnetic signal over time is represented by trace 1210. The predetermined activation pattern represented by data 1202a, 1202b, 1202c, 1202d, . . . 1202e may be based upon calculation, measurements, or any other method that may be used for producing an activation pattern suitable for activating a remotely activatable control element. Memory 1200 may be a memory location in a remote controller. As an example, a simple remote controller may include a stored activation pattern in memory and include electrical circuitry configured to generate an electromagnetic control signal according to the pattern for a preset duration or at preset intervals, without further input of either feedback information or user data. In a more complex embodiment, a predetermined activation pattern may be generated in response to certain feedback or user input conditions.

Figure 36:
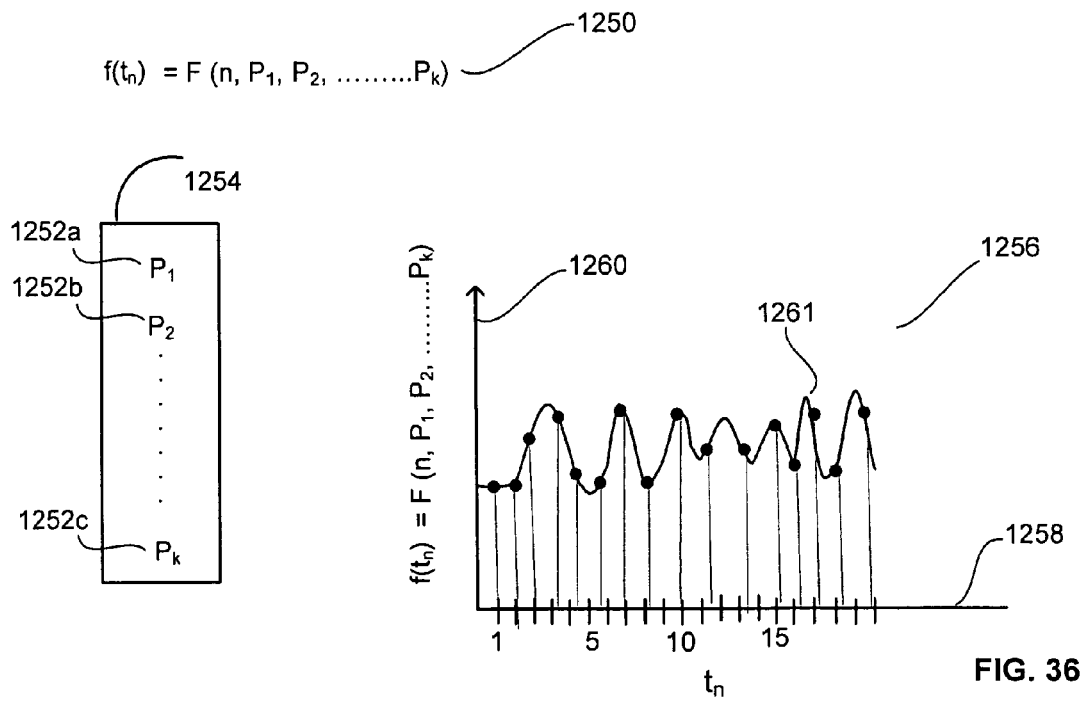
FIG. 36 illustrates a control signal calculated from a model based on stored parameters.

An electromagnetic signal may also be produced based upon a model-based calculation. As shown in FIG. 36, an activation pattern $f(t_n)$ may be a function not only of time ($t_n$) but also of model parameters $P_1, P_2, \ldots P_k$, as indicated by equation 1250. Data 1252a, 1252b, ... 1252c having values $P_1, P_2, \ldots P_k$ may be stored in memory 1254, as shown in FIG. 36. An electromagnetic control signal may be computed from the stored model parameters and time information. For example, as indicated in plot 1256, time is indicated on axis 1258 and the strength or amplitude of the electromagnetic control signal is indicated on axis 1260, so that trace 1261 represents $f(t_n)$. As discussed previously in connection with FIG. 35, memory 1254 may be a memory location in a remote controller. The remote controller may generate an electromagnetic control signal based upon the stored function and corresponding parameters. In some embodiments, the electromagnetic control signal may also be a function of one or more feedback signals (from the reaction device or the environment, for example) or of some user input of data or instructions.

Figure 37:
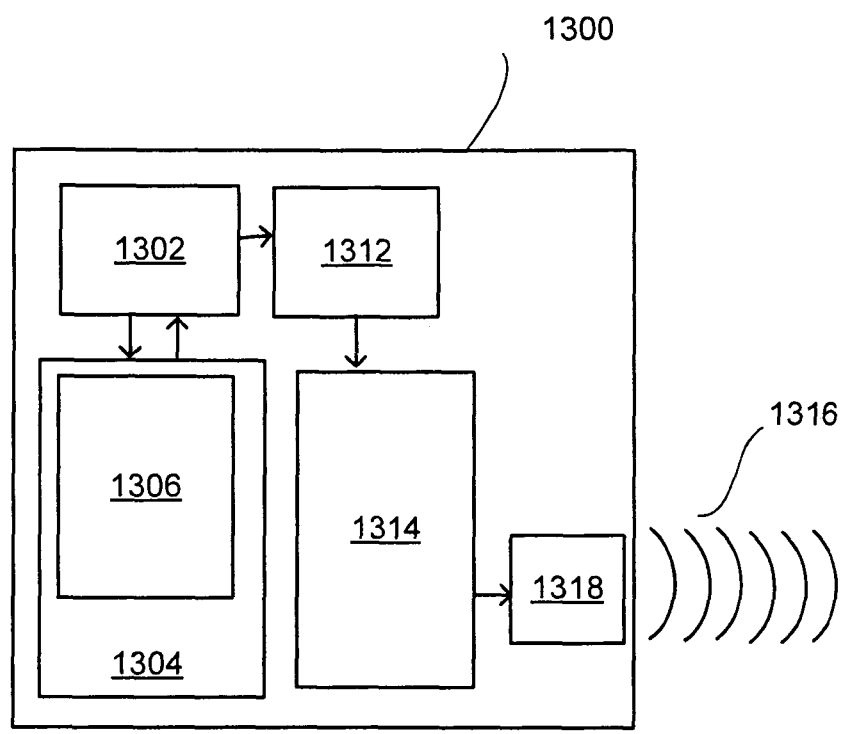
FIG. 37 illustrates an embodiment of a remote control device including software for controlling control signal generation and transmission.

FIG. 37 depicts a remote controller 1300 having a memory 1304 capable of storing pre-determined data values or parameters used in model-based calculation, as described in connection with FIGS. 35 and 36. Remote controller 1300 may also include processor 1302, signal generator 1312, and signal transmitter 1314 for transmitting electromagnetic control signal 1316, generally as described previously. Memory 1304 may include memory location 1306 for containing a stored activation pattern or model parameters; portions of memory 1304 may also be used for storing operating system, program code, etc. for use by processor 1302. The controller 1300 may also include a beam director 1318, such as an antenna, optical element, mirror, transducer, or other structure that may impact control of electromagnetic signaling.

Electromagnetic control signals may have a variety of parameters or characteristics that may be selected or controlled. In some cases, the electromagnetic signal may have one or both of a defined magnetic field strength or defined electric field strength. An electromagnetic signal generator may be capable of producing an electromagnetic signal that includes a static or quasi-static magnetic field or electrical field. Various embodiments of electromagnetic signal generators may be capable of producing an electromagnetic signal that includes non-ionizing electromagnetic radiation. In selected embodiments, an electromagnetic signal generator may be capable of producing an electromagnetic signal that includes one or more of radio-frequency, microwave, millimeter wave, or optical, including without limitation, infrared, visible, X-ray, or ultraviolet, electromagnetic radiation.

Figure 38:
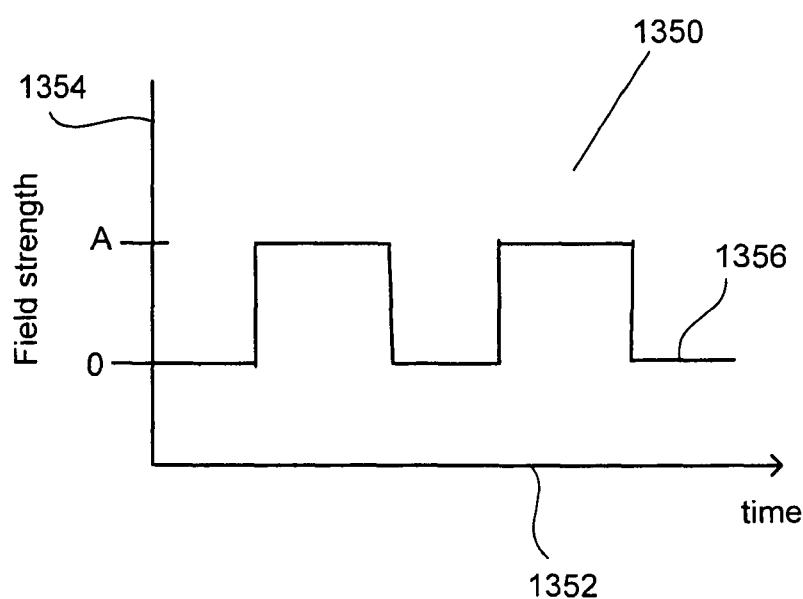
FIG. 38 depicts an exemplary control signal.

FIG. 38 depicts an example of an electromagnetic waveform. In plot 1350, time is plotted on axis 1352, and electromagnetic field strength is plotted on axis 1354. Trace 1356 has the form of a square wave, switching between zero amplitude and a non-zero amplitude, A.

Figure 39:
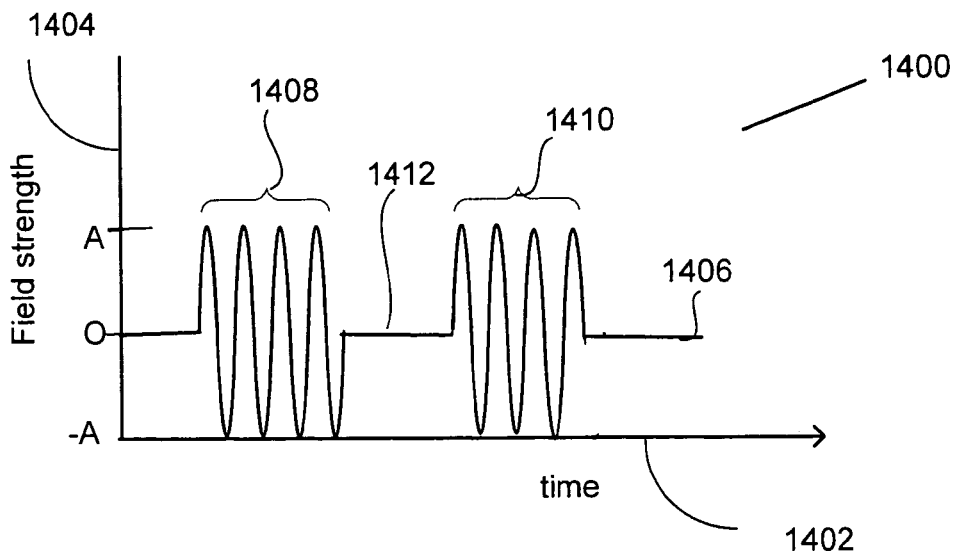
FIG. 39 depicts another exemplary control signal.

FIG. 39 depicts another example of an electromagnetic waveform. In plot 1400, time is plotted on axis 1402, and electromagnetic field strength is plotted on axis 1404. Trace 1406 includes bursts 1408 and 1410, during which the field strength varies between A and −A, at a selected frequency, and interval 1412, during which field strength is zero.

Figure 40:
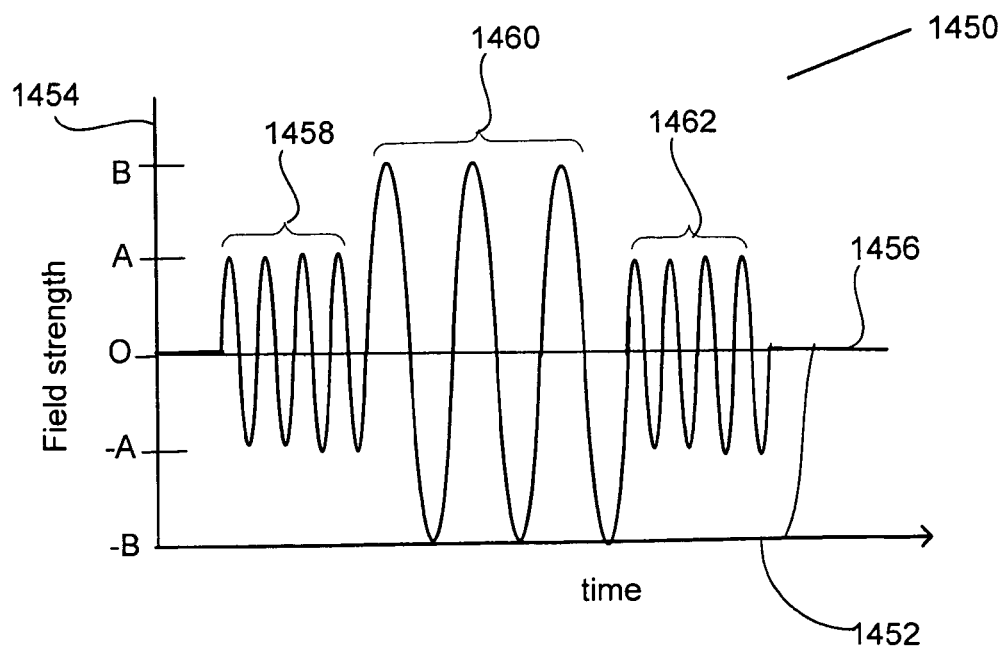
FIG. 40 depicts another exemplary control signal.

FIG. 40 depicts another example of an electromagnetic waveform. In plot 1450, time is plotted on axis 1452, and electromagnetic field strength is plotted on axis 1454. Trace 1456 includes bursts 1458, and 1462, during which the field strength varies between A and −A at a first frequency, and burst 1460, during which the field strength varies between B and −B at a second (lower) frequency. Different frequencies may be selectively receivey by certain individuals or classes of remotely activatable control elements within a device or system including multiple remotely activatable control elements. An electromagnetic control signal may be characterized by one or more frequencies, phases, amplitudes, or polarizations. An electromagnetic control signal may have a characteristic temporal profile and direction, and characteristic spatial dependences.

In one exemplary embodiment, a reaction system may include a reaction device responsive to a static or quasi-static magnetic field control signal, and a remote controller configured to generate a static or quasi-static magnetic field control signal. A system comprising a body structure adapted for positioning in an environment; a reaction region located in or on the body structure including a first material capable of influencing a chemical reaction; and a remotely activatable control element operably coupled to the body structure and responsive to a static or quasi-static electric or magnetic field control signal to modify one or more of the rate or kinetics of the chemical reaction. The remotely activatable control element may modify one or more of the rate or kinetics of the chemical reaction by modifying the influence of the first material on the chemical reaction. Alternatively, or in addition, the remotely activatable control element may modify the rate of exposure of a reactant capable of participating in the chemical reaction to the first material. As described in connection with other exemplary embodiments, the remotely activatable control element may include materials and structures such as a polymers, ceramics, dielectrics, metals, shape memory materials, bimetallic structures, magnetically or electric active materials, hydrogels, ferrogels, ferroelectrics, piezoelectrics, and composites or combinations of materials.

The remotely activatable control element may respond to the control signal by changing in at least one dimension. The reaction region may be located in an interior portion of the body structure and be at least intermittently in fluid communication with the environment via at least one inlet or outlet. Alternatively, in other embodiments the reaction region may be located on an exterior portion of the body structure in fluid communication with the environment. The reaction device may include a valve responsive to a change in at least one dimension of the remotely activatable control element to modify the flow of fluid into or out of the reaction region responsive to the change in at least one dimension of the remotely activatable control element. Additional portions of the reaction region may be exposed responsive to the change in at least one dimension of the remotely activatable control element. The surface area of the reaction region may be increased responsive to the change in at least one dimension of the remotely activatable control element. The system volume containing the reaction region within the interior portion of the body structure may be increased responsive to the change in at least one dimension of the remotely activatable control element. Exposure of additional portions of the reaction region may expose additional functional groups to produce at least a local change in osmolality or pH, surface energy, or surface charge.

In some embodiments of the system, the remotely activatable control element may respond to the control signal by producing or absorbing heat or by changing shape. The remotely activatable control element may include a valve element or a structural element. The system may include an outlet through which a product of the chemical reaction is released into the environment or an inlet through which a second material capable of participating in the chemical reaction enters the reaction region. The first material, included in the reaction region, may be a reactant that is modified by participation in the chemical reaction or a non-reactant material that modifies at least one condition at which the reaction occurs. The first material may be a catalyst that facilitates the chemical reaction but is not significantly modified by the chemical reaction. The body structure may be adapted for positioning in an environment selected from a body of an organism, a body of water, or a contained fluid volume, which may be, for example, an industrial fluid volume, an agricultural fluid volume, a swimming pool, an aquarium, a drinking water supply, and an HVAC system cooling water supply.

Figure 41A:
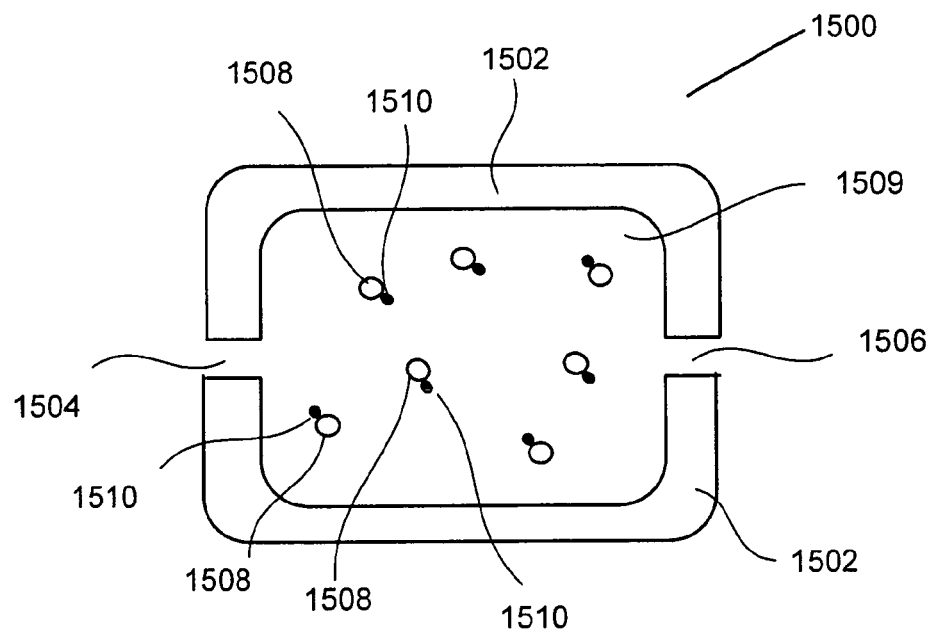
FIG. 41 depicts a reaction device including a plurality of electrically or magnetically responsive elements.
Figure 41B:
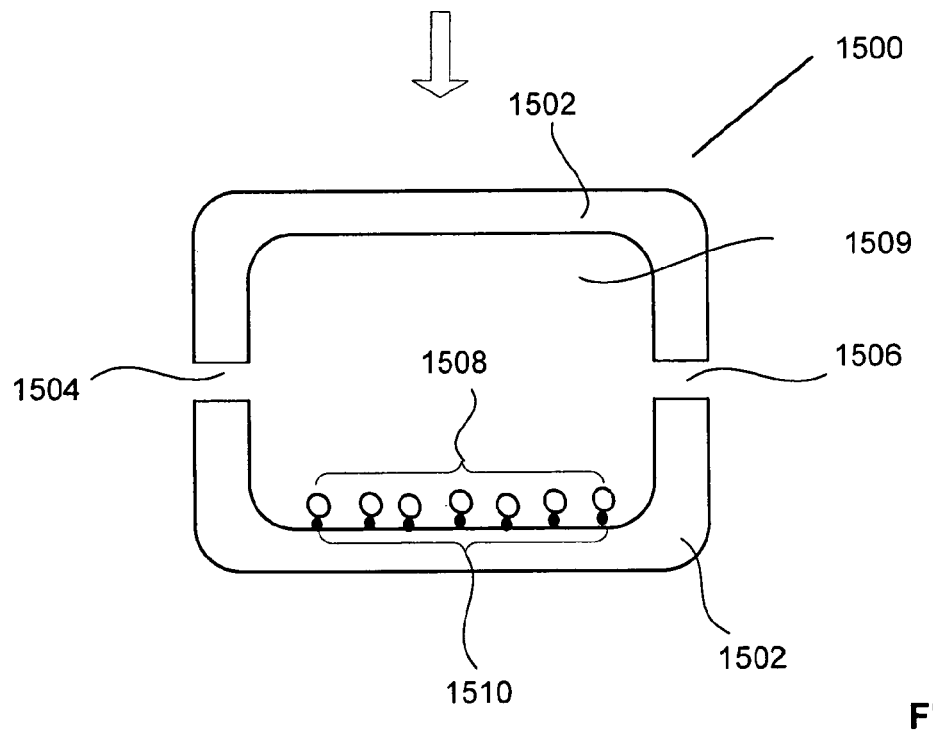

FIGS. 41A and 41B depict a reaction device 1500 which includes body structure 1502, inlet 1504, and outlet 1506. In FIG. 41A, magnetically or electrically responsive elements 1510, each of which is coupled to a first material 1508, are disposed within the reaction space 1509 within body structure 1502. First material 1508 is a material that influences or participates in a chemical reaction. Upon application of a magnetic or electric field, magnetically or electrically responsive elements 1510 move to a wall of body structure 1502, so that the effective concentration of first material 1508 within reaction space 1509 is reduced as depicted in FIG. 41B. Reaction device 1500 represents another alternative embodiment of a system include a remotely activatable control element; in this case magnetically or electrically responsive elements 1510 function as remotely activatable control elements.

A remote controller capable of producing a static or quasi-static electromagnetic control signal and suitable for use in a reaction system as just described may include an electromagnetic signal generator capable of producing a static or quasi-static magnetic or electric field control signal sufficient to produce activation of a remotely activatable magnetically or electrically responsive control element of a reaction device located in an environment to produce a desired rate of a chemical reaction in the reaction device and an electromagnetic signal transmitter capable of transmitting the static or quasi-static magnetic or electric field control signal to the remotely activatable magnetically or electrically responsive control element through the environment when the remote controller is positioned at a location remote from the reaction device. Such a remote controller may include electrical circuitry. The electromagnetic signal generator may include one or more electromagnets or permanent magnets or electric field generators or poled electrets. The electromagnetic signal produced by the remote controller may have a strength sufficient to produce a change in dimension or position or orientation in the remotely activatable control element, the change in dimension or position or orientation causing a change in the rate of the chemical reaction in the reaction device. In some embodiments, the magnetic or electric field control signal may have strength sufficient to produce a change in temperature of the remotely activatable control element or a change in shape or position or orientation in a remotely activatable control element. Such a remotely activatable control element may include, for example, a shape memory material, a bimetallic structure, or a polymeric material. As discussed in connection with FIG. 32, the remote controller may include a signal input adapted for receiving a feedback signal from the environment, and the magnetic or electric field control signal may then be determined based at least in part upon the feedback signal. For example, the feedback signal may correspond to the concentration or activity of a chemical in the environment, the ionic strength or pH of the environment, the temperature or pressure of the environment or some other environmental parameter. Alternatively, or in additional, the remote controller may include a signal input adapted for receiving a feedback signal from the reaction device, e.g., as shown in FIG. 33, and the magnetic or electric field control signal may produced based at least in part upon the feedback signal from the reaction device. In some embodiments, the magnetic or electric field control signal may be produced at least in part according to a pre-programmed pattern or predetermined activation pattern. In some embodiments, the magnetic or electric field control signal may be produced based on a model-based calculation. The remote controller may include a memory capable of storing a pre-determined activation pattern, or model parameters used in the model-based calculation.

The magnetic or electric field control signal produced by the remote controller may have one or both of a defined magnetic field strength or a defined electric field strength. At low frequencies the electrical and magnetic components of an electromagnetic field are separable when the field enters a medium. Therefore, in static and quasi-static field application, the electromagnetic field control signal may be considered as an electrical field or a magnetic field. A quasi-static field is one that varies slowly, i.e., with a wavelength that is long with respect to the physical scale of interest or a frequency that is low compared to the characteristic response frequency of the object or medium; therefore, the frequency beyond which a field will no longer be considered 'quasi-static' is dependent upon the dimensions or electrodynamic properties of the medium or structure(s) influenced by the field.

Figure 42:
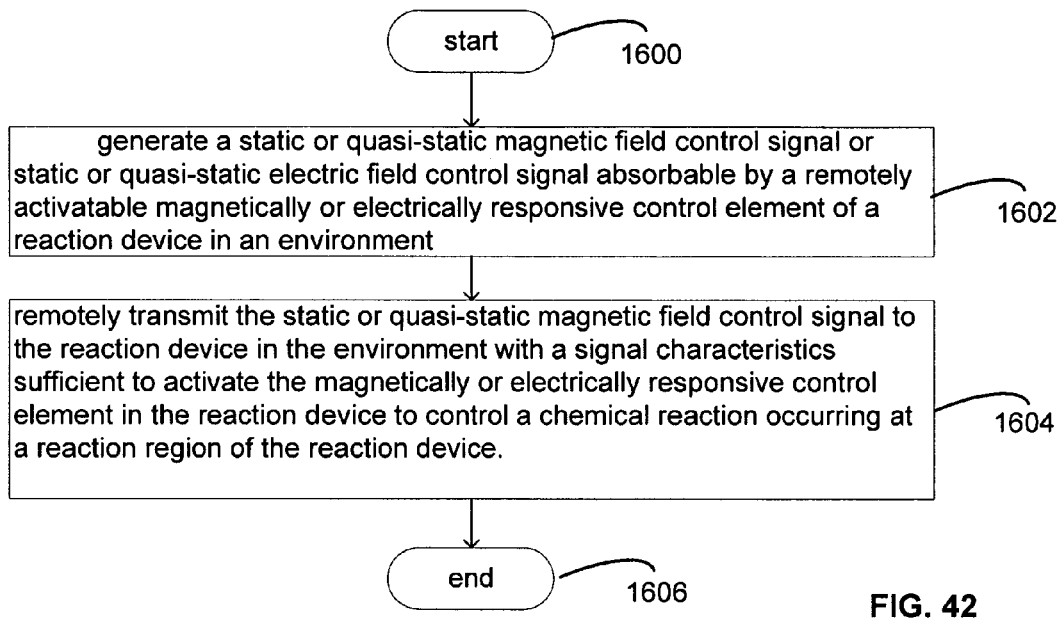
FIG. 42 is a flow diagram of an embodiment of a method of performing a reaction.

FIG. 42 is a flow diagram of a method of controlling a reaction device as described above, which may include generating a static or quasi-static magnetic field control signal or static or quasi-static electric field control signal absorbable by a remotely activatable magnetically or electrically responsive control element of a reaction device in an environment at step 1602 and remotely transmitting the static or quasi-static magnetic field control signal or static or quasi-static electric field control signal to the reaction device in the environment with a field strength sufficient to activate the magnetically or electrically responsive control element in the reaction device to control a chemical reaction occurring at a reaction region of the reaction device at step 1604. The method may include generating and transmitting the magnetic field control signal to the reaction device with a control signal source at a location remote from the reaction device. The magnetic field control signal may be generated from a model-based calculation, or based on a stored pattern. The method may also include receiving a feedback signal from the environment, and based upon the feedback signal, generating a magnetic field control signal having frequency composition and strength expected to produce a desired feedback signal. As discussed herein, receiving a feedback signal from the environment may include receiving a measure of osmolality or pH, temperature, pressure or concentration or activity of a chemical within at least a portion of the environment. In other embodiments, the method may include receiving a feedback signal from the reaction device, and based upon the feedback signal, generating a magnetic field control signal having frequency composition and amplitude expected to produce a desired feedback signal. Receiving a feedback signal from the reaction device may include, for example, receiving a signal representing a concentration of a reactant at the reaction region of the reaction device. Related embodiments not shown will employ quasi-static electric fields and devices responsive thereto to effect the same functions for the same purposes.

In further embodiments, the method may include receiving user input of one or more control parameters; and based upon the one or more control parameters, generating a magnetic or electric field control signal having frequency composition and amplitude expected to produce a desired rate of reaction in the reaction device. The method may include activating the magnetically or electrically responsive control element to produce heating or cooling of the magnetically or electrically responsive control element sufficient to modify the chemical reaction occurring at the reaction region, or to produce a change in configuration of the magnetically or electrically responsive control element sufficient to modify the chemical reaction occurring at the reaction region. For example, the change in configuration may include expansion of the magnetically or electrically responsive control element, or a change in shape of the magnetically or electrically responsive control element.

The steps of generating an electromagnetic control signal and remotely transmitting the electromagnetic control signal to the reaction device may be performed according to instructions provided in the form of software, hardware or firmware.

Various embodiments may be configured for use with specific frequencies of electromagnetic signal. For example, an embodiment of a reaction system configured to be controlled by a RF (radio frequency) control signal may include a body structure adapted for positioning in an environment, a reaction region located in or on the body structure including a first material capable of influencing a chemical reaction, and a remotely activatable control element operably coupled to the body structure and responsive to a radio-frequency electromagnetic control signal to modify one or more of the rate or kinetics of the chemical reaction. The remotely activatable control element may modify one or more of the rate or reaction kinetics of the chemical reaction by modifying the influence of the first material on the chemical reaction. The reaction system may take a form as depicted generally in FIG. 6 for example. In some embodiments, the remotely activatable control element may modify the rate of exposure of a reactant capable of participating in the chemical reaction to the first material.

The remotely activatable control element may respond to the control signal by changing in at least one dimension. The remotely activatable control element may include a polymer, ceramic, dielectric or metal, a shape memory material such as a shape memory polymer or a shape memory metal, a bimetallic structure, a hydrogel, or a ferrogel. The remotely activatable control element may include a magnetically or electrically active material, which may be, for example, a permanently magnetizable material, a ferromagnetic material, a ferrimagnetic material, a ferrous material, a ferric material, a dielectric, a ferroelectric, a piezoelectric, a diamagnetic material, a paramagnetic material, or an antiferromagnetic material. The remotely activatable control element may be formed from various combinations of materials, including but not limited to materials such as those listed above; for example, a combination of polymer and a magnetically and/or electrically active component may be used in the remotely activatable control element. Such a magnetically and/or electrically active component may be heatable by the incident electromagnetic control signal, and heating or cooling of the magnetically or electrically active component may then cause the polymer to undergo a change in configuration that modifies the influence of the first material on the chemical reaction.

The reaction region may be located in an interior portion of the body structure and may be at least intermittently in fluid communication with the environment via at least one inlet or outlet. The reaction region may be located on an exterior portion of the body structure in fluid communication with the environment. The system may include a valve that is responsive to a change in at least one dimension of the remotely activatable control element. Additional portions of the reaction region may be exposed responsive to the change in at least one dimension of the remotely activatable control element. The surface area of the reaction region may be increased responsive to the change in at least one dimension of the remotely activatable control element. The volume containing the reaction region within the interior portion of the body structure may be increased responsive to the change in at least one dimension of the remotely activatable control element. The remotely activatable control element may respond to the control signal by producing heat. The remotely activatable control element may include a valve element or a structural element.

The system may include an outlet through which a product of the chemical reaction is released into the environment or an inlet through which a second material capable of participating in the chemical reaction enters the reaction region. The first material is a reactant that is modified by participation in the chemical reaction, or a non-reactant material that modifies at least one condition at which the reaction occurs (e.g., polarity, osmolality or pH, or charge of all or a portion of the reaction region); it may be a catalyst that facilitates the chemical reaction but is not significantly modified by the chemical reaction.

A remote controller for use in such a reaction system may include an electromagnetic signal generator capable of producing a radio frequency electromagnetic signal configured to be received by a remotely activatable control element of a reaction device located in an environment and to activate the remotely activatable control element to produce a desired rate of a chemical reaction in the reaction device and an electromagnetic signal transmitter capable of transmitting the radio frequency electromagnetic signal to the remotely activatable control element. The electromagnetic signal generator may include electrical circuitry, including, for example, a microprocessor.

The remote controller may produce an electromagnetic signal at least in part according to a pre-programmed pattern. The electromagnetic signal may have a strength and frequency composition sufficient to produce a change in dimension, temperature, or shape in the remotely activatable control element. For example, the strength and frequency composition may be sufficient to produce a change in shape in a remotely activatable control element comprising a shape memory material such as a shape memory metal or a shape memory polymer, a bimetallic structure, or a polymeric material. The remote controller may include a signal input adapted for receiving a feedback signal from the environment, wherein the electromagnetic signal is determined based at least in part upon the feedback signal. An environment feedback signal may correspond to the concentration or activity of a chemical in the environment, the osmolality or pH of the environment, or the pressure or temperature of the environment. Alternatively, or in addition, the remote controller may include a signal input adapted for receiving a feedback signal from the reaction device, wherein the electromagnetic signal is determined based at least in part upon the feedback signal. In some embodiments, the electromagnetic signal may be produced based at least in part upon a predetermined activation pattern. The remote controller may include a memory capable of storing the pre-determined activation pattern. The electromagnetic signal may be produced based on a model-based calculation. The remote controller may then include a memory capable of storing model parameters used in the model-based calculation. The remote controller may produce an electromagnetic signal having one or both of a defined magnetic field strength or a defined electric field strength, as the electromagnetic signal is not necessarily a radiated one.

Figure 43:
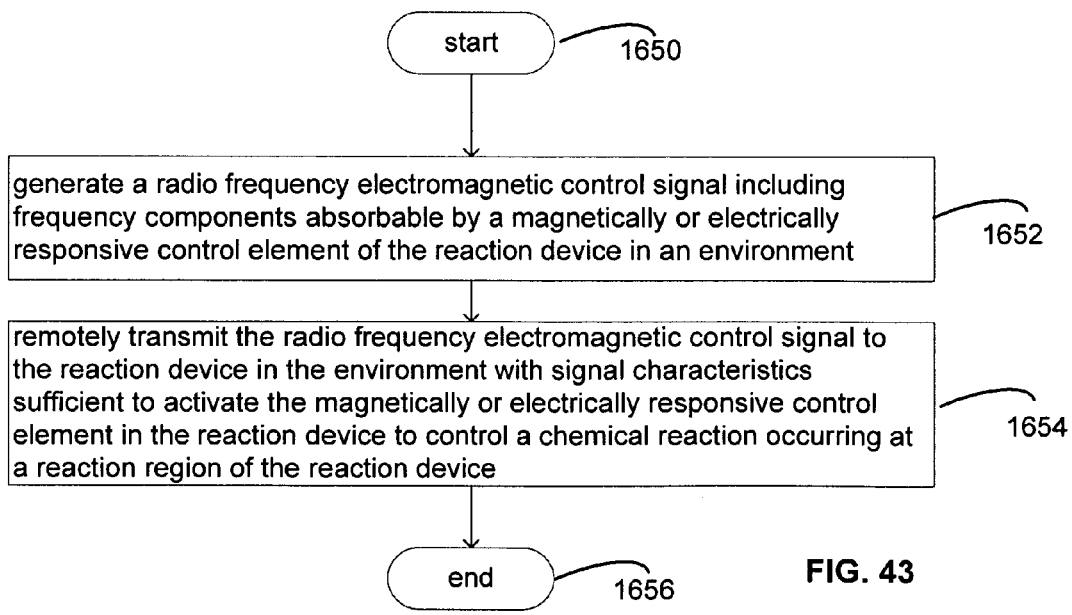
FIG. 43 is a flow diagram of an embodiment of a method of performing a reaction.

FIG. 43 is a flow diagram of a method of controlling a reaction device with a radio frequency control signal. In general, a method of controlling a reaction device may include generating a radio frequency electromagnetic control signal including frequency components absorbable by a magnetically or electrically responsive control element of the reaction device in an environment as shown at step 1652 and remotely transmitting the radio frequency electromagnetic control signal to the reaction device in the environment with signal characteristics sufficient to activate the magnetically or electrically responsive control element in the reaction device to control a chemical reaction occurring at a reaction region of the reaction device at step 1654. The method may include generating and transmitting the radio frequency electromagnetic control signal to the reaction device with a remote control signal source. The method may also include generating the radio frequency electromagnetic control signal from a model-based calculation or generating the radio frequency electromagnetic control signal based on a stored pattern. In some embodiments, the method may include receiving a feedback signal from the environment; and based upon the feedback signal, generating a radio frequency electromagnetic control signal having frequency composition and amplitude expected to produce a desired feedback signal. Receiving a feedback signal from the environment may include receiving a measure of osmolality, pH, pressure or temperature, or the concentration or activity of a chemical within at least a portion of the environment. In some embodiments, the method may include receiving a feedback signal from the reaction device, and based upon the feedback signal, generating a radio frequency electromagnetic control signal having frequency composition and amplitude expected to produce a desired feedback signal. A feedback signal from the reaction device may represent a concentration of a reactant at the reaction region of the reaction device, for example. In some embodiments, the method may include receiving user input of one or more control parameters, and based upon the one or more control parameters, generating a radio frequency electromagnetic control signal having frequency composition and amplitude expected to produce a desired rate of reaction in the reaction device. The method may include activating the magnetically or electrically responsive control element to produce heating or a change in configuration of the magnetically or electrically responsive control element.

Methods of controlling the reaction device as described herein may include generating a radio frequency electromagnetic control signal and remotely transmitting the radio frequency electromagnetic control signal to the reaction device according to instructions provided in the form of software, hardware or firmware.

Figure 44:
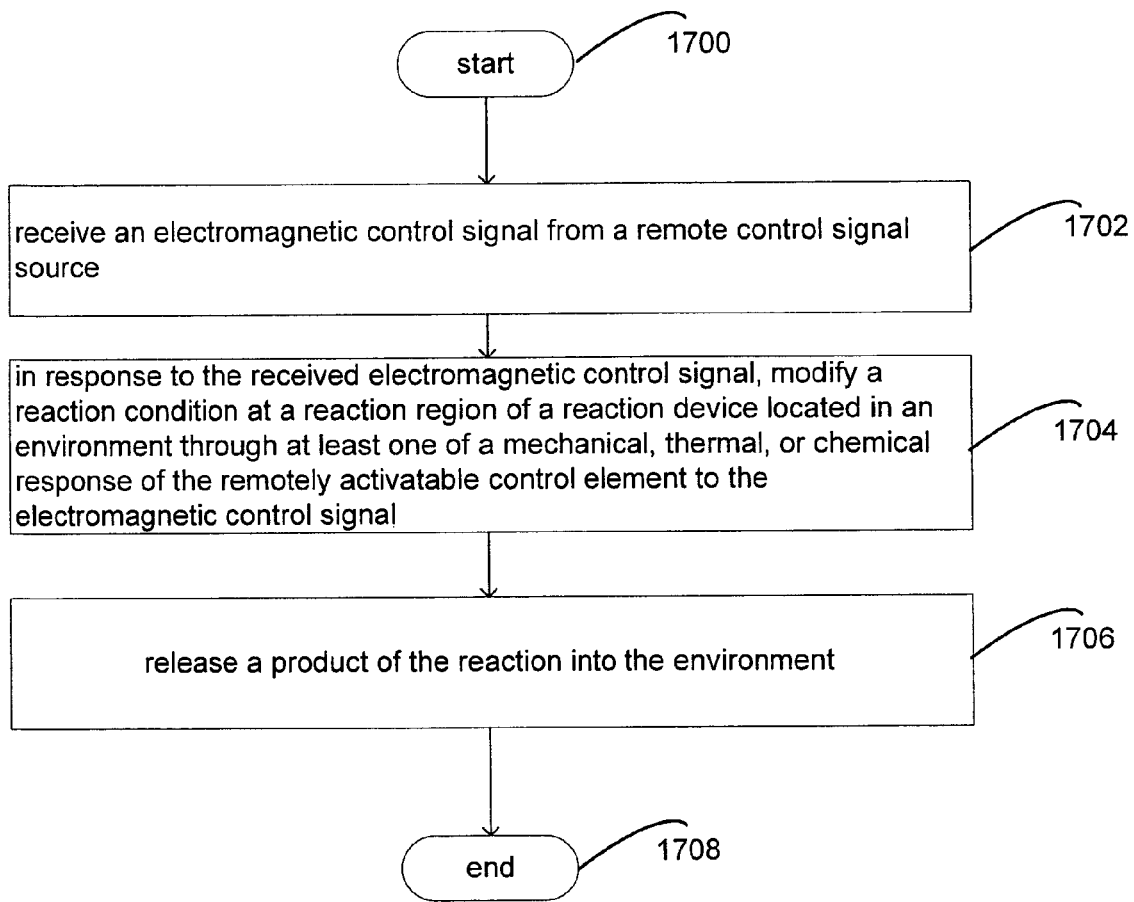
FIG. 44 is a flow diagram of an embodiment of a method of controlling a reaction device.

FIG. 44 is a flow diagram of a reaction method as carried out in remotely controlled reaction systems, of which various examples are described herein. The method may include receiving an electromagnetic control signal from a remote control signal source at step 1702; in response to the received electromagnetic control signal, modifying a reaction condition at a reaction region of a reaction device located in an environment through at least one of a mechanical, thermal, or chemical response of the remotely activatable control element to the electromagnetic control signal at step 1704; and releasing a product of the reaction into the environment at step 1706. The method may also include receiving a reactant capable of taking part in the reaction from the environment.

The method may include modifying a reaction condition at the reaction region by modifying the area of the reaction region, for example, increasing or decreasing the area of the reaction region. Increasing the area of the reaction region may include increasing or decreasing the distances between reaction sites in the reaction region, and/or it may include increasing or decreasing the number of available reaction sites in the reaction area. The method may include modifying a reaction condition at the reaction region by heating or cooling at least a portion of the reaction region, or by modifying the osmolality or pH, surface charge, or surface energy of at least a portion of the reaction region. In some embodiments, modifying a reaction condition at the reaction region may include modifying a parameter of a reaction space within the reaction device, the reaction space containing the reaction region. Modifying a reaction condition at the reaction region may include modifying the volume of the reaction space, heating or cooling at least a portion of the reaction space, or modifying the osmolality or pH or chemical composition of at least a portion of the reaction space.

The method may include receiving the electromagnetic control signal with a magnetically or electrically active material, such as a permanently magnetizable material, a ferromagnetic material, a ferrimagnetic material, a ferrous material, a ferric material, a diamagnetic material, a dielectric or ferroelectric or piezoelectric material, a paramagnetic material, or an antiferromagnetic material. In some embodiments, the magnetically or electrically active material may be a polymer or a biomolecule. Receiving the electromagnetic control signal with the magnetically or electrically active material may result in heating or cooling, acceleration, vibration, change in orientation, or change in position of the magnetically or electrically active material.

In other embodiments, the method may include receiving the electromagnetic control signal with an antenna, a resonant element, or a chemical bond. Receiving the electromagnetic control signal may include interacting with a static or quasi-static magnetic or electrical field, or it may include a radio-frequency electromagnetic signal, a microwave electromagnetic signal, an infrared wavelength electromagnetic signal, an optical wavelength electromagnetic signal, or an ultraviolet wavelength electromagnetic signal. Releasing the product of the reaction may include releasing a beneficial material or releasing a deactivated deleterious material.

Figure 45:
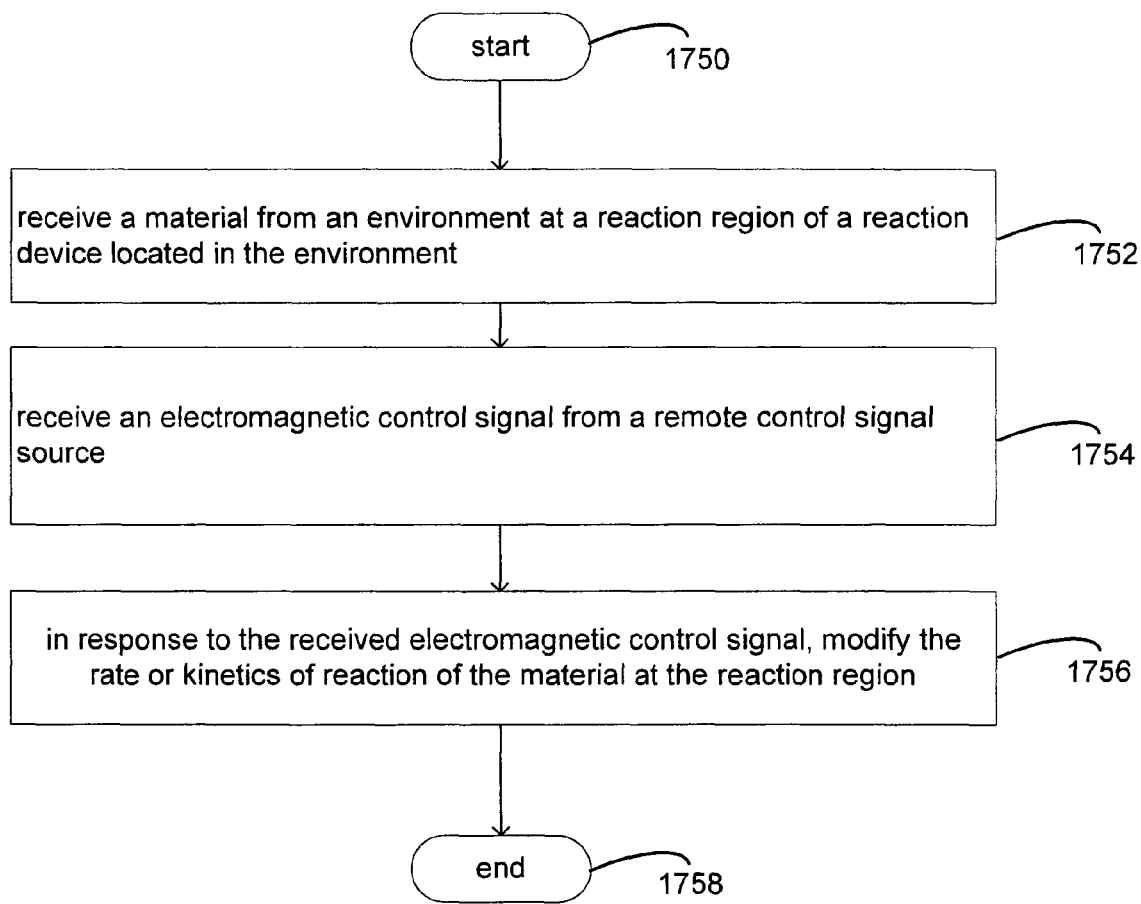
FIG. 45 is a flow diagram of an embodiment of a reaction method.

FIG. 45 is a flow diagram of a reaction method. The reaction method may include receiving a material from an environment at a reaction region of a reaction device located in the environment at step 1752, receiving an electromagnetic control signal from a remote control signal source at step 1754, and in response to the received electromagnetic control signal, modifying the rate or kinetics of reaction of the material at the reaction region at step 1756. In some variants of such a method, modifying a reaction condition at the reaction region may be accomplished by modifying the area of the reaction region, i.e., either increasing or decreasing the area of the reaction region. Increasing the area of the reaction region may increase the distances between reaction sites in the reaction region or it may increase the number of available reaction sites in the reaction area. Decreasing the area of the reaction region may decrease the distances between reaction sites in the reaction region or it may decrease the number of available reaction sites in the reaction area, for instance in order to modify the rate of diffusion of a chemical compound.

Modifying a reaction condition at the reaction region may also be accomplished by heating or cooling at least a portion of the reaction region, or by modifying the osmolality or pH, surface charge, or surface energy of at least a portion of the reaction region. Similarly, modifying a reaction condition at the reaction region may include modifying a parameter of a reaction space within the reaction device, the reaction space containing the reaction region, e.g. by modifying the volume of the reaction space, heating or cooling at least a portion of the reaction space, or modifying the osmolality, pH, pressure, temperature or chemical composition of at least a portion of the reaction space.

The method may include receiving the electromagnetic control signal with a magnetically or electrically active material such as a permanently magnetizable material, a ferromagnetic material, a ferrimagnetic material, a ferrous material, a ferric material, a diamagnetic material, a dielectric, ferroelectric or piezoelectric material, a paramagnetic material, or an antiferromagnetic material. In some cases, magnetically active material may be a polymer or a biomolecule. In still other embodiments, the method may include receiving the electromagnetic control signal with an antenna or a resonant element. In still other embodiments, the method may include receiving the electromagnetic control signal with at least one chemical bond. Receiving the electromagnetic control signal includes receiving a static or quasi-static magnetic field, a static or quasi-static electrical field, or a radio frequency, microwave, infrared, optical, or ultraviolet electromagnetic signal. Releasing the product of the reaction may include releasing a beneficial material or a deactivated deleterious material.

A reaction system that utilizes an electromagnetic field control signal may include a reaction device and a remote control signal source. The reaction device may include a body structure adapted for positioning in an environment, a reaction region located in or on the body structure, the reaction region including a first material capable of influencing a chemical reaction, and a remotely activatable control element operably coupled to the body structure and responsive to an electromagnetic control signal to modify one or more of the rate or kinetics of the chemical reaction. The remote signal source may be capable of generating an electromagnetic control signal sufficient to activate the remotely activatable control element to produce a desired rate of the chemical reaction. The remotely activatable control element may respond to the control signal by changing in at least one dimension, or by changing in position or orientation. The remotely activatable control element may include a polymer, a ceramic, a metal, a dielectric, a shape memory material such as a shape memory polymer or a shape memory metal, a bimetallic structure, a hydrogel, a ferrogel, or a magnetically or electrically active material such as a permanently magnetizable material, a ferromagnetic material, a ferrimagnetic material, a ferrous material, a ferric material, a dielectric or ferroelectric or piezoelectric material, a diamagnetic material, a paramagnetic material, or an antiferromagnetic material. In some embodiments, the remotely activatable control element may include a composite structure formed of two or more materials. For example, the remotely activatable control element may include a polymer and a magnetically or electrically active component, such that the magnetically or electrically active component may be heated or cooled by the incident electromagnetic control signal, and heating or cooling of the magnetically or electrically active component causes the polymer to undergo a change in configuration that modifies the influence of the first material on the chemical reaction. The remotely activatable control element may be responsive to a static or quasi-static electrical field or static or quasi-static magnetic field. In some embodiments, the remotely activatable control element may be responsive to non-ionizing electromagnetic radiation. The remotely activatable control element may be responsive to radio-frequency, microwave, infrared, millimeter wave, optical, or ultraviolet electromagnetic signal. In some embodiments, the reaction region of the reaction device may be located in an interior portion of the body structure and be at least intermittently in fluid communication with the environment via at least one inlet or outlet. In other embodiments, the reaction region may be located on an exterior portion of the body structure in fluid communication with the environment. In the case that the reaction region is located in an interior portion of the body structure, the system may also include a valve responsive to a change in at least one dimension of the remotely activatable control element. The valve may be configured to increase the flow of fluid into the reaction region or flow of fluid out of the reaction region responsive to the change in at least one dimension of the remotely activatable control element. Conversely, the valve may be configured to decrease flow of fluid into or out of the reaction region responsive to the change in at least one dimension of the remotely activatable control element.

In some embodiments, additional portions of the reaction region may be exposed responsive to the change in at least one dimension of the remotely activatable control element. The surface area of the reaction region may be increased responsive to the change in at least one dimension of the remotely activatable control element. In some embodiments, a volume containing the reaction region within the interior portion of the body structure may be increased responsive to the change in at least one dimension of the remotely activatable control element. The remotely activatable control element may be or form a part of a heating or cooling element, a valve element, or a structural element. The system may include one or more of an outlet through which a product of the chemical reaction is released into the environment or an inlet through which a second material capable of participating in the chemical reaction enters the reaction region. The system may include a body structure adapted for positioning in an environment which may be, for example, a body of an organism, a body of water, or a contained fluid volume such as an industrial fluid volume, an agricultural fluid volume, a swimming pool, an aquarium, a drinking water supply, or an HVAC system cooling water supply.

As described herein, various reaction devices and systems may operate under software control. In general, software for controlling a reaction device may include instructions for generating an electromagnetic control signal including frequency components absorbable by a magnetically or electrically responsive control element of the reaction device in an environment and instructions for remotely transmitting the electromagnetic control signal to the reaction device in the environment with a signal strength or duration or frequency content or other pertinent parameter sufficient to produce at least one of mechanical, thermal or chemical activation of the magnetically or electrically responsive control element in the reaction device to control a chemical reaction occurring at a reaction region of the reaction device. The instructions for generating an electromagnetic control signal may include instructions for calculating the electromagnetic control signal based on a model or for generating the electromagnetic control signal based on a pattern stored in a data storage location. In some embodiments, the software may include instructions for receiving a feedback signal from the environment and for generating the electromagnetic control signal based at least in part upon the received feedback signal. The software instructions may provide for generation of an electromagnetic control signal having frequency composition and amplitude expected to produce a desired feedback signal. Additional instructions may be provided for receiving a feedback signal from the reaction device generating the electromagnetic control signal based at least in part upon the received feedback signal; again, the electromagnetic control signal may be generated with frequency composition, polarization, directional properties, spatial gradients and amplitude expected to produce a desired feedback signal. The software may also include instructions for receiving user input of one or more control parameters; and instructions for generating the electromagnetic control signal based upon the one or more control parameters.

Figure 46:
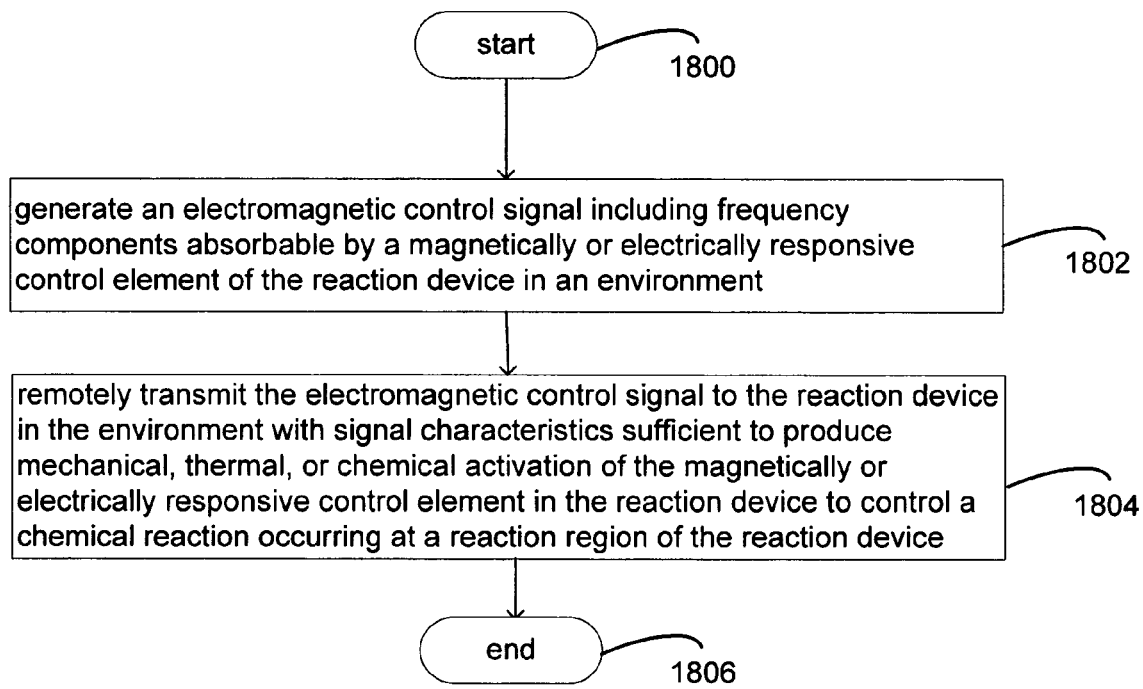
FIG. 46 is a flow diagram of an embodiment of a method of controlling a reaction device.

FIG. 46 is a flow diagram of a method of controlling a reaction device according to various embodiments disclosed herein, a method of controlling a reaction device may include generating an electromagnetic control signal including frequency components absorbable by a magnetically or electrically responsive control element of the reaction device in an environment as shown at step 1802 and remotely transmitting the electromagnetic control signal to the reaction device in the environment with signal characteristics sufficient to produce mechanical, thermal or chemical activation of the magnetically or electrically responsive control element in the reaction device to control a chemical reaction occurring at a reaction region of the reaction device as shown at step 1804. The method may include generating and transmitting the electromagnetic control signal with a remote control signal source. The electromagnetic control signal may be generated from a model-based calculation or from a stored pattern. The method may include receiving a feedback signal from the environment, and based upon the feedback signal, generating an electromagnetic control signal having signal characteristics expected to produce a desired feedback signal. Such a feedback signal from the environment includes may include a measure of osmolality, pH, pressure, temperature, or the concentration or activity of a chemical within at least a portion of the environment. In certain embodiments, the method may include receiving a feedback signal from the reaction device; and based upon the feedback signal, generating an electromagnetic control signal having frequency composition and amplitude expected to produce a desired feedback signal. Such a feedback signal may, for example, represent a concentration of a reactant at the reaction region of the reaction device, the temperature of the reaction device, or another parameter of at least a portion of the reaction device.

The method may also include receiving user input of one or more control parameters; and based upon the one or more control parameters, generating an electromagnetic control signal having signal characteristics expected to produce a desired rate of reaction in the reaction device. In particular, the method may include activating the magnetically or electrically responsive control element to produce heating or cooling of the magnetically or electrically responsive control element, where the heating or cooling modifies the chemical reaction occurring at the reaction region, or activating the magnetically or electrically responsive control element to produce a change in configuration of the magnetically or electrically responsive control element, where the change in configuration modifies the chemical reaction occurring at the reaction region. The change in configuration may be, for example, an expansion of the magnetically or electrically responsive control element, which causes exposure of reaction sites at the reaction region or changes the density of reaction sites at the reaction region. In one embodiment, the method may be applied in a system where the magnetically or electrically responsive control element includes a polymer, and the expansion of the magnetically or electrically responsive control element causes opening of pores in the polymer. In some embodiments of the method, the change in configuration may include a change in the shape of the magnetically or electrically responsive control element. In various embodiments of the method, the steps of generating an electromagnetic control signal and remotely transmitting the electromagnetic control signal to the reaction device may be performed according to instructions provided in the form of software, hardware or firmware.

Figure 47:
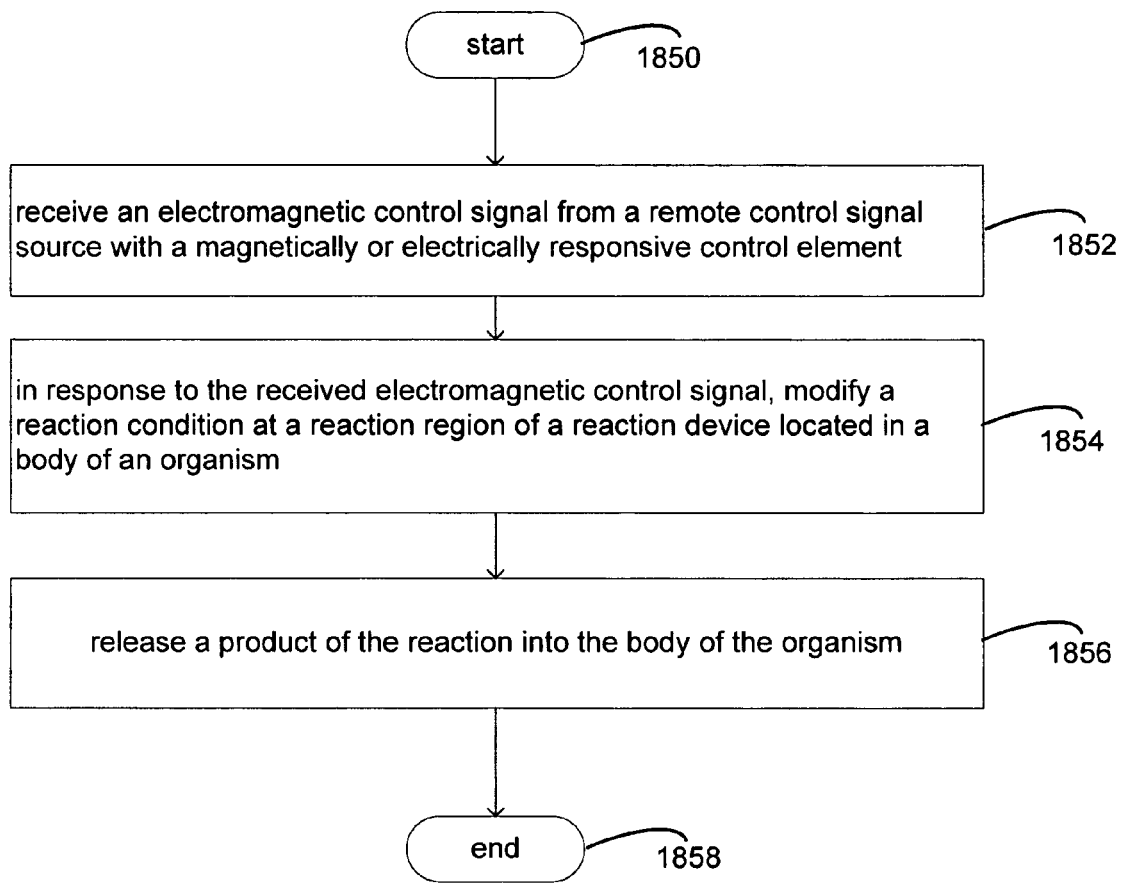
FIG. 47 is a flow diagram of an embodiment of a method of controlling a reaction device.

FIG. 47 is a flow diagram of a method of controlling a reaction device in a body of an organism. The method may include receiving an electromagnetic control signal from a remote control signal source with a magnetically or electrically responsive control element as indicated at step 1852, modifying a reaction condition at a reaction region of a reaction device located in a body of an organism in response to the received electromagnetic control signal as indicated at step 1854, and releasing a product of the reaction into the body of the organism as indicated at step 1856. In certain embodiments, the method may be carried out with a reaction device in the body of an animal or a human, a plant, or various other organisms. The method may include receiving a reactant capable of taking part in the reaction from the environment, which may be, for example, a biomolecule, a synthetic compound, or various other materials present in the environment. The method may include modifying a reaction condition at the reaction region by modifying the area of the reaction region, which may have the effect of modifying the distances between reaction sites in the reaction region or modifying the number of available reaction sites in the reaction area, for example. In some embodiments, the method may include modifying a reaction condition at the reaction region by heating or cooling at least a portion of the reaction region, by modifying the osmolality, pH, surface charge, or surface energy of at least a portion of the reaction region. Modifying a reaction condition at the reaction region may include modifying a parameter of a reaction space within the reaction device, the reaction space containing the reaction region. As noted previously, this may include modifying the volume of the reaction space, heating or cooling at least a portion of the reaction space, or modifying the osmolality or pH of at least a portion of the reaction space.

The method of FIG. 47 may be performed in a system which includes magnetically or electrically responsive control element that includes a magnetically active material such as a permanently magnetizable material, a ferromagnetic material, a ferrimagnetic material, a ferrous material, a ferric material, a dielectric or ferroelectric or piezoelectric material, a diamagnetic material, a paramagnetic material, or an antiferromagnetic material. In some embodiments, the magnetically or electrically active material may be a polymer or a biomolecule. The method may include receiving the electromagnetic control signal with the magnetically or electrically responsive control element which results in heating of the magnetically or electrically active material. In some embodiments, receiving the electromagnetic control signal with the magnetically or electrically responsive control element results in vibration, change in orientation or change in position, change in configuration or other movement of part or all of the magnetically or electrically active material. A change in configuration is contemplated to include a local or global change in shape or volume, for example. The method may also include receiving the electromagnetic control signal with an antenna, a resonant element, a chemical bond or other gain element.

Receiving the electromagnetic control signal may include receiving a static or quasi-static magnetic field, a static or quasi-static electrical field, a radio-frequency electromagnetic signal, a microwave electromagnetic signal, an infrared wavelength electromagnetic signal, an optical wavelength electromagnetic signal, or an ultraviolet wavelength electromagnetic signal. The method may include a step of releasing the product of the reaction includes releasing a beneficial material or a deactivated deleterious material. Examples of beneficial materials include nutrients, hormones, growth factors, medications, therapeutic compounds, enzymes, genetic materials, vaccines, vitamins, imaging agents, therapeutic compounds, cell signaling materials, pro- or anti-apoptotic agents, or neurotransmitters. Beneficial materials may be produced within a reaction system by various types of reactions, including, for example, conversion of pro-drugs to drugs, or enzymatic reaction of material in bloodstream (CYP450, cholesterol metabolism (e.g., with cholesterol monooxygenase, cholesterol reductase, cholesterol oxidase). See, for example, "Liver-Targeted Drug Delivery Using HepDirect1 Prodrugs," Erion et al., Journal of Pharmacology and Experimental Therapeutics Fast Forward, JPET 312:554-560, 2005 (first pub Aug. 31, 2004) and "LEAPT: Lectin-directed enzyme-activated prodrug therapy", Robinson et al., PNAS Oct. 5, 2004 vol. 101, No. 40, 14527-14532, published online before print Sep. 24, 2004, both of which are incorporated herein by reference.

Deactivated deleterious materials may include, for example, deactivated lipids/cholesterol, plaque, infectious agents such as microbes and infectious/misfolded proteins, inflammatory agents such as cytokines/chemokines, growth factors, and autoreactive antibodies, oxidants, toxins, poisons, heavy metals, pollutants including organochlorine pollutants such as polychlorinated biphenyls (PCB) or dichlorodiphenyldichloroethylene (p,p'-DDE) and organophosphates, tobacco products, tar, or particulates. Deactivation of deleterious material within the reaction device may occur through degrading, chemically modifying, detoxifying, adsorbing, absorbing, enveloping, or killing the substance by chemical reactions such as enzymatic degradation and modification (e.g., alcohol dehydrogenase to remove alcohol), neutralization of free radicals by antioxidant scavenging, and adsorption with magnetically or electrically polarized particles (e.g. labelled with binding moieties such as antibodies) for separation or sequestering, as a few examples.

Figure 48:
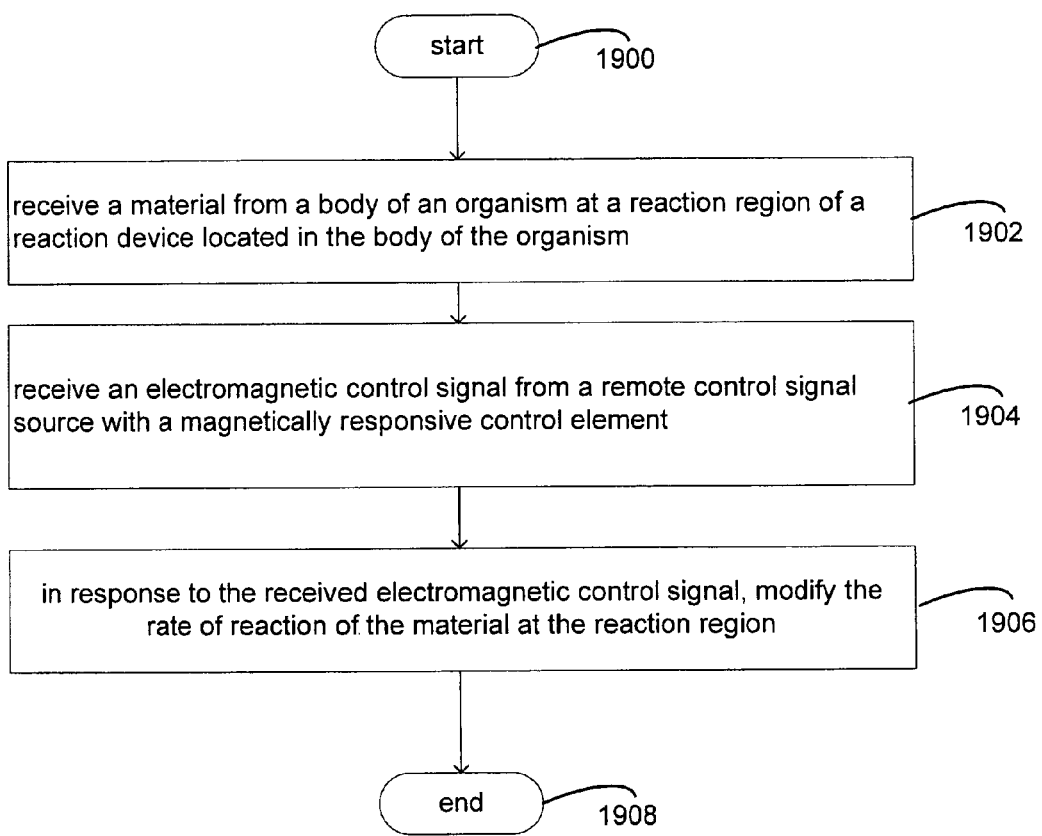
FIG. 48 is a flow diagram of an embodiment of a method of controlling a reaction device.

FIG. 48 is a flow diagram of a method of controlling a reaction device in a body of an organism. The method may include receiving a material from a body of an organism at a reaction region of a reaction device located in the body of the organism as step 1902, receiving an electromagnetic control signal from a remote control signal source with a magnetically or electrically responsive control element at step 1904, and in response to the received electromagnetic control signal, modifying the rate of reaction of the material at the reaction region at step 1906. Such a reaction method may be carried out in an animal, a human, or a plant, for example. The method may include modifying a reaction condition at the reaction region by modifying the area of the reaction region. Modifying the area of the reaction region may modify the distances between reaction sites in the reaction region, or modifying the area of the reaction region modifies the number of available reaction sites in the reaction area. The method may include modifying a reaction condition at the reaction region by heating or cooling at least a portion of the reaction region, or by modifying the osmolality, pH, surface charge or surface energy of at least a portion of the reaction region. In some embodiments, modifying a reaction condition at the reaction region may include modifying a parameter of a reaction space within the reaction device, the reaction space containing the reaction region. Modifying a reaction condition at the reaction region may include modifying the volume of the reaction space, heating or cooling at least a portion of the reaction space, or modifying the osmolality, pH, pressure, temperature or chemical composition of at least a portion of the reaction space. In some embodiments, the magnetically or electrically responsive control element which receives the electromagnetic control signal may include a magnetically or electrically active material such as permanently magnetizable material, a ferromagnetic material, a ferrimagnetic material, a ferrous material, a ferric material, a dielectric or ferroelectric or piezoelectric material, a diamagnetic material, a paramagnetic material, and an antiferromagnetic material. In some embodiments, the magnetically or electrically active material may include a polymer or a biomolecule. Receiving the electromagnetic control signal with the magnetically or electrically responsive control element may result in heating, vibration, change in orientation, or change in position, or change in configuration of the magnetically or electrically active material. The change in configuration, for example, may include a change in shape or change in volume or a change in surface area.

A further variation of the method may include receiving the electromagnetic control signal with an antenna, a resonant element, or a chemical bond. The method may include receiving a static or quasi-static magnetic field or electrical field, a radio-frequency electromagnetic signal, a microwave electromagnetic signal, an infrared wavelength electromagnetic signal, an optical wavelength electromagnetic signal or an ultraviolet wavelength electromagnetic signal.

Receiving a material from a body of an organism may include a component or precursor of a beneficial material such as genetic materials, vaccines, nutrients, vitamins, imaging agents, therapeutic compounds, hormones, growth factors, pro- or anti-apoptotic agents, or neurotransmitters. Such precursors, may include, for example, prodrugs (see, e.g., "Liver-Targeted Drug Delivery Using HepDirect1 Prodrugs," Erion et al., Journal of Pharmacology and Experimental Therapeutics Fast Forward, JPET 312:554-560, 2005 (first pub Aug. 31, 2004) and "LEAPT: Lectin-directed enzyme-activated prodrug therapy", Robinson et al., PNAS Oct. 5, 2004 vol. 101, No. 40, 14527-14532, published online before print Sep. 24, 2004, both of which are incorporated herein by reference. Beneficial materials may be produced, for example, conversion of pro-drug to drug, enzymatic reaction of material in bloodstream (CYP450, cholesterol metabolism (e.g., with cholesterol monooxygenase, cholesterol reductase, cholesterol oxidase). Alternatively, receiving a material from a body of an organism may include receiving a deleterious material for subsequent deactivation, degradation, or sequestration. Deleterious material may include lipids/cholesterol, plaque, infectious agents such as microbes and infectious/misfolded prions, inflammatory agents such as cytokines/chemokines, growth factors, and autoreactive antibodies, oxidants, toxins, poisons, heavy metals, pollutants including organochlorine pollutants such as polychlorinated biphenyls (PCB) or dichlorodiphenyldichloroethylene (p,p'-DDE) and organophosphates, tobacco products, tar, and particulates, which may be deactivated, degraded, or sequestered, e.g., by degrading, chemically modifying, detoxifying, adsorbing, absorbing, enveloping, or killing the substance by chemical reactions such as enzymatic degradation and modification (e.g., alcohol dehydrogenase to remove alcohol), neutralization of free radicals by antioxidant scavenging, adsorption with magnetically or electrically polarized particles (e.g. labelled with binding moieties such as antibodies) for separation or sequestering.

Figure 49:
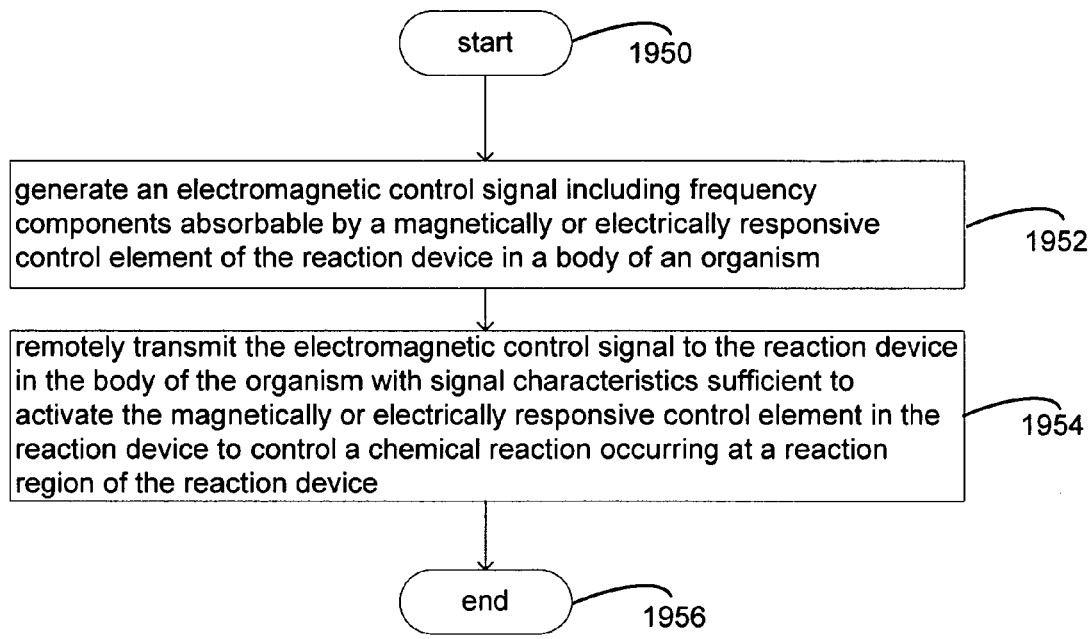
FIG. 49 is a flow diagram of an embodiment of a method of controlling a reaction device.

FIG. 49 is a flow diagram of a method of controlling a reaction device. The method of controlling a reaction device may include generating an electromagnetic control signal including frequency components absorbable by a magnetically or electrically responsive control element of the reaction device in a body of an organism at step 1952 and remotely transmitting the electromagnetic control signal to the reaction device in the body of the organism with signal characteristics sufficient to activate the magnetically or electrically responsive control element in the reaction device to control a chemical reaction occurring at a reaction region of the reaction device at step 1954. The method may include generating and transmitting the electromagnetic control signal with a remote control signal source. The electromagnetic control signal may be generated from a model-based calculation or from a stored pattern. The method may include receiving a feedback signal from the body of the organism, and, based upon the feedback signal, generating an electromagnetic control signal having waveform expected to produce a desired feedback signal. For example, receiving a feedback signal from the body of the organism may include receiving a measure of pH or temperature within at least a portion of the body of the organism. Receiving a feedback signal from the body of the organism may include receiving a measure of the concentration or activity of a chemical within at least a portion of the body of the organism. Exemplary chemicals may include proteins, lipids, carbohydrates, glycoproteins, amino acid sequences, nucleic acid sequences, or ions to name only a few.

The method may include receiving a feedback signal from the reaction device and based upon the feedback signal, generating an electromagnetic control signal having signal characteristics predicted or expected to produce a desired feedback signal. Receiving a feedback signal from the reaction device may include receiving a signal representing a concentration of a reactant at the reaction region of the reaction device. The method may include receiving user input of one or more control parameters and based upon the one or more control parameters, generating an electromagnetic control signal having signal characteristics expected to produce a desired rate of reaction in the reaction device. The method may include activating the magnetically or electrically responsive control element to produce heating or cooling or change in configuration of the magnetically or electrically responsive control element. The change in configuration may include, for example, expansion of the magnetically or electrically responsive control element, which may cause exposure of reaction sites at the reaction region or change the density of reaction sites at the reaction region. The magnetically or electrically responsive control element may include a polymer, and expansion of the magnetically or electrically responsive control element may cause opening of pores in the polymer. The change in configuration may include a change in shape of the magnetically or electrically responsive control element. The steps of generating an electromagnetic control signal and remotely transmitting the electromagnetic control signal to the reaction device may be performed according to instructions provided in the form of software, hardware or firmware.

With regard to the hardware and/or software used in the control of reaction devices and systems according to the present embodiments, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into reaction systems as exemplified herein. That is, at least a portion of the devices and/or processes described herein can be integrated into a reaction system via a reasonable amount of experimentation.

Those having skill in the art will recognize that systems as described herein may include one or more of a memory such as volatile and non-volatile memory, processors such as microprocessors and digital signal processors, computational-supporting or -associated entities such as operating systems, user interfaces, drivers, sensors, actuators, applications programs, one or more interaction devices, such as data ports, control systems including feedback loops and control implementing actuators (e.g., devices for sensing osmolality, pH, pressure, temperature, or chemical concentration, signal generators for generating electromagnetic control signals). A system may be implemented utilizing any suitable available components, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of remote controller, system configuration and reaction device may be within the scope of the invention. As has been discussed, the choice of system configuration may depend on the intended application of the system, the environment in which the system is used, cost, personal preference or other factors. System design, manufacture, and control processes may be modified to take into account choices of use environment and intended application, and such modifications, as known to those of skill in the arts device design and construction, may fall within the scope of the invention. Therefore, the full spirit or scope of the invention is defined by the appended claims and is not to be limited to the specific embodiments described herein.

The invention claimed is:

1. A reaction system comprising:
 a reaction device including:
  a body structure adapted for positioning in an environment;
  a reaction region located in or on the body structure, the reaction region including a first material capable of modifying one or more of the rate or kinetics of a chemical reaction, the chemical reaction occurring at the reaction region within a fluid in at least intermittent fluid communication with the environment; and a remotely activatable control element physically coupled to the reaction region and to the body structure, the remotely activatable control element including a magnetically or electrically active material, wherein upon absorption of an electromagnetic field control signal, the remotely activatable control element produces a mechanical or a thermal response, and wherein the mechanical or thermal response of the remotely activatable control element produces a corresponding mechanical or thermal response of the reaction region, to thereby modify the influence of the first material on one or more of the rate or kinetics of the chemical reaction; and a remote control signal source capable of generating an electromagnetic control signal sufficient to be absorbed by, and produce activation of, the remotely activatable control element to produce the mechanical or thermal response of the remotely activatable control element to thereby modify the influence of the first material on one or more of the rate or kinetics of the chemical reaction.

2. The reaction system of claim 1, wherein the reaction region is located in an interior portion of the body structure and is at least intermittently in fluid communication with the environment via at least one inlet or outlet.

3. The reaction system of claim 1, wherein the reaction region is located on an exterior portion of the body structure in fluid communication with the environment.

4. The reaction system of claim 1, wherein the remotely activatable control element includes a heating element, a cooling element, or a structural element.

5. The reaction system of claim 1, wherein the remote control signal source includes software configured to control generation of the electromagnetic control signal.

6. The reaction system of claim 1, wherein the remotely activatable control element includes a polymer, ceramic, dielectric or metal.

7. The reaction system of claim 1, wherein the remotely activatable control element includes a bimetallic structure.

8. The reaction system of claim 1, wherein the remotely activatable control element includes at least one of a hydrogel and a ferrogel and a ferroelectric.

9. The reaction system of claim 1, wherein the magnetically or electrically active material includes at least one of a permanently magnetizable material, a ferromagnetic material, a ferrimagnetic material, a ferrous material, a ferric material, a dielectric or ferroelectric or piezoelectric material, a diamagnetic material, a paramagnetic material, and an antiferromagnetic material.

10. The reaction system of claim 1, wherein the remotely activatable control element is responsive to a static or quasi-static electrical field.

11. The reaction system of claim 1, wherein the remotely activatable control element is responsive to a static or quasi-static magnetic field.

12. The reaction system of claim 1, wherein the remotely activatable control element is responsive to a non-ionizing electromagnetic signal.

13. The reaction system of claim 1, wherein the remotely activatable control element is responsive to a radio-frequency electromagnetic signal.

14. The reaction system of claim 1, wherein the remotely activatable control element is responsive to a microwave electromagnetic signal.

15. The reaction system of claim 1, wherein the remotely activatable control element is responsive to an infrared electromagnetic signal.

16. The reaction system of claim 1, wherein the remotely activatable control element is responsive to a millimeter wave electromagnetic signal.

17. The reaction system of claim 1, wherein the remotely activatable control element is responsive to an optical electromagnetic signal.

18. The reaction system of claim 1, wherein the remotely activatable control element is responsive to an ultraviolet electromagnetic signal.

19. The reaction system of claim 1, including an outlet through which a product of the chemical reaction is released into the environment.

20. The reaction system of claim 1, including an inlet through which a second material capable of participating in the chemical reaction enters the reaction region.

21. The reaction system of claim 1, including a body structure adapted for positioning in an environment selected from a body of an organism, a body of water, or a contained fluid volume.

22. The reaction system of claim 1, including a body structure adapted for positioning in a contained fluid volume selected from an industrial fluid volume, an agricultural fluid volume, a swimming pool, an aquarium, a drinking water supply, and a HVAC system cooling water supply.

23. The reaction system of claim 1, wherein the remotely activatable control element includes a polymer and the magnetically or electrically active material.

24. The reaction system of claim 23, wherein the magnetically or electrically active material is capable of being heated or cooled by action of the electromagnetic control signal, and wherein heating or cooling of the magnetically or electrically active material causes the polymer to undergo a change in configuration that modifies the influence of the first material on the chemical reaction.

25. The reaction system of claim 1, wherein the remotely activatable control element responds to the control signal by changing in at least one dimension, wherein the change in at least one dimension by the remotely activatable control element produces a corresponding change in at least one dimension by the reaction region.

26. The reaction system of claim 25, wherein additional portions of the reaction region are exposed responsive to the change in at least one dimension of the remotely activatable control element.

27. The reaction system of claim 25, wherein a surface area of the reaction region is increased responsive to the change in at least one dimension of the remotely activatable control element.

28. The reaction system of claim 25, wherein a volume containing the reaction region within the interior portion of the body structure is increased responsive to the change in at least one dimension of the remotely activatable control element.

29. The reaction system of claim 25, wherein the remotely activatable control element includes a shape memory material.

30. The reaction system of claim 29, wherein the shape memory material includes a shape memory polymer or a shape memory metal.

31. A reaction system comprising:

a reaction device including:

a body structure adapted for positioning in an environment;

a remotely activatable control element coupled to the body structure and including a magnetically or electrically active material, wherein upon absorption of an electromagnetic field control signal the remotely activatable control element responds by changing in at least one dimension; and a reaction region mechanically coupled to the remotely activatable control element, the reaction region at least intermittently in fluid communication with the environment, the reaction region including a first material capable of modifying one or more of the rate or kinetics of a chemical reaction at the reaction region, the reaction region changing in dimension in response to a change in dimension of the remotely activatable control element, wherein the influence of the first material on one or more of the rate or kinetics of the chemical reaction is modified by a change in dimension of the reaction region; and a remote control signal source capable of generating an electromagnetic control signal sufficient to be absorbed by, and produce activation of, the remotely activatable control element to change the remotely activatable control element in at least one dimension to thereby modify the influence of the first material on one or more of the rate or kinetics of the chemical reaction.

32. A reaction system comprising:

a reaction device including:

a body structure adapted for positioning in an environment;

a remotely activatable control element coupled to the body structure and including a magnetically or electrically active material, wherein upon absorption of an electromagnetic field control signal the remotely activatable control element responds by heating or cooling; and a reaction region thermally coupled to the remotely activatable control element, the reaction region at least intermittently in fluid communication with the environment, the reaction region including a first material capable of modifying one or more of the rate or kinetics of a chemical reaction at the reaction region, the reaction region heating or cooling, respectively, in response to heating or cooling of the remotely activatable control element, wherein the influence of the first material on one or more of the rate or kinetics of the chemical reaction is modified by heating or cooling of the reaction region; and a remote control signal source capable of generating an electromagnetic control signal sufficient to be absorbed by, and produce activation of, the remotely activatable control element to heat or cool the remotely activatable control element to thereby modify the influence of the first material on one or more of the rate or kinetics of the chemical reaction.

* * * * *